United States Patent
Kimmelman et al.

(10) Patent No.: US 10,837,015 B2
(45) Date of Patent: Nov. 17, 2020

(54) TARGETING THE GLUTAMINE TO PYRUVATE PATHWAY FOR TREATMENT OF ONCOGENIC KRAS-ASSOCIATED CANCER

(71) Applicants: Dana-Farber Cancer Institute, Inc., Boston, MA (US); Beth Israel Deaconess Medical Center, Inc., Boston, MA (US)

(72) Inventors: Alec C. Kimmelman, Weston, MA (US); Jaekyoung Son, Somerville, MA (US); Lewis Cantley, Cambridge, MA (US); Costas A. Lyssiotis, Jamaica Plain, MA (US)

(73) Assignees: Dana-Farber Cancer Institute, Inc., Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 16/158,634

(22) Filed: Oct. 12, 2018

(65) Prior Publication Data

US 2019/0136238 A1    May 9, 2019

Related U.S. Application Data

(62) Division of application No. 14/402,824, filed as application No. PCT/US2013/042468 on May 23, 2013, now Pat. No. 10,138,479.

(60) Provisional application No. 61/651,213, filed on May 24, 2012.

(51) Int. Cl.
| | |
|---|---|
| *C12Q 1/34* | (2006.01) |
| *C12Q 1/52* | (2006.01) |
| *C12N 15/113* | (2010.01) |
| *A61K 31/04* | (2006.01) |
| *A61K 31/194* | (2006.01) |
| *A61K 31/4196* | (2006.01) |
| *A61K 31/7068* | (2006.01) |
| *C07K 16/00* | (2006.01) |

(52) U.S. Cl.
CPC ............ *C12N 15/113* (2013.01); *A61K 31/04* (2013.01); *A61K 31/194* (2013.01); *A61K 31/4196* (2013.01); *A61K 31/7068* (2013.01); *C07K 16/00* (2013.01); *C12N 15/1135* (2013.01); *C12N 15/1137* (2013.01); *C12Q 1/34* (2013.01); *C12Q 1/52* (2013.01); *C07K 2317/76* (2013.01); *C12N 2310/11* (2013.01); *C12N 2310/16* (2013.01); *C12N 2310/531* (2013.01); *G01N 2333/902* (2013.01); *G01N 2333/914* (2013.01); *G01N 2333/91188* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,046,722 A | 9/1977 | Rowland |
| 4,046,784 A | 9/1977 | Gipson |
| 4,331,647 A | 5/1982 | Goldenberg |
| 4,348,376 A | 9/1982 | Goldenberg |
| 4,361,544 A | 11/1982 | Goldenberg |
| 4,444,744 A | 4/1984 | Goldenberg |
| 4,460,459 A | 7/1984 | Shaw et al. |
| 4,460,561 A | 7/1984 | Goldenberg |
| 4,468,457 A | 8/1984 | Goldenberg et al. |
| 4,624,846 A | 11/1986 | Goldenberg |
| 4,671,958 A | 6/1987 | Rodwell et al. |
| 4,814,470 A | 3/1989 | Cohn et al. |
| 4,857,653 A | 8/1989 | Cohn et al. |
| 4,924,011 A | 5/1990 | Denis et al. |
| 5,034,506 A | 7/1991 | Summerton et al. |
| 5,093,246 A | 3/1992 | Cech et al. |
| 5,270,163 A | 12/1993 | Gold et al. |
| 5,290,957 A | 3/1994 | Correa et al. |
| 5,292,921 A | 3/1994 | Correa et al. |
| 5,332,567 A | 7/1994 | Goldengerg |
| 5,438,072 A | 8/1995 | Bobee et al. |
| 5,443,953 A | 8/1995 | Hansen |
| 5,541,297 A | 7/1996 | Hansen |
| 5,587,493 A | 12/1996 | Bouchard et al. |
| 5,601,825 A | 2/1997 | Hansen et al. |
| 5,637,288 A | 6/1997 | Goldenberg et al. |
| 5,637,684 A | 6/1997 | Cook |
| 5,677,427 A | 10/1997 | Goldenberg |
| 5,677,437 A | 10/1997 | Teng |
| 5,686,578 A | 11/1997 | Goldenberg |
| 5,698,178 A | 12/1997 | Goldenberg |
| 5,780,607 A | 7/1998 | Goodnow, Jr. |
| 5,783,682 A | 7/1998 | Cook et al. |
| 5,789,554 A | 8/1998 | Leung |
| 5,792,844 A | 8/1998 | Sanghvi |
| 5,811,234 A | 9/1998 | Roninson |
| 5,814,500 A | 9/1998 | Dietz |
| 5,922,302 A | 7/1999 | Goldenberg |
| 6,004,940 A | 12/1999 | Marasco |
| 6,187,287 B1 | 2/2001 | Leung |
| 6,319,500 B1 | 11/2001 | Goldenberg |

(Continued)

FOREIGN PATENT DOCUMENTS

| | | |
|---|---|---|
| EP | 0253738 | 1/1990 |
| EP | 0595241 | 10/1993 |

(Continued)

OTHER PUBLICATIONS

Machine Translation of EP0595241, 19 pages. (Year: 1995).*

(Continued)

*Primary Examiner* — Richard A Schnizer
(74) *Attorney, Agent, or Firm* — Fish & Richardson P.C.

(57) ABSTRACT

Methods and kits for GPP-targeting, e.g., for the treatment of oncogenic Kras-associated cancers, and methods for determining the efficacy of those methods are provided.

29 Claims, 30 Drawing Sheets

Specification includes a Sequence Listing.

(56) References Cited

U.S. PATENT DOCUMENTS

| | | |
|---|---|---|
| 2001/0024831 A1 | 9/2001 | Der Maur et al. |
| 2003/0082140 A1 | 5/2003 | Fisher |
| 2003/0153521 A1 | 8/2003 | McSwiggen |
| 2004/0121348 A1 | 6/2004 | Kreutzer et al. |
| 2005/0065105 A1 | 3/2005 | Testa et al. |
| 2012/0083761 A1 | 4/2012 | Malecki et al. |
| 2013/0023587 A1 | 1/2013 | Schroeder et al. |

FOREIGN PATENT DOCUMENTS

| | | |
|---|---|---|
| WO | WO 1991/17976 | 11/1991 |
| WO | WO 1991/19813 | 12/1991 |
| WO | WO 1993/00928 | 1/1993 |
| WO | WO 1993/00929 | 1/1993 |
| WO | WO 1994/02610 | 2/1994 |
| WO | WO 1996/01815 | 1/1996 |
| WO | WO 1996/39154 | 12/1996 |
| WO | WO 1997/03211 | 1/1997 |
| WO | WO 2004/091664 | 10/2004 |
| WO | WO 2011/143160 | 11/2011 |
| WO | WO 2013/177426 | 11/2013 |

OTHER PUBLICATIONS

Machine Translation of WO 2004091664, Description (Year: 2004).*
Arora et al., c-Myc Antisense Limits Rat Liver Regeneration and Indicates Role for c-Myc in Regulating Cytochrome P-450 3A Activity, J. Pharmacol. Exp. Ther. 292:921-928 (2000).
ATCC Cell lines by Gene Mutation (2014) retrieved on Jun. 23, 2017 from https://www.atcc.org/-/media/PDFs/Culture%Guides/Cell_Lines_by_Gene_Mutation.ashx.
Bajad, et al. Separation and quantitation of water soluble cellular metabolites by hydrophilic interaction chromatography-tandem mass spectrometry, J Chromatogr A 1125(1):76-88 (2006).
Bernstein et al., Role for a bidentate ribonuclease in the initiation step of RNA interference, Nature; 409(6818):363-366 (2001).
Borger et al, Frequent Mutation of Isocitrate Dehydrogenase (IDH)1 and IDH2 in Cholangiocarcinoma Identified Through Broad-Based Tumor Genotyping, The Oncologist 17:72-79 (2012).
Brummelkamp et al., A system for stable expression of short interfering RNAs in mammalian cells, Science; 296(5567):550-553 (2002).
Calhoun et al., Molecular Genetics of Pancreatic Cancer, Pancreatic Cancer, Eds. Lowy, Leach, Philip, US, vol. XVIII, Chapter 2, pp. 27-39 (2008).
DeBerardinis, et al. Beyond aerobic glycolysis: transformed cells can engage in glutamine metabolism that exceeds the requirement for protein and nucleotide synthesis, Proc Natl Acad Sci USA, 104(49):19345-19350 (2007).
DeLaBarre, B. et al. Full-length human glutaminase in complex with an allosteric inhibitor, Biochemistry 50(50):10764-10770 (2011).
Donzé and Picard, RNA interference in mammalian cells using siRNAs synthesized with T7 RNA polymerase, Nucleic Acids Res.; 30(10):e46 (2002).
Elbashir et al., RNA interference is mediated by 21- and 22-nucleotide RNAs, Genes Dev.; 15(2):188-200 (2001).
Elez et al, Polo-like kinase1, a New Target for Antisense Tumor Therapy, Biochem. Biophys. Res. Comm. 269:352-356 (2000).
EP Extended European Search Report dated Mar. 2, 2016 for corresponding EP Application No. 13793114.3 (12 pages).
Gaglio et al., "Oncogenic K-Ras decouples glucose and glutamine metabolism to support cancer cell growth", Molecular Systems Biology, 7(523):1-38; abstract; p. 7; Supplement; Peer Review (2011).
Gao, P. et al. c-Myc suppression of miR-23a/b enhances mitochondrial glutaminase expression and glutamine metabolism, Nature 458(7239):762-765 (2009).

Gautier et al., Alpha-DNA. IV: Alpha-anomeric and beta-anomeric tetrathymidylates covalently linked to intercalating oxazolopyridocarbazole. Synthesis, physicochemical properties and poly (rA) binding, Nucl. Acids Res.; 15(16):6625-6641 (1987).
Gazdar et al, Lung Cancer Cell Lines as Tools for Biomedical Discovery and Research, J Natl Cancer Inst. 102:1310-1321 (2010).
Gibson et al., A novel method for real time quantitative RT-PCR, Genome Research 6(10):995-1001.
Guatelli et al. Isothermal, in vitro amplification of nucleic acids by a multienzyme reaction modeled after retroviral replication, Proc. Nat. Acad. Sci. USA 87(5):1874 (1990).
Haseloff and Gerlach, Simple RNA enzymes with new and highly specific endoribonuclease activities, Nature; 334(6183):585-591 (1988).
Heasman et al., Beta-catenin signaling activity dissected in the early Xenopus embryo: a novel antisense approach, Dev. Biol.; 222:124-134 (2000).
Heid et al., Real time quantitative PCR, Genome Research 6(10):986-994, (1996).
Hollestelle et al, Phosphatidylinositol-3-0H Kinase or RAS Pathway Mutations in Human Breast Cancer Cell Lines, Mol. Cancer Res. 5(2): 195-202 (2007).
International Search Report and Written Opinion of the International Searching Authority for PCT/US2013/042468 dated Jan. 10, 2014 (28 pages).
Israel et al, The metabolic advantage of tumor cells, Molecular Cancer 10:70 (2011).
Kurtze et al, KRAS-mutated non-small cell lung cancer cells are responsive to either co-treatment with erlotinib or gefitinib and histone deacetylase inhibitors or single treatment with lapatinib, Oncology Reports 25:1021-1029 (2011).
Kwoh et al. Transcription-based amplification system and detection of amplified human immunodeficiency virus type 1 with a bead-based sandwich hybridization format, Proc. Natl. Acad. Sci. USA 86(4):1173 (1989).
Landegren et al. A ligase-mediated gene detection technique, Science 241(4869):1077 (1988).
Liou et al, Reactive oxygen species in cancer, Free Radical Research, 44(5): 479-496 (May 2010).
Locasale et al. Phosphoglycerate dehydrogenase diverts glycolytic flux and contributes to oncogenesis, Nature Genetics; 43(9):869-874 (2011).
Marasco, W.A. Intrabodies: turning the humoral immune system outside in for intracellular immunization, Gene Therapy 4(1):11-15 (1997).
Mata, A hexameric phosphorothioate oligonucleotide telomerase inhibitor arrests growth of Burkitt's lymphoma cells in vitro and in vivo, Toxicol. Appl. Pharmacol. 144(1):189-197 (1997).
Maurer et al., Small-molecule ligands bind to a distinct pocket in Ras and inhibit SOS-mediated nucleotide exchange activity, Proceedings of the Natl Acad of Sciences, US, 109(14):5299-5304 (Apr. 2012).
McManus et al., Gene silencing using micro-RNA designed hairpins, RNA, 8(6):842-850 (2002).
Monostori et al., "Determination of Glutathione and Glutathione Disulfide in Biological Samples: An In-depth Review", Journal of Chromatography B., 877:3331-3346 (2009).
Nielsen, P.E. New Molecule of Life?, Scientific American, 299(6):64-71, (2008).
Ogasawara et al, Determination of Reduced Nicotinamide Adenine Dinudeotidc Phosphate Concentration Using High-Performance Liquid Chromatography with Fluorescence Detection: Ratio of the Reduced Form as a Bio marker of Oxidative Stress, Biol. Pharm. Bull. 32(11):1819-1823, (2009).
Ouyang, H. et al. Immortal human pancreatic duct epithelial cell lines with near normal genotype and phenotype, Am J Pathol 157(5):1623-1631 (2000).
Paddison et al., Short hairpin RNAs (shRNAs) induce sequence-specific silencing in mammalian cells, Genes Dev. 16(8):948-958 (2002).
Pastan et al. Immunotoxins., Cell 47(5):641-648 (1986).
Pylayeva-Gupta et al., RAS oncogenes: weaving a tumorigenic web, Nat Rev Cancer, 11(11):761-764 (2011).

(56) References Cited

OTHER PUBLICATIONS

Rademann et al., Integrating Combinatorial Synthesis and Bioassays, Science 151:1947-1948 (2000).
Raimundo et al., "Revisiting the TCA cycle: signaling to tumor formation", Trends in Molecular Medicine, 17(11):641-649 (2011).
Rajalingam et al, Ras oncogenes and their downstream targets, Biochim Biophys Acta 1773:1177-1195(2007).
Rej, Aminooxyacetate is not an Adequate Differential Inhibitor of Aspartate Aminotransferase Isoenzymes, Clin. Chem. 23(8): 1508-1509, (1977).
Rej, Measurement of Aspartate Aminotransferase Activity: Effects of Oxamate, Clin. Chem. 25(4): 555-559 (1979).
Schreiber, Target-Oriented and Diversity-Oriented Organic synthesis in Drug Discovery, Science; 151:1964-1969 (2000).
Seth et al, On-target Inhibition of Tumor Fermentative Glycolysis as Visualized by Hyperpolarized Pyruvate, Neoplasia 13(1): 60-71 (2011).
Sharp, RNAi and double-strand RNA, Genes Dev.; 13(2):139-141 (1999).
Sigma Chemical Company catalog at p. 2061, "Pyruvate" "Salicylate" (1992).
Singh, A. et al. A gene expression signature associated with "K-Ras addiction" reveals regulators of EMT and tumor cell survival, Cancer Cell 15(6):489-500 (2009).
Son et al., Glutamine supports pancreatic cancer growth through a KRAS-regulated metabolic pathway, Nature, 496(7443):101-105 (Apr. 2013).
Son, et al. TRAIL-activated stress kinases suppress apoptosis through transcriptional upregulation of MCL-1, Cell Death Differ 17(8):1288-1301 (2010).
Southern, Detection of specific sequences among DNA fragments separated by gel electrophoresis, J. Mol. Biol.;98(3):503-517 (1975).
Strauss-Soukup, Effects of neutralization pattern and stereochemistry on DNA bending by methylphosphonate substitutions, Biochemistry 36(29):8692-8698 (1997).
Subramanian et al., Gene set enrichment analysis: a knowledge-based approach for interpreting genome-wide expression profiles, Proc Natl Acad Sci USA, 102(43):15545-15550 (2005).
Sui et al., A DNA vector-based RNAi technology to suppress gene expression in mammalian cells, Proc. Natl. Acad. Sci. USA; 99(8):5515-5520 (2002).
Summerton and Weller, Morpholino antisense oligomers: design, preparation, and properties, Antisense Nucleic Acid Drug Dev.; 7(3):187-195 (1997).
Tan et al, KRAS mutation testing in metastatic colorectal cancer, World J Gastroenterol 18(37):5171-5180 (Oct. 7, 2012).
Thornburg et al, *Targeting aspartate aminotransferase in breast cancer*, Breast Cancer Research, 10(5):R84, (12 pages) (2008).
Trachootham, D. et al. Selective killing of oncogenically transformed cells through a ROS-mediated mechanism by beta-phenylethyl isothiocyanate, Cancer Cell 10(3): 241-252 (2006).
Tuschl, RNA interference and small interfering RNAs, Chem. Biochem.; 2(4):239-245 (2001).
Vander Heiden, Targeting cancer metabolism: a therapeutic window opens, Nat Rev Drug Discov 10(9):671-684 (2011).
Vitetta et al. Redesigning nature's poisons to create anti-tumor reagents, Science 238(4830):1098-1104 (1987).
Vogelstein et al , RAS Gene Mutations in Childhood Acute Myeloid Leukemia: A Pediatric Oncology Group Study, Genes, Chromosomes & Cancer 2:159-162 (1990).
Wang, J. B. et al. Targeting mitochondrial glutaminase activity inhibits oncogenic transformation, Cancer Cell 18(3):207-219 (2010).
Ward, et al., Metabolic reprogramming: a cancer hallmark even warburg did not anticipate, Cancer Cell 21(3):297-308 (2012).
Weinberg, F. et al. Mitochondrial metabolism and ROS generation are essential for Kras-mediated tumorigenicity, Proc Natl Acad Sci USA 107(19):8788-8793 (2010).
Wise, et al. Myc regulates a transcriptional program that stimulates mitochondrial glutaminolysis and leads to glutamine addiction, Proc Natl Acad Sci USA 105(48):18782-18787 (2008).
Yang et al, Efficient Inhibition of Non-Small-Cell Lung Cancer Xenograft by Systemic Delivery of Plasmid-Encoding Short-Hairpin RNA Targeting VEGF, Cancer Biotherapy and Radiopharmaceuticals 25(1):65-73, 2010.
Yang, S. et al. Pancreatic cancers require autophagy for tumor growth, Genes Dev 25(7):717-729 (2011).
Ying, H. et al. Oncogenic Kras maintains pancreatic tumors through regulation of anabolic glucose metabolism, Cell 149(3):656-670 (2012)
Yu et al., RNA interference by expression of short-interfering RNAs and hairpin RNAs in mammalian cells, Proc. Natl. Acad. Sci. USA; 99(9):6047-6052 (2002).
Yuan, M., et al. A positive/negative ion-switching, targeted mass spectrometry-based metabolomics platform for bodily fluids, cells, and fresh and fixed tissue, Nat Protoc 7(5):872-881 (2012).

* cited by examiner

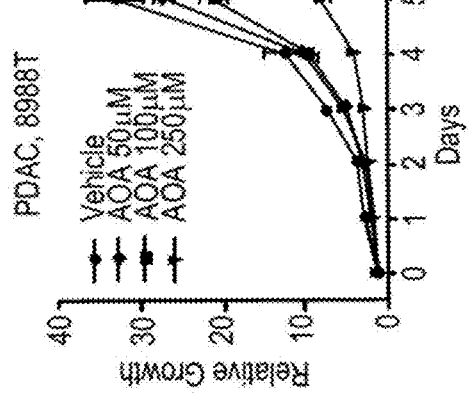
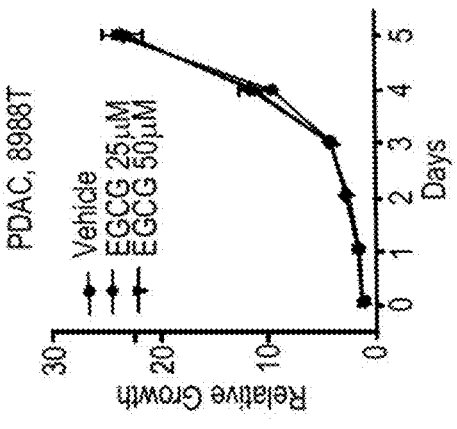
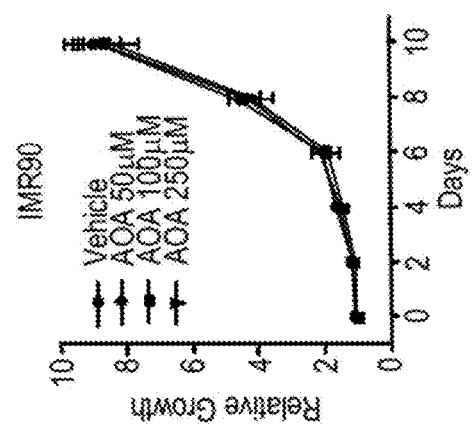
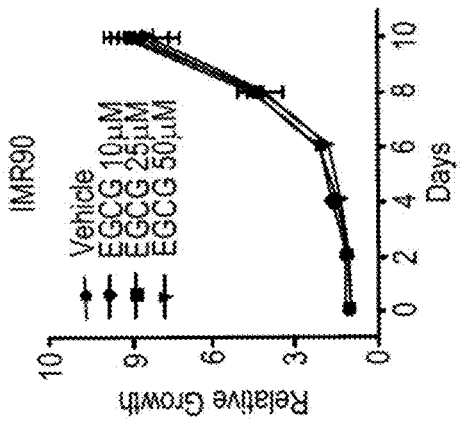
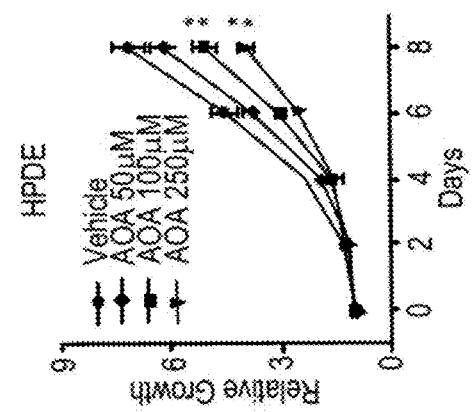
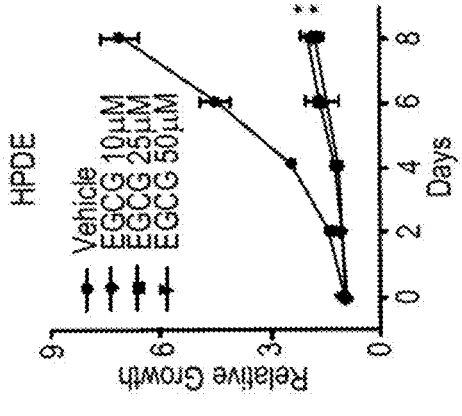
FIG. 30A
FIG. 30B

US 10,837,015 B2

TARGETING THE GLUTAMINE TO PYRUVATE PATHWAY FOR TREATMENT OF ONCOGENIC KRAS-ASSOCIATED CANCER

CROSS-REFERENCE TO RELATED APPLICATIONS

This application is a continuation of U.S. application Ser. No. 14/402,824, filed Nov. 21, 2014, now U.S. Pat. No. 10,138,479, issued on Nov. 27, 2018, which is the National Stage of International Application No. PCT/US2013/042468, filed on May 23, 2013, which claims the benefit of U.S. Provisional Patent Application No. 61/651,213, filed on May 24, 2012, each of which is incorporated by reference in their entirety.

STATEMENT REGARDING FEDERALLY SPONSORED RESEARCH OR DEVELOPMENT

This invention was made with government support under grant numbers P01CA117969, P01CA120964, and R01CA157490 awarded by The National Institutes of Health. The government has certain rights in the invention.

TECHNICAL FIELD

Methods and kits for targeting the glutamine to pyruvate pathway (GPP), e.g., for the treatment of oncogenic Kras-associated cancers, and methods for determining the efficacy of those methods are provided.

BACKGROUND

Oncogenic mutant Kras signaling drives uncontrolled proliferation and enhances survival of cancer cells through the activation of its downstream signaling pathways, such as the MAPK and PI3K-mTOR pathways. To meet the increased anabolic needs of enhanced proliferation, cancer cells require both sufficient energy and biosynthetic precursors as cellular building blocks to fuel cell growth. Under normal conditions, differentiated cells primarily metabolize glucose through the mitochondrial tricarboxylic acid (TCA) cycle to drive the production of ATP to sustain basic cellular functions. In cancer cells, metabolic pathways are rewired in order to divert nutrients, such as glucose and glutamine, into anabolic pathways to satisfy the demand for cellular building blocks. Accumulating evidence indicates that the reprogramming of tumor metabolism is under the control of various oncogenes and oncogenic signals. The Ras oncogene in particular has been shown to promote glycolysis. However, the mechanisms by which oncogenic Kras coordinates the shift in metabolism to sustain tumor growth, particularly in the tumor microenvironment, and whether specific metabolic pathways are essential for Kras-mediated tumor maintenance remain areas of active investigation.

Pancreatic ductal adenocarcinoma (PDAC) is among the most lethal cancers with a 5 year survival rate of 3%-5%. Malignant progression from pancreatic intraepithelial neoplasia (PanINs) to highly invasive and metastatic disease is accompanied by the early acquisition of activating mutations in the KRAS oncogene, which occurs in greater than 90% of cases, and subsequent loss of tumor suppressors including Ink4a/Arf, p53 and Smad4. The high mortality rate of PDAC can be attributed to several features; namely the advanced stage of presentation and its profound resistance to all forms of therapy, including conventional chemotherapy, targeted agents, and radiotherapy. Thus, there is a strong impetus to identify new therapeutic targets for this disease.

SUMMARY OF THE INVENTION

As follows from the Background section above, there remains a need in the art for methods for treating or preventing oncogenic Kras-associated cancers. Such methods, as well as other, related benefits, are presently provided, as discussed in detail below.

Cancer cells are characterized by metabolic dependencies that distinguish them from their normal counterparts and, in some cancers, glutamine (Gln) is used to fuel anabolic processes. The present disclosure describes the identification of a non-canonical pathway of Gln utilization in human pancreatic ductal adenocarcinoma (PDAC) cells that is required for tumor growth. While most cells utilize glutamate dehydrogenase (GLUD1), which converts Gln-derived glutamate into α-ketoglutarate in the mitochondria to fuel the tricarboxylic acid (TCA) cycle, it is presently discovered that PDAC rely on a distinct pathway (termed, herein, the "glutamine to pyruvate pathway" or "GPP") that is initiated with the conversion of Gln to aspartate followed by the conversion of Gln-derived aspartate into oxaloacetate (OAA) in the cytoplasm. Subsequently, this OAA is converted into malate, which enables the shuttling of NADH into the mitochondria for oxidative phosphorylation. The malate is then converted into pyruvate yielding cytosolic NADPH to maintain the cellular redox state. Importantly, PDAC cells are strongly dependent on this series of reactions, as Gln deprivation or genetic inhibition of any enzyme in this pathway led to an increase in reactive oxygen species and a reduction of reduced glutathione. Moreover, unlike normal pancreatic ductal cells, knockdown of any component enzyme in this series of reactions also results in a pronounced suppression of PDAC growth in vitro and in vivo. Furthermore, it is demonstrated herein that the reprogramming of Gln metabolism is mediated by oncogenic Kras, the signature genetic alteration in PDAC, via the transcriptional upregulation and repression of key metabolic enzymes in this pathway. The discovery of the essentiality of this pathway in PDAC and the fact that it is dispensable in normal cells thus provide novel therapeutic approaches to treat these refractory tumors as well as other oncogenic Kras-associated cancers.

Thus, in certain aspects, a method for determining the efficacy of GPP-targeting in a subject comprising an oncogenic Kras mutation (e.g., a subject with a cancer associated with an oncogenic Kras mutation), and the GPP-targeting comprises targeting an enzyme (e.g., Kras, GLS, GOT1, GOT2 and MDH1) or metabolite associated with an enzyme-catalyzed reaction in the GPP that is upstream of the malic enzyme (ME1)-catalyzed reaction (e.g., with an inhibitor, e.g., an anti-sense oligonucleotides, shRNA, siRNA, intrabodies, or small molecule, of an enzyme or metabolite associated with an enzyme-catalyzed reaction in the GPP), the method comprising: determining the level of one or more markers selected from the group consisting of NADP+, NADPH, GSSG, GSH, pyruvate, and reactive oxygen species (ROS) (e.g., hydrogen peroxide, super oxide, hydroxyl radical, hypochlorous acid, nitric oxide, peroxyl radical, and singlet oxygen), in a sample obtained from a subject who is undergoing or has undergone the GPP-targeting; and concluding that the GPP-targeting was effective if the level of one or more of the markers NADP+, GSSG and ROS is increased, relative to each marker's control level, or if the level of one or more of the markers NADPH, GSH and pyruvate is decreased, relative to each marker's control level; or concluding that the GPP-targeting was not effective if the level of one or more of the markers NADP+, GSSG, and ROS is not increased, relative to each marker's control level, or if the level of one or more of the markers NADPH, GSH and pyruvate is not decreased, relative to each marker's control level. In some aspects, the method comprises determining the level of two or more, three or more, four or more, five or more, or all of the markers selected from the group consisting of NADP+, NADPH, GSSG, GSH, pyruvate, and ROS.

Preferably, each marker's control level is the level of the marker in a sample obtained from the same subject prior to or at the beginning of the GPP-targeting or from another subject who is known to have a cancer associated with an oncogenic Kras mutation and is not undergoing or has not undergone GPP-targeting. The control level of the marker may also be a predetermined reference level of the marker.

In other aspects, the method for determining the efficacy of GPP-targeting further comprises determining the level of at least one additional marker selected from the group consisting of glutamine, glutamate, aspartate, αKG, NAD+, NADH, oxaloacetate, malate, MDH1, and ME1.

In one aspect, the GPP-targeting comprises inhibiting the enzyme GOT2, and the method comprises concluding that the GPP-targeting was effective if the level of one or more of the markers NADP+, GSSG and ROS is increased, relative to each marker's control level, or if the level of one or more of the markers NADPH, GSH, and pyruvate is decreased, relative to each marker's control level; and if the level of at least one of the markers selected from the group consisting NAD+ and NADH is altered (i.e., increased or decreased) relative to each marker's control level; or concluding that the GPP-targeting was not effective if the level of one or more of the markers NADP+, GSSG and ROS is not increased, relative to each marker's control level, or if the level of one or more of the markers NADPH, GSH, and pyruvate is not decreased, relative to each marker's control level; and if the level of at least one of the markers selected from the group consisting of NAD+ and NADH is not altered relative to each marker's control level.

In another aspect, the GPP-targeting comprises inhibiting the enzyme Kras, and the method comprises concluding that the GPP-targeting was effective if the level of one or more of the markers NADP+, GSSG and ROS is increased, relative to each marker's control level, or if the level of one or more of the markers NADPH, GSH, and pyruvate is decreased, relative to each marker's control level; and if the level of at least one of the markers selected from the group consisting of glutamine, oxaloacetate, and NAD+ is increased relative to its control level; or if the level of at least one of the markers selected from the group consisting of aspartate, αKG malate, MDH1, and ME1 is decreased relative to each marker's control level; or concluding that the GPP-targeting was not effective if the level of one or more of the markers NADP+, GSSG and ROS is not increased, relative to each marker's control level, or if the level of one or more of the markers NADPH, GSH, and pyruvate is not decreased, relative to each marker's control level; and if the level of at least one of the markers selected from the group consisting of glutamine, oxaloacetate, and NAD+ is not increased relative to its control level; or if the level of at least one of the markers selected from the group consisting of aspartate, αKG, malate, MDH1, and ME1 is not decreased relative to each marker's control level.

In yet another aspect, a method for determining the efficacy of oncogenic Kras inhibition in a subject comprising a cell having an oncogenic Kras mutation is provided, the method comprising: determining the expression level of at least one of the enzymes MDH1 and ME1 in a sample obtained from a subject who is undergoing or has undergone the oncogenic Kras inhibition; and concluding that the oncogenic Kras inhibition was effective if the expression level of the at least one enzyme is decreased compared to a control level of the enzyme; or concluding that the oncogenic Kras inhibition was not effective if the expression level of the at least one enzyme is not decreased compared to a control level of the enzyme.

In another aspect, the GPP-targeting comprises inhibiting the enzyme GOT1, and the method concluding that the GPP-targeting was effective if the level of one or more of the markers NADP+, GSSG and ROS is increased, relative to each marker's control level, or if the level of one or more of the markers NADPH, GSH, and pyruvate is decreased, relative to each marker's control level; and if the level of at least one of the markers selected from the group consisting of aspartate, αKG, and NAD+ is increased relative to each marker's control level; or if the level of at least one of the markers selected from the group consisting of oxaloacetate, malate, glutamate, and NADH is decreased relative to each marker's control level; or concluding that the GPP-targeting was not effective if the level of one or more of the markers NADP+, GSSG and ROS is not increased, relative to each marker's control level, or if the level of one or more of the markers NADPH, GSH, and pyruvate is not decreased, relative to each marker's control level; and if the level of at least one of the markers selected from the group consisting of aspartate, αKG, and NAD+ is not increased relative to each marker's control level; or if the level of at least one of the markers selected from the group consisting of oxaloacetate, malate, glutamate, and NADH is not decreased relative to each marker's control level.

In another aspect, the GPP-targeting comprises inhibiting the enzyme MDH1, and the method includes concluding that the GPP-targeting was effective if the level of one or more of the markers NADP+, GSSG and ROS is increased, relative to each marker's control level, or if the level of one or more of the markers NADPH, GSH, and pyruvate is decreased, relative to each marker's control level; and if the level of at least one of the markers selected from the group consisting of oxaloacetate and NAD+ is increased relative to each marker's control level; or if the level of at least one of the markers selected from the group consisting of malate and NADH is decreased relative to each marker's control level; or concluding that the GPP-targeting was not effective if the level of one or more of the markers NADP+, GSSG and ROS is not increased, relative to each marker's control level, or if the level of one or more of the markers NADPH, GSH, and pyruvate is not decreased, relative to each marker's control level; and if the level of at least one of the markers selected from the group consisting of oxaloacetate and NAD+ is not increased relative to each marker's control level; or if the level of at least one of the markers selected from the group consisting of malate and NADH is not decreased relative to each marker's control level.

In another aspect, the GPP-targeting comprises inhibiting the enzyme GLS, and the method comprises concluding that the GPP-targeting was effective if the level of one or more of the markers NADP+, GSSG and ROS is increased, relative to each marker's control level, or if the level of one or more of the markers NADPH, GSH, and pyruvate is decreased, relative to each marker's control level; and if the level of at least one of the markers selected from the group consisting of glutamine and NAD+ is increased relative to each marker's control level, or if the level of at least one of the markers selected from the group consisting of aspartate, oxaloacetate, malate, glutamate, and NADH is decreased relative to each marker's control level; or concluding that the GPP-targeting was not effective if the level of one or more of the markers NADP+, GSSG and ROS is not increased, relative to each marker's control level, or if the level of one or more of the markers NADPH, GSH, and pyruvate is not decreased, relative to each marker's control level; and if the level of at least one of the markers selected from the group consisting of glutamine and NAD+ is not increased relative to each marker's control level, or if the level of at least one of the markers selected from the group consisting of aspartate, oxaloacetate, malate, glutamate, and NADH is not decreased relative to each marker's control level.

In yet other aspects, a method for determining the efficacy of GPP-targeting in a subject comprising an oncogenic Kras mutation, and the GPP-targeting comprises targeting one or more of the enzymes catalyzing the conversion of glutamine to aspartate, the method comprising: determining the level of at least one marker selected from the group consisting of GSSG, GSH, aspartate, αKG, NADP+, NADPH, mitochondrial NAD+, mitochondrial NADH, pyruvate, oxaloacetate, and malate in a sample obtained from a subject who is undergoing or has undergone the GPP-targeting; and concluding that the GPP-targeting was effective if the level of one or more of the markers GSSG, GSH, aspartate, αKG, NADP+, NADPH, NAD+, NADH, pyruvate, oxaloacetate, and malate is altered relative to each marker's control level. Preferably the one or more of the enzymes catalyzing the conversion of glutamine to aspartate is selected from GLS and GOT2.

In another aspect, the method includes concluding that the GPP-targeting (e.g., with an inhibitor of GOT1 or MDH1) was not effective if the level of aspartate is not increased relative to a control level; or concluding that the GPP-targeting was effective if the level of aspartate is increased relative to a control level.

Also provided herein is a method for determining the efficacy of glutamine to pyruvate pathway (GPP)-targeting in a subject having an oncogenic Kras mutation, and the GPP-targeting comprises inhibiting GOT1, MDH1, or ME1, the method including: determining the level of aspartate in a sample obtained from a subject who is undergoing or has undergone the GPP-targeting; and concluding that the GPP-targeting was effective if the level of aspartate is increased relative to a control level; or concluding that the GPP-targeting was not effective if the level of aspartate is not increased relative to a control level.

In still other aspects, a method for treating cancer in a subject comprising a cancer cell expressing an oncogenic Kras mutation is provided, the method comprising administering to the subject a therapeutically effective amount of a composition comprising an inhibitor of the enzyme ME1. In certain aspects, the method further comprises administering a therapeutically effective amount of a composition comprising an inhibitor that targets an additional enzyme associated with an enzyme-catalyzed reaction in the GPP or that targets a metabolite associated with an enzyme-catalyzed reaction in the GPP. The additional enzyme may be selected from the group consisting of, e.g., Kras, GLS, GOT2, GOT1 and MDH1. In preferred aspects, the inhibitor of the metabolite targets a metabolite selected from the group consisting of glutamine, glutamate, aspartate, GSH, NADH, NADPH, oxaloacetate, and malate.

In another aspect, a method for treating cancer in a subject comprising a cancer cell expressing an oncogenic Kras mutation is provided, the method comprising administering to the subject: a therapeutically effective amount of an inhibitor of the enzyme GLS or GOT2; and a therapeutically effective amount of a composition comprising an inhibitor that targets an additional enzyme associated with an enzyme-catalyzed reaction of the GPP or that targets a metabolite associated with an enzyme-catalyzed reaction in the GPP. Preferably, the inhibitor of the additional enzyme or metabolite targets one or more of the enzymes selected from the group consisting of Kras, GOT1, MDH1, and ME1, or a metabolite selected from the group consisting of glutamine, glutamate, aspartate, GSH, NADH, NADPH, oxaloacetate, and malate.

In still other aspects, methods for preventing cancer in a subject comprising an oncogenic Kras mutation are provided. Preferably, the methods comprise administering to the subject a therapeutically effective amount of a composition comprising an inhibitor of the enzyme ME1. In certain aspects, the method further comprises administering a therapeutically effective amount of a composition comprising an inhibitor that targets an additional enzyme associated with an enzyme-catalyzed reaction of the GPP or that targets a metabolite associated with an enzyme-catalyzed reaction in the GPP. In preferred aspects, the additional enzyme is selected from the group consisting of Kras, GLS, GOT1 and MDH1.

In another aspect, a method for preventing cancer in a subject comprising an oncogenic Kras mutation is provided, wherein the method comprises administering to the subject a therapeutically effective amount of an inhibitor of the enzyme GLS or GOT2; and a therapeutically effective amount of a composition comprising an inhibitor that targets an additional enzyme associated with an enzyme-catalyzed reaction of the GPP or that targets a metabolite associated with an enzyme-catalyzed reaction in the GPP. Preferably, the inhibitor of the additional enzyme or metabolite targets one or more of the enzymes selected from the group consisting of Kras, GOT1, MDH1, and ME1, or a metabolite selected from the group consisting of glutamine, glutamate, aspartate, GSH, NADH, NADPH, oxaloacetate, and malate.

In certain aspects kits are provided for use in GPP-targeting, e.g., for the treatment of a cancer associated with an oncogenic Kras mutation. For example, a kit comprising an inhibitor of ME1 and one or more inhibitors of one or more of the enzymes selected from the group consisting of Kras, GOT2, GLS, GOT1, and MDH1 is provided. In another aspect, a kit comprising an inhibitor of GLS and one or more inhibitors of one or more of the enzymes selected from the group consisting of Kras, GOT2, ME1, GOT1, and MDH1 is provided. In yet another aspect, a kit comprising an inhibitor of at least one of the enzymes selected from the group consisting of Kras, ME1, GLS, GOT1, GOT2, and MDH1, and an inhibitor of one or more metabolites associated with an enzyme-catalyzed reaction in the GPP is provided. The above described kits may comprise an inhibitor of two or more metabolites associated with an enzyme-catalyzed reaction in the GPP. In certain aspects, the inhibitor(s) in the above-described kits can target a metabolite selected from the group consisting of glutamine, glutamate, aspartate, oxaloacetate, malate, pyruvate, NADH, NADPH, and GSH. Preferably, the kits further comprise instructions for using the kit for treating or preventing a cancer expressing an oncogenic Kras mutation.

Preferably, in any of the above embodiments, the subject has been previously determined or is simultaneously determined to comprise the oncogenic Kras mutation (e.g., an oncogenic Kras mutation associated with cancer). Further the oncogenic Kras mutation can be selected from the group consisting of Kras$^{G12D}$, Kras$^{G12V}$, Kras$^{G13D}$, Kras$^{G12C}$, Kras$^{Q61R}$, Kras$^{Q61L}$, Kras$^{Q61K}$, Kras$^{G12R}$, and Kras$^{G12C}$. Preferably, the cancer associated with an oncogenic Kras mutation is selected from the group consisting of pancreatic cancer, non-small cell lung cancer, colorectal cancer, and biliary cancer. Most preferably, the cancer is pancreatic cancer.

Unless otherwise defined, all technical and scientific terms used herein have the same meaning as commonly understood by one of ordinary skill in the art to which this invention pertains. In case of conflict, the present document, including definitions, will control.

All publications, patent applications, patents, and other references mentioned herein are incorporated by reference in their entirety. The materials, methods, and examples disclosed herein are illustrative only and not intended to be limiting.

The details of one or more embodiments of the invention are set forth in the accompanying drawings and the description below. Preferred methods and materials are described below, although methods and materials similar or equivalent to those described herein can also be used in the practice or testing of the present invention. Other features, objects, and advantages of the invention will be apparent from the description and drawings, and from the claims.

DESCRIPTION OF DRAWINGS

FIGS. 30A and 30B contain line graphs plotting the relative growth over time (days) of HPDE (non-transformed human pancreatic ductal epithelial cells), IMR90 (human diploid fibroblasts) and 8988T treated with the indicated concentrations of AOA (FIG. 30A) or EGCG (FIG. 30B) and assayed for proliferation; error bars represent s.d. of triplicate wells from a representative experiment; **, p<0.01.

DETAILED DESCRIPTION

Figure 1A:
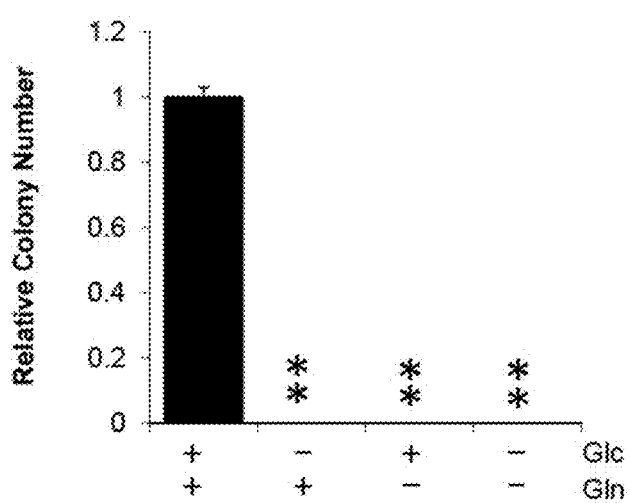
FIG. 1A contains a bar graph showing the relative colony number on the y-axis for each of the indicated groups of PDAC cultured in 10 cm tissue culture dishes in the presence (+) or absence (−) of glucose (Glc) and glutamine (Gln). Error bars represent standard deviations (s.d.; n=3); **, p<0.01.

Various aspects of the invention are described below.

I. Overview

During the process of tumorigenesis, genetic and epigenetic alterations fine-tune metabolism in cancer cells in a manner that optimizes their growth and survival in the tumor microenvironment. There has been a renewed interest in understanding the altered metabolism in cancer, and how such dependencies can be targeted for therapeutic gain. However, because normal cells may require the same metabolic pathways as cancer cells, achieving a successful therapeutic index remains a major challenge to the development of effective cancer therapies that target metabolic pathways. Oncogenic Kras reprograms PDAC metabolism to enhance glucose flux into anabolic pathways. In particular, oncogenic Kras promotes the diversion of glucose carbons into the non-oxidative arm of the pentose phosphate pathway (PPP) without changing glucose flux through the oxidative arm of the PPP. In doing so, oncogenic Kras signaling permits the non-oxidative PPP-mediated generation of ribose (for DNA/RNA biosynthesis) without affecting oxidative PPP-mediated redox control (NADP+:NADPH balance). This decoupling of ribose biogenesis from NADPH production suggests that PDAC cells rely on an alternative mechanism, independent of glucose metabolism through the PPP, to maintain cellular redox balance.

Recent evidence demonstrates that some cancer cells utilize glutamine (Gln) to support anabolic processes that fuel proliferation. However, the importance of Gln metabolism in pancreatic tumor maintenance is not known. It is demonstrated in the present Examples that PDAC cells, which are oncogenic Kras-associated cancer cells, depend on Gln for growth, as PDAC cells were profoundly sensitive to Gln deprivation. Moreover, the present Examples demonstrate that PDAC utilizes Gln to generate OAA via GOT1, and, sequentially, this OAA is converted into malate and then pyruvate, in a non-canonical pathway of glutamine metabolism, termed herein the "glutamine to pyruvate pathway (GPP)." This series of reactions results in the transport of NADH into the mitochondria (for oxidative phosphorylation), while simultaneously providing the reducing power necessary to sustain PDAC growth and survival through reducing equivalents generated by ME1 upon conversion of malate into pyruvate. Importantly, oncogenic Kras appears to support this pathway through the regulation of expression of key metabolic enzymes (GOT1 and GLUD1), and this reprogramming of Gln metabolism is indispensable for tumor maintenance in PDAC. The presently discovered GPP utilized by PDAC is summarized in the schematic diagram shown in FIG. 18. Moreover, since PDAC is an oncogenic Kras-associated cancer, other Kras-associated cancers, e.g., non-small cell lung cancer, colorectal cancer, and biliary cancer, are also expected to utilize the GPP.

Thus, based at least in part on the above-described discoveries, provided herein are methods for determining the efficacy of GPP-targeting (e.g., inhibition of an enzyme or metabolite in the GPP) in a subject (e.g., a subject with a cells (e.g., cancer cell) comprising an oncogenic Kras mutation. Also provided are methods for targeting the GPP, e.g. for the treatment or prevention of cancer, in a subject comprising an oncogenic Kras mutation, the method comprising administering to the subject a therapeutically effective amount of a composition comprising an inhibitor of an enzyme associated with an enzyme-catalyzed reaction in the GPP (e.g., GLS, GOT2, ME1, etc.). These embodiments and others are described in detail below.

II. Definitions

Figure 39:
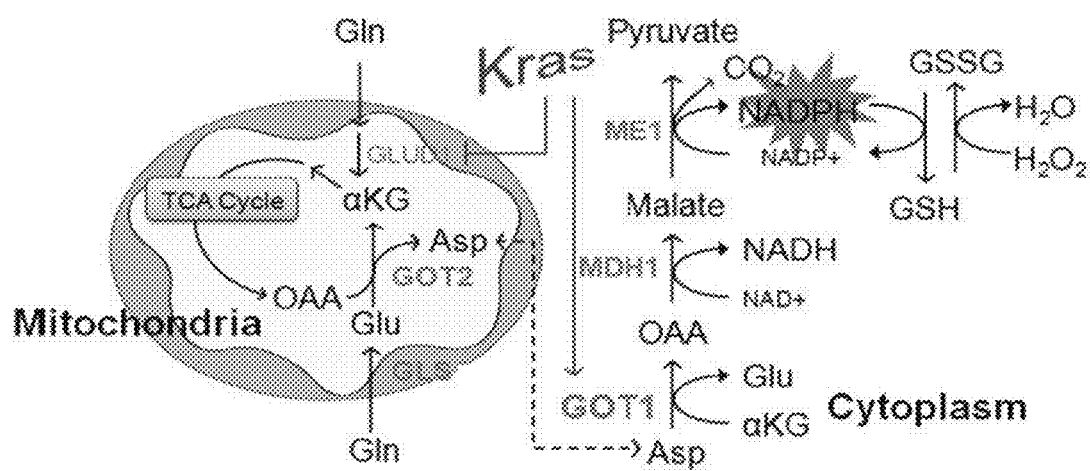
FIG. 39 is a schematic diagram modeling how Gln metabolic reprogramming in PDAC cells is mediated by oncogenic Kras to maintain cellular redox. The dashed line at the MDH1 step represents shuttling of reducing potential into the mitochondria. Solid-line arrows indicate enzymatic reactions; abbreviations are as follows: glutamine (Gln), aspartate (Asp), oxaloacetate (OAA), reduced glutathione (GSH), oxidized glutathione (GSSG), α-ketoglutarate (αKG), glutamate (Glu), tricarboxylic acid cycle (TCA cycle).

As used herein, the term "glutamine to pyruvate pathway (GPP)" means the presently discovered non-canonical pathway of glutamine metabolism depicted in FIG. 39, and as described in detail herein. Briefly, the GPP comprises GOT1, MDH1, and ME1, as well as GLS, GOT2 and other enzymes catalyzing the conversion of glutamate to aspartate, and involves the conversion of glutamine to glutamate, the conversion of glutamate to aspartate (Asp) catalyzed, e.g., by GOT2, the conversion of Asp to oxaloacetate (OAA) catalyzed by GOT1, the conversion of OAA to malate catalyzed by MDH1 and the conversion of malate to pyruvate catalyzed by ME1.

The term "metabolite," as used herein, means a substrate for or product of an enzymatic reaction of a metabolic pathway, e.g., glutamine metabolism, as described herein, or a cofactor or agent whose level is regulated by such an enzymatic reaction, and includes reactive oxygen species (ROS). Non-limiting examples of such metabolites include, e.g., NADP+, NADPH, GSSG, GSH, pyruvate, ROS (e.g., hydrogen peroxide, super oxide, hydroxyl radical, hypochlorous acid, nitric oxide, peroxyl radical, and singlet oxygen), glutamine, glutamate, aspartate, αKG, NAD+, NADH, oxaloacetate, and malate.

The enzymes and metabolites described herein are also in some contexts referred to as "markers," e.g., when their levels or activities are measured in order to determine the efficacy of GPP-targeting (e.g., for the treatment of a cancer associated with an oncogenic Kras mutation).

As used herein, the term "glutamine to pyruvate pathway-targeting" or "GPP-targeting" means a therapy (e.g., treatment of a subject, e.g., administration of a drug, e.g., an inhibitor or agonist, to the subject) that modulates (i.e., increases or decreases) the expression level or activity of one or more enzymes or metabolites that are "associated with an enzyme-catalyzed reaction in the GPP" (i.e., an enzyme that itself catalyzes a reaction (e.g., GLS, GOT2, GOT1, MDH1, ME1), or that modulates the expression or activity of another enzyme that catalyzes a reaction in the GPP (e.g., oncogenic Kras, which modulates the activity of GOT1 and modulates the expression of MDH1 and ME1) or an enzyme that modulates the level of a metabolite that is a substrate in the GPP; or, i.e., a metabolite that serves as a substrate for or is a product of an enzyme catalyzed reaction in the GPP (e.g., glutamine (Gln), glutamate (Glu), Asp, OAA, malate, αKG, NADH (e.g., mitochondrial or cytoplasmic NADH), NAD+(e.g., mitochondrial or cytoplasmic NAD+), NADP+, NADPH, cellular reduced glutathione (GSG), oxidized glutathione (GSSG), and pyruvate). GPP-targeting can include a cancer therapy, and preferably, includes a therapy for a cancer associated with an oncogenic Kras mutation, e.g., pancreatic cancer.

As used herein, "targeting an enzyme or metabolite associated with an enzyme-catalyzed reaction in the GPP that is upstream of the malic enzyme (ME1)-catalyzed reaction" means that the therapy (i.e., GPP-targeting) modulates the expression level or activity of an enzyme or metabolite that is associated with an enzyme-catalyzed reaction in the GPP before the step in the pathway in which ME1 catalyzes the conversion of malate to pyruvate. Thus, ME1 itself is not a target in a therapy that has a target upstream of ME1, and, e.g., pyruvate, NADP+, NADPH, GSH, GSSG, and ROS which are metabolites that are associated with an enzyme-catalyzed conversion of malate to pyruvate by ME1 are not encompassed by a therapy that has a target upstream of ME1.

As used herein, the terms "Kras-associated cancer" and "cancer associated with an oncogenic Kras mutation" mean a cancer in which the initiation and/or maintenance are/is dependent, at least in part, on an activating mutation in a Kras gene. Typically, an "activating mutation" is one which leads to constitutive activation of the Kras gene and protein expression of the oncogenic Kras. Non-limiting examples of activating mutations in the Kras gene include, e.g., $Kras^{G12D}$, $Kras^{G12V}$, $Kras^{G13D}$, $Kras^{G12C}$, $Kras^{Q61R}$, $Kras^{Q61L}$, $Kras^{Q61K}$, $Kras^{G12R}$, and $Kras^{G12C}$. Non-limiting examples of a Kras-associated cancer include human pancreatic ductal adenocarcinoma (PDAC), non-small cell lung cancer, colorectal cancer, and biliary cancer.

As used herein, the term "subject" means any animal, including any mammal, and, in particular, a human. As used herein, a "subject comprising an oncogenic Kras mutation" comprises at least one cell that contains an oncogenic Kras mutation, as described above. As used herein, a "subject with cancer associated with an oncogenic Kras mutation" comprises at least one cancer cell (e.g., tumor cell) (e.g. pancreatic cancer) that contains an oncogenic Kras mutation, as described above. In certain embodiments, the subject having such cancer may or may not exhibit other clinical signs of cancer, and may or may not have been diagnosed with the cancer (e.g. by an attending physician). As used herein a "subject comprising an oncogenic Kras mutation" comprises at least one cell comprising the oncogenic Kras mutation; however, the subject may or may not have been diagnosed with cancer, and may or may not have cancer.

As used herein, the term "sample" includes any suitable specimen obtained from a subject that includes at least one cell having an oncogenic Kras mutation. Non-limiting examples of suitable specimens include, e.g., tumor tissue (e.g., from a biopsy), lymphoid (e.g., lymph node) tissue, fluid from a cyst, and body fluid such as blood or urine. Where tumor cell containing tissue is used, as appropriate, histological sections of tumors or cancer cell-containing tissue, whole or soluble fractions of tissue or cell (e.g., cancer cell) lysates, cell subfractions (e.g., mitochondrial or nuclear subfractions), whole or soluble fractions of tissue or cell (e.g., cancer cell) subfraction lysates can be analyzed.

As used herein, a "a control level of a marker" is the level of the marker in a sample obtained from the same subject prior to or at the beginning of the GPP-targeting or from another subject or subjects who is/are known to have a cancer associated with an oncogenic Kras mutation (e.g., $Kras^{G12D}$), and is not undergoing or has not undergone GPP-targeting, and preferably, although not necessarily, any other cancer therapies. In certain embodiments, the control level may be a "predetermined reference level" (i.e., standard) to which the level of the marker in the sample from a subject who is undergoing or has undergone the GPP-targeting is compared. It is understood, that any such "control level" can be a mean level obtained from a plurality of the subjects referred to above.

As used herein, "treating" or "treatment" of a state, disorder or condition includes: (1) Preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "treating cancer" means causing a partial or complete decrease in the rate of growth of a tumor, and/or in the size of the tumor and/or in the rate of local or distant tumor metastasis in the presence of an inhibitor of the invention, and/or any decrease in tumor survival.

As used herein, the term "preventing a disease" (e.g., preventing cancer associated with an oncogenic Kras mutation) in a subject means for example, to stop the development of one or more symptoms of a disease in a subject before they occur or are detectable, e.g., by the patient or the patient's doctor. Preferably, the disease (e.g., cancer) does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

As used herein "combination therapy" means the treatment of a subject in need of treatment with a certain composition or drug in which the subject is treated or given one or more other compositions or drugs for the disease in conjunction with the first and/or in conjunction with one or more other therapies, such as, e.g., a cancer therapy such as chemotherapy, radiation therapy, and/or surgery. Such combination therapy can be sequential therapy wherein the patient is treated first with one treatment modality (e.g., drug or therapy), and then the other (e.g., drug or therapy), and so on, or all drugs and/or therapies can be administered simultaneously. In either case, these drugs and/or therapies are said to be "coadministered." It is to be understood that "coadministered" does not necessarily mean that the drugs and/or therapies are administered in a combined form (i.e., they may be administered separately or together to the same or different sites at the same or different times).

The term "pharmaceutically acceptable derivative" as used herein means any pharmaceutically acceptable salt, solvate or prodrug, e.g., ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

As used herein the terms "therapeutically effective" and "effective amount", used interchangeably, applied to a dose or amount refers to a quantity of a composition, compound or pharmaceutical formulation that is sufficient to result in a desired activity upon administration to an animal in need thereof. Within the context of the present invention, the term "therapeutically effective" refers to that quantity of a composition, compound or pharmaceutical formulation that is sufficient to reduce or eliminate at least one symptom of a disease or condition specified herein. When a combination of active ingredients is administered, the effective amount of the combination may or may not include amounts of each ingredient that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level.

Therapeutically effective dosages can be determined stepwise by combinations of approaches such as (i) characterization of effective doses of the composition or compound in in vitro cell culture assays using tumor cell growth and/or survival as a readout followed by (ii) characterization in animal studies using tumor growth inhibition and/or animal survival as a readout, followed by (iii) characterization in human trials using enhanced tumor growth inhibition and/or enhanced cancer survival rates as a readout.

The term "nucleic acid hybridization" refers to the pairing of complementary strands of nucleic acids. The mechanism of pairing involves hydrogen bonding, which may be Watson-Crick, Hoogsteen or reversed Hoogsteen hydrogen bonding, between complementary nucleoside or nucleotide bases (nucleobases) of the strands of nucleic acids. For example, adenine and thymine are complementary nucleobases that pair through the formation of hydrogen bonds. Hybridization can occur under varying circumstances. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS (where 1×SSC is 0.15 M NaCl, 0.15 M Na citrate) at 68° C. or for oligonucleotide (oligo) inhibitors washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos).

Conditions of intermediate or moderate stringency (such as, for example, an aqueous solution of 2×SSC at 65° C.; alternatively, for example, hybridization to filter-bound DNA in 0.5 M NaHPO4, 7% SDS, 1 mM EDTA at 65° C. followed by washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA or RNA molecule and length and base composition of the probe, and are normally determined empirically in preliminary experiments, which are routine (see Southern, J. Mol. Biol. 1975; 98:503; Sambrook et al., Molecular Cloning: A Laboratory Manual, 2nd ed., vol. 2, ch. 9.50, CSH Laboratory Press, 1989; Ausubel et al. (eds.), 1989, Current Protocols in Molecular Biology, Vol. 1, Green Publishing Associates, Inc., and John Wiley & Sons, Inc., New York, at p. 2.10.3). An extensive guide to the hybridization of nucleic acids is found in, e.g., Tijssen (1993) Laboratory Techniques in Biochemistry and Molecular Biology—Hybridization with Nucleic Acid Probes part I, chapt 2, "Overview of principles of hybridization and the strategy of nucleic acid probe assays," Elsevier, N.Y. ("Tijssen").

As used herein, the term "standard hybridization conditions" refers to hybridization conditions that allow hybridization of two nucleotide molecules having at least 50% sequence identity. According to a specific embodiment, hybridization conditions of higher stringency may be used to allow hybridization of only sequences having at least 75% sequence identity, at least 80% sequence identity, at least 90% sequence identity, at least 95% sequence identity, or at least 99% sequence identity.

As used herein, the phrase "under hybridization conditions" means conditions under conditions that facilitate specific hybridization of a subset of capture oligonucleotides to complementary sequences present in the cDNA or cRNA. The terms "hybridizing specifically to" and "specific hybridization" and "selectively hybridize to," as used herein refer to the binding, duplexing, or hybridizing of a nucleic acid molecule preferentially to a particular nucleotide sequence under at least moderately stringent conditions, and preferably, highly stringent conditions, as discussed above.

"Polypeptide" and "protein" are used interchangeably and mean any peptide-linked chain of amino acids, regardless of length or post-translational modification.

As used herein, the term "nucleic acid" or "oligonucleotide" refers to a deoxyribonucleotide or ribonucleotide in either single- or double-stranded form. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methyl-phosphonate and phosphodiester linkages (Strauss-Soukup (1997) Biochemistry 36:8692-8698), and benzylphosphonate linkages (Samstag (1996) Antisense Nucleic Acid Drug Dev 6:153-156). The term nucleic acid is used interchangeably with cDNA, cRNA, mRNA, oligonucleotide, probe and amplification product.

Some of the abbreviations used in the present disclosure are as follows: Gln: glutamine; Glu: glutamate; Glc: glucose; Asp: aspartate; OAA: oxaloacetate; αKG: α-ketoglutarate; ROS: reactive oxygen species; NAD+: nicotinamide adenine dinucleotide; NADH: reduced nicotinamide adenine dinucleotide; NADP+: nicotinamide adenine dinucleotide phosphate; NADPH: reduced nicotinamide adenine dinucleotide phosphate; GSSG: glutathione disulfide; GSH: reduced glutathione; GLS: glutaminase; GOT: glutamic-oxaloacetic transaminase; MDH: malate dehydrogenase; ME: malic enzyme.

III. Oncogenic Kras

The human Kras gene sequence has two preferred transcript variants, having the nucleic acid sequences given in GenBank Accession Nos. NM_033360 (transcript variant a) (SEQ ID NO: 1) and NM_004985.3 (transcript variant b) (SEQ ID NO: 2). The human Kras protein sequence has two preferred variants, having the amino acid sequence given in GenBank Accession Nos. NP_203524 (isoform a) (SEQ ID NO: 3) and NP_004976.2 (isoform b) (SEQ ID NO: 4). The numbering of Kras amino acid mutations (e.g., $Kras^{G12D}$, $Kras^{G61R}$, etc., corresponds to either of the above-given amino acid sequences.

Oncogenic Kras mutations associated with cancer include, without limitation, $Kras^{G12D}$, $Kras^{G12V}$, $Kras^{G13D}$, $Kras^{G12C}$, $Kras^{Q61R}$, $Kras^{Q61L}$, $Kras^{Q61K}$, $Kras^{G12R}$, and $Kras^{G12C}$. The skilled artisan will understand that a Kras gene comprising a different Kras mutation than one of those above and/or combinations of the above and/or other Kras mutations that lead to and/or do not prevent activation, and preferably constitutive activation of Kras, is also an oncogenic Kras encompassed by the present invention. In a preferred embodiment, an oncogenic Kras is $Kras^{G12D}$.

The presence of an oncogenic Kras mutation in a sample, e.g., from a cell, tumor biopsy, or other DNA, RNA or protein-containing sample can be determined at the genomic, RNA or protein level according to any suitable method known in the art.

For example, Southern blotting can be used to determine the presence of an oncogenic Kras mutation in a genome. Methods for Southern blotting are known to those of skill in the art (see, e.g., Current Protocols in Molecular Biology, Chapter 19, Ausubel, et al., Eds., Greene Publishing and Wiley-Interscience, New York, 1995, or Sambrook et al., Molecular Cloning: A Laboratory Manual, 2d Ed. vol. 1-3, Cold Spring Harbor Press, N Y, 1989). In such an assay, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., genomic DNA from the same or related cell, tissue, organ, etc.) provides an estimate of the relative copy number of the target nucleic acid.

Amplification-based assays, such as PCR, can also be used to determine the presence of an oncogenic Kras mutation in a genome, as well as the mRNA expression of an oncogenic Kras in an RNA-containing sample. Detailed protocols for quantitative PCR are provided, for example, in Innis et al. (1990) PCR Protocols, A Guide to Methods and Applications, Academic Press, Inc. N.Y. Real-time PCR can also be used (see, e.g., Gibson et al., Genome Research 6:995-1001, 1996; Heid et al., Genome Research 6:986-994, 1996). Real-time PCR evaluates the level of PCR product accumulation during amplification. Total genomic DNA (or RNA) is isolated from a sample. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.). To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from $10-10^6$ copies of the gene of interest are generally sufficient. In addition, a standard curve is generated for the control sequence. This permits standardization of initial content of the nucleic acid of interest in a tissue sample to the amount of control for comparison purposes. Methods of real-time quantitative PCR ("QPCR") using TaqMan probes are well known in the art. Detailed protocols for QPCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994.

Other suitable amplification methods include, but are not limited to ligase chain reaction (LCR) (see Wu and Wallace (1989) Genomics 4:560, Landegren et al. (1988) Science 241:1077, and Barringer et al. (1990) Gene 89:117), transcription amplification (Kwoh et al. (1989) Proc. Natl. Acad. Sci. USA 86:1173), self-sustained sequence replication (Guatelli et al. (1990) Proc. Nat. Acad. Sci. USA 87:1874), dot PCR, and linker adapter PCR, etc. In another embodiment, DNA sequencing may be used to determine the presence of an oncogenic Kras mutation in a genome. Methods for DNA sequencing are known to those of skill in the art.

IV. Enzymes Associated with the GPP

As described above, and as shown in FIG. 39, in addition to Kras, the enzymes GLS, GOT1, GOT2, MDH1, and ME1 are presently demonstrated to be associated with an enzyme-catalyzed reaction in the GPP. Specifically, the GPP is shown to involve the conversion of Gln to Glu, catalyzed by GLS; the conversion of Glu to Asp, catalyzed, e.g., by GOT2; the conversion of Asp to OAA, catalyzed by GOT1; the conversion of OAA to malate, catalyzed by MDH1; and the conversion of malate to pyruvate, catalyzed by ME1. Furthermore, the reaction catalyzed by GOT1 also reduces αKG to Glu, the reaction catalyzed by MDH1 also oxidizes NADH to NAD+, which is then shuttled to the mitochondria and reduced to NADH, and the reaction catalyzed by ME1 also reduces NADP+ to NADPH, which further results in the reduction of GSSH to GSH and the reduction in levels of ROS. It will be understood that Gls, GOT2, other enzymes involved in conversion of glutamate to aspartate, GOT1, MDH1, and ME1 are enzymes in the GPP and that all the enzymes in the GPP and, for example, Kras and GLUD1 are enzymes associated with the GPP.

The nucleic acid and amino acid sequences for the enzymes GLS. GOT1, GOT2, MDH1, and ME1 presently discovered to be associated with the GPP are known and have been described. GenBank® Accession Nos. of exemplary nucleic acid and amino acid sequences for the human enzymes are provided in Table 1, below.

TABLE 1

Exemplary GenBank ® Accession Numbers for Enzymes Associated with GPP

| Gene Name | Nucleic Acid GenBank ® Accession No. | SEQ ID NO | Corresponding Polypeptide Name | Amino Acid GenBank ® Accession No. | SEQ ID NO |
|---|---|---|---|---|---|
| glutaminase (GLS), nuclear gene encoding mitochondrial protein, transcript variant 2 | NM_001256310 | 5 | glutaminase kidney isoform, mitochondrial isoform 2 (GLS) | NP_001243239 | 6 |
| glutamic-oxaloacetic transaminase 2, mitochondrial (aspartate aminotransferase 2) (GOT2), nuclear gene encoding mitochondrial protein | NM_002080 | 7 | aspartate aminotransferase, mitochondrial precursor (GOT2) | NP_002071 | 8 |
| glutamic-oxaloacetic transaminase 1, soluble (aspartate aminotransferase 1) (GOT1) | NM_002079 | 9 | aspartate aminotransferase, cytoplasmic (GOT1) | NP_002070 | 10 |
| malate dehydrogenase 1, NAD (soluble) (MDH1), transcript variant 1 | NM_001199111 | 11 | malate dehydrogenase, cytoplasmic isoform 1 (MDH1) | NP_001186040 | 12 |
| malate dehydrogenase 1, NAD (soluble) (MDH1), transcript variant 2 | NM_005917 | 13 | malate dehydrogenase, cytoplasmic (MDH1), isoform 2 | NP_005908 | 14 |

TABLE 1-continued

Exemplary GenBank® Accession Numbers for Enzymes Associated with GPP

| Gene Name | Nucleic Acid GenBank® Accession No. | SEQ ID NO | Corresponding Polypeptide Name | Amino Acid GenBank® Accession No. | SEQ ID NO |
|---|---|---|---|---|---|
| malate dehydrogenase 1, NAD (soluble) (MDH1), transcript variant 3 | NM_001199112 | 15 | malate dehydrogenase, cytoplasmic (MDH1), isoform 3 | NP_001186041 | 16 |
| malic enzyme 1, NADP(+)-dependent, cytosolic (ME1) | NM_002395 | 17 | NADP-dependent malic enzyme | NP_002386 | 18 |

In certain embodiments, it is desirable to determine (e.g., assay, measure, approximate) the level (e.g., expression or activity) of an enzyme associated with an enzyme-catalyzed reaction in the GPP. The expression level of such an enzyme may be determined according to any suitable method known in the art. A non-limiting example of such a method includes PCR, e.g., real-time quantitative PCR (QPCR), as described in detail above, which measures the expression level of the mRNA encoding the polypeptide. mRNA expression can also be determined using microarray (transcriptomic analysis), methods for which are well known in the art (see, e.g., Watson et al. Curr Opin Biotechnol (1998) 9: 609-14). For example, mRNA expression profiling can be performed to identify differentially expressed genes, wherein the raw intensities determined by microarray are log 2-transformed and quantile normalized and gene set enrichment analysis (GSEA) is performed according, e.g., to Subramanian et al. (2005) Proc Natl Acad Sci USA 102:15545-15550).

Other examples of suitable methods include Western blot, ELISA and/or immunohistochemistry, which can be used to measure protein expression level. Such methods are well known in the art.

Methods for assaying the activity of an enzyme of the present invention include functional in vitro assays and are well known in the art. For example, and without limitation, the activity of virtually any enzyme can be traced using isotopically labeled molecules and standards (e.g. by MS, HPLC, NMR). More straightforward methods rely on coupling the activity of a desired enzyme to those with a readily observable readout (like NAD/NADH, NADP+/NADPH, ROS (e.g., total ROS), GSSG/GSH (e.g., levels of GSH), etc.). Examples of such assays are described, for example, in Harris and Keshwani (2009), *Methods in Enzymology; Guide to Protein Purification, 2nd Edition;* 463:57-71; Rossomando, E. F. (1990) *Methods in Enzymology; Guide to Protein Purification. 2nd Edition;* 182:38-49; Crutchfield et al. (2010) *Methods in Enzymology; Guide to Protein Purification, 2nd Edition;* 470:393-426; Befroy et al. (2009) *Methods in Enzymology; Guide to Protein Purification. 2nd Edition;* 457:373-393; and Bartlett and Causey (1988) *Methods in Enzymology; Guide to Protein Purification. 2nd Edition;* 166:79-92.

V. Metabolites of the Invention

Non-limiting examples of metabolites associated with an enzyme-catalyzed reaction in the GPP include, e.g., NADP+, NADPH, GSSG, GSH, pyruvate, ROS (e.g., hydrogen peroxide, super oxide, hydroxyl radical, hypochlorous acid, nitric oxide, peroxyl radical, and singlet oxygen), glutamine, glutamate, aspartate, αKG, NAD+, NADH, oxaloacetate, and malate. Such metabolites are described, e.g., in Berg, J. M. et al. Biochemistry (Textbook) ISBN-10: 0716787245|ISBN-13: 978-0716787242|Publication Date: May 19, 2006| Edition: Sixth Edition.

In certain embodiments, it is desirable to measure the levels of one or more such metabolites in a sample. Metabolite levels may be measured according to any suitable method known in the art. For example, metabolite levels may be measured using targeted liquid-chromatography mass spectrometry (LC/MS/MS). For example, for metabolite collection from cultured cells (at, e.g., ~70% confluence) is fully aspirated and 4 mL of 80% (v/v) methanol is added at dry ice temperatures. Cells and the metabolite-containing supernatants are collected into conical tubes. Insoluble material in lysates are centrifuged at 2,000×g for 15 min, and the resulting supernatant is evaporated using a refrigerated speed vac. Subsequent metabolite analysis is performed as described before (see, Locasale et al. (2011) Nature Genetics; 43:869-874). Peak areas from the total ion current for each metabolite multiple reaction monitoring (MRM) transition are integrated using MultiQuant v1.1 software (Applied Biosystems). Data analysis was performed in Cluster3.0 and TreeViewer. Such methods are also described in detail in U.S. provisional application No. 61/578,116. The skilled artisan will appreciate that nuclear magnetic resonance (NMR) can also be used to measure the level metabolites as well. Such methods are well known in the art and are described in detail, e.g., in Wishart D S. (2011) *Bioanalysis*; August; 3(15): 1769-82.

ROS can be measured as described in the Examples, e.g., using 2',7'-dichlorodihydrofluorescein diacetate (DCFDA, Invitrogen). Oxidation of DCFDA to the highly fluorescent 2',7'-dichloro-fluorescein (DCF) is detectable (e.g., by flow cytometry) and is proportionate to ROS generation.

The skilled artisan will understand, however, that other methods are known in the art and may be used for measuring the levels of metabolites in a sample.

VI. Methods of Treatment and Prevention

Methods for treating or preventing an oncogenic Kras-associated cancer in a subject comprising targeting the GPP are provided. A subject undergoing GPP-targeting may be a subject with a cancer associated with an oncogenic Kras mutation (e.g., pancreatic cancer, non-small cell lung cancer, colorectal cancer, biliary cancer). However, in other embodiments, the subject undergoing GPP-targeting may not have been diagnosed with cancer and may or may not have cancer. Such a subject may have undergone or may be undergoing GPP-targeting for another reason or other reasons, such as, but not limited to, for the prevention of a cancer associated with an oncogenic Kras mutations. Such patient may have been, e.g., determined, e.g., by the subject's physician, to comprise an oncogenic Kras mutation (e.g., $Kras^{G12D}$, $Kras^{G12V}$, $Kras^{G13D}$, $Kras^{G12C}$, $Kras^{Q61R}$, $Kras^{Q61L}$, $Kras^{Q61K}$, $Kras^{G12R}$, or $Kras^{G12C}$), and, as such, e.g., at risk of developing a cancer associated with the Kras mutation. While not intending to be bound by any one particular theory or mechanism, as demonstrated herein, oncogenic Kras increases the expression of GOT1, and decreases the expression of GLUD1, thereby driving the non-canonical pathway of glutamine metabolism described herein (i.e., the GPP); thus, a person having an oncogenic Kras mutation, but not necessarily having been diagnosed with cancer, can benefit from receiving GPP-targeting, e.g., as a prophylactic treatment (e.g., delaying or preventing the onset of cancer).

Cancers associated with an oncogenic Kras mutation that may be treated or prevented according to the present methods, include, e.g., pancreatic cancer, non-small cell lung cancer, colorectal cancer, and biliary cancer. However, the skilled artisan will understand that any cancer that is associated with an oncogenic Kras mutation is encompassed by the present methods and kits pertaining thereto.

In certain embodiments, the method for treatment or prevention comprises administering to a subject comprising an oncogenic Kras mutation (e.g., a subject with an oncogenic Kras-associated cancer or at risk of developing such cancer (e.g., a subject comprising an oncogenic Kras mutation)) a therapeutically effective amount of a composition comprising an inhibitor that targets at least one enzyme or metabolite associated with an enzyme-catalyzed reaction in the GPP.

In other embodiments, the treatment method can comprise inhibiting a plurality (e.g., 2 or more, 3 or more, 4 or more, 5 or more, 6 or more, 7 or more, 8 or more, 9 or more, etc.) enzymes and/or metabolites associated with an enzyme-catalyzed reaction in the GPP (e.g., in a combination therapy).

The enzymes and metabolites that can be inhibited, or in certain cases, treated with an agonist to increase activity or expression level, include, but are not limited to, the enzymes GLS, GOT2, GOT1, MDH1, ME1, Kras, and GLUD1, and the metabolites NADP+, NADPH, GSSG, GSH, pyruvate, glutamine, glutamate, aspartate, αKG, NAD+, NADH, oxaloacetate, and malate. Further, ROS levels may be increased, e.g., by administration of inhibitors of anti-oxidants. Non-limiting examples of anti-oxidant inhibitors include, e.g., aminotriazole, chlorodonitrobenzene, mercaptosuccinate, and gemcitabine.

Thus, in certain embodiments, an inhibitor or any combination of 2 or more inhibitors of the above-described enzymes and metabolites associated with an enzyme-catalyzed reaction in the GPP can be administered in a combination therapy to a subject comprising an oncogenic Kras mutation in order to target the GPP (e.g., for the treatment of cancer).

In a preferred embodiment, the method of treatment comprises administering to a subject comprising an oncogenic Kras mutation an inhibitor of the enzyme ME1. In other embodiments, an inhibitor of ME1 is administered in a combination therapy with at least one additional inhibitor, or in certain cases, agonist (e.g., of GLUD1), of an enzyme or metabolite associated with an enzyme-catalyzed reaction in the GPP. For example an inhibitor of ME1 can be administered to a subject comprising an oncogenic Kras mutation in a combination therapy with at least one inhibitor of an enzyme selected from GLS, GOT2, GOT1, MDH1, and Kras, and/or an agonist of GLUD1, and/or an inhibitor of at least one metabolite selected from NADP+, NADPH, GSSG, GSH, pyruvate, glutamine, glutamate, aspartate, αKG, NAD+, NADH, oxaloacetate, and malate.

In another preferred embodiment, the method of treatment comprises administering to a subject comprising an oncogenic Kras mutation an inhibitor of the enzyme GLS. In other embodiments, an inhibitor of GLS is administered in a combination therapy with at least one additional inhibitor, or in certain cases, agonist (e.g., of GLUD1), of an enzyme or metabolite associated with an enzyme-catalyzed reaction in the GPP. For example an inhibitor of GLS can be administered to a subject comprising an oncogenic Kras mutation in a combination therapy with at least one inhibitor of an enzyme selected from GOT2, GOT1, MDH1, ME1, Kras, and/or an agonist of GLUD1, and/or an inhibitor of at least one metabolite selected from NADP+, NADPH, GSSG, GSH, pyruvate, glutamine, glutamate, aspartate, αKG, NAD+, NADH, oxaloacetate, and malate.

In another preferred embodiment, the method of treatment comprises administering to a subject comprising an oncogenic Kras mutation an inhibitor of the enzyme GOT2. In other embodiments, an inhibitor of GOT2 is administered in a combination therapy with at least one additional inhibitor, or in certain cases, agonist (e.g., of GLUD1), of an enzyme or metabolite associated with an enzyme-catalyzed reaction in the GPP. For example an inhibitor of GOT2 can be administered to a subject comprising an oncogenic Kras mutation in a combination therapy with at least one inhibitor of an enzyme selected from GLS, GOT1, MDH1, ME1, Kras, and/or an agonist of GLUD1 and/or an inhibitor of at least one metabolite selected from NADP+, NADPH, GSSG, GSH, pyruvate, glutamine, glutamate, aspartate, αKG, NAD+, NADH, oxaloacetate, and malate.

Non-limiting examples of inhibitors are selected from the group consisting of anti-sense oligonucleotides, small hairpin RNA (shRNA), small inhibiting RNA (siRNA), intrabodies, aptamers, and small molecule, as described in detail in Section VIII, below.

The skilled artisan will appreciate that other combinations of inhibitors and/or agonists are possible, so long as the combination results in the inhibition of the GPP. Methods for determining the efficacy of GPP-targeting (e.g., inhibition) are described in detail in the following section.

The skilled artisan will also appreciate that the GPP-targeting described herein, e.g. for the treatment of a cancer associated with an oncogenic Kras mutation, may also be administered in a combination therapy with other treatments, e.g. other cancer therapies. Non-limiting examples of such cancer therapies include chemotherapy, radiation therapy, antiangiogenic therapy, surgery, and combinations thereof.

In a preferred embodiment, GPP-targeting is administered to a subject with a cancer associated with an oncogenic Kras mutation in a combination therapy with a treatment that increases ROS. While not intending to be limited to any one particular theory or mechanism of action, the present Examples demonstrate that PDAC drive glutamine into the GPP, thereby reducing the levels of ROS; accordingly, increasing ROS levels can be beneficial for reducing cancer cell growth. Moreover, certain cancer therapies are known to increase ROS levels, such as, but not limited to, radiation therapy, as well as autophagy inhibitors such as hydroxychloroquine and chloroquine, and anti-oxidant inhibitors such as aminotriazole, chlorodonitrobenzene, mercaptosuccinate, and gemcitabine. Thus, in certain embodiments, the GPP-targeting (e.g., administration of an inhibitor, or in certain cases, agonist, of at least one enzyme or metabolite associated with an enzyme-catalyzed reaction in the GPP) in a subject is administered in a combination therapy with a radiation therapy, and/or one or more autophagy inhibitors (e.g., hydroxychloroquine, chloroquine), and/or one or more anti-oxidant inhibitors (e.g., aminotriazole, chlorodonitrobenzene, mercaptosuccinate, and gemcitabine).

Chemotherapeutic agents, include for example: taxanes such as taxol, taxotere or their analogues; alkylating agents such as cyclophosphamide, isosfamide, melphalan, hexamethylmelamine, thiotepa or dacarbazine; antimetabolites such as pyrimidine analogues, for instance 5-fluorouracil, cytarabine, capecitabine, and gemcitabine or its analogues such as 2-fluorodeoxycytidine; folic acid analogues such as methotrexate, idatrexate or trimetrexate; spindle poisons including vinca alkaloids such as vinblastine, vincristine, vinorelbine and vindesine, or their synthetic analogues such as navelbine, or estramustine and a taxoid; platinum compounds such as cisplatin; epipodophyllotoxins such as etoposide or teniposide; antibiotics such as daunorubicin, doxorubicin, bleomycin or mitomycin, enzymes such as L-asparaginase, topoisomerase inhibitors such as topotecan or pyridobenzoindole derivatives; and various agents such as procarbazine, mitoxantrone, and biological response modifiers or growth factor inhibitors such as interferons or interleukins. Other chemotherapeutic agents include, though are not limited to, a p38/JAK kinase inhibitor, e.g., SB203580; a phospatidyl inositol-3 kinase (PI3K) inhibitor, e.g., LY294002; a MAPK inhibitor, e.g. PD98059; a JAK inhibitor, e.g., AG490; preferred chemotherapeutics such as UCN-01, NCS, mitomycin C (MMC), NCS, and anisomycin; taxoids in addition to those describe above (e.g., as disclosed in U.S. Pat. Nos. 4,857,653; 4,814,470; 4,924,011, 5,290,957; 5,292,921; 5,438,072; 5,587,493; European Patent No. 0 253 738; and PCT Publication Nos. WO 91/17976, WO 93/00928, WO 93/00929, and WO 96/01815. In other embodiments, a cancer therapy can include but is not limited to administration of cytokines and growth factors such as interferon (IFN)-gamma, tumor necrosis factor (TNF)-alpha, TNF-beta, and/or similar cytokines, or an antagonist of a tumor growth factor (e.g., TGF-β and IL-10). Antiangiogenic agents, include, e.g., endostatin, angiostatin, TNP-470, Caplostatin (Stachi-Fainaro et al., Cancer Cell 7(3), 251 (2005)). Drugs that interfere with intracellular protein synthesis can also be used in the methods of the present invention; such drugs are known to those skilled in the art and include puromycin, cycloheximide, and ribonuclease.

For radiation therapy, common sources of radiation used for cancer treatment include, but are not limited to, high-energy photons that come from radioactive sources such as cobalt, cesium, iodine, palladium, or a linear accelerator, proton beams; neutron beams (often used for cancers of the head, neck, and prostate and for inoperable tumors).

It is well known that radioisotopes, drugs, and toxins can be conjugated to antibodies or antibody fragments which specifically bind to markers which are produced by or associated with cancer cells, and that such antibody conjugates can be used to target the radioisotopes, drugs or toxins to tumor sites to enhance their therapeutic efficacy and minimize side effects. Examples of these agents and methods are reviewed in Wawrzynczak and Thorpe (in Introduction to the Cellular and Molecular Biology of Cancer, L. M. Franks and N. M. Teich, eds, Chapter 18, pp. 378-410, Oxford University Press. Oxford, 1986), in Immunoconjugates: Antibody Conjugates in Radioimaging and Therapy of Cancer (C. W. Vogel, ed., 3-300, Oxford University Press, N.Y., 1987), in Dillman, R. O. (CRC Critical Reviews in Oncology/Hematology 1:357, CRC Press, Inc., 1984), in Pastan et al. (Cell 47:641, 1986) in Vitetta et al. (Science 238:1098-1104, 1987) and in Brady et al. (Int. J. Rad. Oncol. Biol. Phys. 13:1535-1544, 1987). Other examples of the use of immunoconjugates for cancer and other forms of therapy have been disclosed, inter alia, in U.S. Pat. Nos. 4,331,647, 4,348,376, 4,361,544, 4,468,457, 4,444,744, 4,460,459, 4,460,561 4,624,846, 4,818,709, 4,046,722, 4,671,958, 4,046,784, 5,332,567, 5,443,953, 5,541,297, 5,601,825, 5,637,288, 5,677,427, 5,686,578, 5,698,178, 5,789,554, 5,922,302, 6,187,287, and 6,319,500.

Such inhibitors include antisense oligonucleotides (e.g., RNA interfering molecules such as siRNA and shRNA), aptamers, ribozymes, and small molecules, including certain chemotherapeutic agents. Non-limiting examples of such inhibitors include AZD8330, which is a MEK inhibitor, BKM120, which is a PI3K inhibitor, and GSK1120212, which is also a MEK inhibitor. The skilled artisan will appreciate that any suitable inhibitor of one or more of the above polypeptides is encompassed by the present invention.

VII. Methods for Determining Efficacy of GPP Targeting

Provided herein are methods for determining the efficacy of GPP-targeting in a subject. As described above, GPP-targeting may be carried out for any number of reasons, although preferably, GPP-targeting is administered to a subject for the treatment or prevention of a cancer associated with an oncogenic Kras mutation. Thus, in preferred embodiments, GPP targeting is administered to a subject who has been determined to comprise an oncogenic Kras mutation (e.g., as a prophylactic treatment to delay and/or prevent the onset of or to treat a cancer associated with the oncogenic Kras mutation). A subject may be previously determined or simultaneously determined to comprise an oncogenic Kras mutation (e.g. comprise cells (e.g., cancer cells) expressing an oncogenic Kras mutation).

The presently provided methods for determining the efficacy of GPP-targeting in a subject typically involve determining (e.g., measuring, assaying, estimating) the level (e.g., expression and/or activity) of one or more markers (e.g., enzymes and/or metabolites) associated with an enzyme-catalyzed reaction in the GPP. In a preferred embodiment, the one or more markers measured are selected from the markers that are upstream of ME1-catalyzed reaction in the GPP. While not intending to be bound by any one particular theory or mechanism of action, the present methods are based, at least in part, on the discovery of a novel pathway utilized by cancer cells that are associated with an oncogenic Kras mutation which results in the shunting of glutamine into a non-canonical metabolic pathway (i.e., the GPP) that results in, e.g., increased levels of NADPH, GSH and decreased ROS levels. Thus, inhibition of the GPP can be read out by determining whether the level of one or more of the "end products" of the pathway (e.g., NADPH, GSH, ROS) have been altered. Of course, the skilled artisan will also appreciate that the level of intermediates in the pathway, e.g., markers that are upstream of NADPH, GSH, and ROS (e.g., aspartate, OAA, malate, NAD+, NADH, etc.) can, alternatively, or additionally, be determined in order to determine the efficacy of GPP-targeting, as described in detail below.

The level of any one or more of the markers GLS, GOT2, GOT1, MDH1, ME1, Kras, GLUD1, NADP+, NADPH, GSSG, GSH, pyruvate, glutamine, glutamate, aspartate, αKG, NAD+, NADH, oxaloacetate, ROS (e.g., hydrogen peroxide, super oxide, hydroxyl radical, hypochlorous acid, nitric oxide, peroxyl radical, and singlet oxygen), and malate may be determined in order to determine the efficacy of GPP signaling. The skilled artisan will appreciate that other markers, e.g., subsequently, determined to be associated with an enzyme-catalyzed reaction in the GPP are also encompassed by the present methods.

Typically, the level(s) of the marker(s) is(are) determined in a sample obtained from a subject who is undergoing or has undergone GPP-targeting. The level of the marker is compared to a control level. The control level of a marker typically is the level of the marker in a sample obtained from the same subject prior to or at the beginning of the GPP-targeting. However, the control level can also be based on the level of the marker in a sample obtained from another subject or subjects who is/are known to comprise an oncogenic Kras mutation, so long as that subject or those subjects is/are not undergoing or has/have not undergone GPP-targeting, and preferably, although not necessarily, any other cancer therapies; such a control may be useful, e.g., if a subject's "prior to or at the beginning of the GPP-targeting" sample is not available or was not obtained. In certain embodiments, such control subject(s) has(have) an oncogenic Kras-associated cancer.

Effective inhibition of the GPP will result in a change (i.e., increase or decrease) in the level of the marker in the sample relative to the control level. The control level may be predetermined, or may be simultaneously determined (e.g., measured at the same time the level in the sample is measured).

In certain embodiments, the GPP-targeting is determined to have efficacy if the level of the marker is increased or decreased by a fold-change of at least 2, at least 2.5, at least 3, at least 3.5, at least 4, at least 4.5 fold, at least 5, at least 5.5, at least 6, at least 6.5, at least 7, at least 7.5, at least 8, at least 8.5, at least 9, at least 9.5, at least 10, at least 15, at least 20, or more, compared to the marker's control level. In a preferred embodiment, the level is increased or decreased by at least 2-fold.

In certain embodiments, the control level can be the level in a sample obtained from a healthy subject or subjects (i.e., subject or subjects who have been determined to not comprise an oncogenic Kras mutation and preferably who also do not have cancer). In those embodiments, the GPP-targeting is determined to have been effective if the level of the marker in the sample is the same, i.e., not significantly different (e.g., statistically and/or less than two-fold difference in level) than the control sample. In other words, if the level of the marker in the subject is the same as the level in the control, then it is concluded that the GPP-targeting was effective.

In a preferred embodiment, the marker or combination of markers is selected based on the specific target (e.g., enzyme(s) and/or metabolite(s) of the therapy). As discussed in detail below, and as demonstrated in the present Examples, inhibition of a particular enzyme or metabolite will most observably affect a specific set of markers that are upstream and downstream of the particular target. The skilled artisan will know, based on the description of the GPP provided herein, including a detailed illustration of the pathway in FIG. 39, and the present Examples, how to determine whether the level of a particular marker will increase or decrease when a given enzyme or metabolite is targeted by the therapy.

For clarity and illustrative purposes, the effect of inhibition of certain enzymes in the GPP on the expression levels of certain metabolites in the pathway are exemplified in Table 2, below. However, it is to be understood that Table 2 provides non-limiting examples, and may not show every metabolite that may be affected by inhibition of a particular enzyme, and the skilled artisan will know, based on the disclosure of the GPP (e.g., FIG. 18) and the Examples provided herein, what effect and/or how to determine what effect, if any, inhibition of other enzymes and/or metabolites associated with an enzyme-catalyzed reaction in the GPP will have on the level of the above-described markers.

TABLE 2

Markers Regulated by GPP-Targeting of Specific Enzymes

| | Enzyme Inhibited: | | | | | |
|---|---|---|---|---|---|---|
| | KRAS | GLS | GOT2 | GOT1 | MDH1 | ME1 |
| Markers With Increased Expression Level* | Gln OAA NAD+ NADP+ GSSG ROS | Gln NAD+ NADP+ GSSG ROS | NAD+ NADP+ GSSG ROS | Asp αKG NAD+ NADP+ GSSG ROS | OAA Asp NAD+ NADP+ GSSG ROS | Asp OAA Malate NADP+ GSSG ROS |
| Markers With Decreased Expression Level* | αKG Asp Malate Glu NADH Pyruvate NADPH GSH | Asp Malate Glu OAA NADH Pyruvate NADPH GSH | Asp NADH Pyruvate NADPH GSH | Malate Glu OAA NADH Pyruvate NADPH GSH | Malate NADH Pyruvate GSH | Gln αKG Glu Pyruvate NADPH GSH |

*compared to a control level of the marker (level prior to inhibition of the target enzyme)

In a preferred embodiment, the method for determining the efficacy of GPP-targeting comprises determining the level of one or more markers selected from the group consisting of NADP+, NADPH, GSSG, GSH, pyruvate, and ROS in a sample obtained from a subject who is undergoing or has undergone the GPP-targeting, and concluding that the GPP-targeting was effective if the level of one or more of the markers NADP+, GSSG and ROS is increased, relative to each marker's control level, or if the level of one or more of the markers NADPH, GSH and pyruvate is decreased, relative to each marker's control level; or concluding that the GPP-targeting was not effective if the level of one or more of the markers NADP+, GSSG, and ROS is not increased, relative to each marker's control level, or if the level of one or more of the markers NADPH, GSH and pyruvate is not decreased, relative to each marker's control level. The method can also comprise determining the level of 2 or more, 3 or more, 4 or more, 5 or more, or all 6 or the above-described markers. The method can further comprise determining the level of at least one additional marker selected from the group consisting of glutamine, glutamate, aspartate, αKG, NAD+, NADH, oxaloacetate, malate, MDH1, and ME1.

In certain embodiments, the ratio of NADP+/NADH and/or the ratio of GSSG/GSH and/or the level of ROS is/are determined. In one embodiment, two or more of the ratio of NADP+/NADH, the ratio of GSSG/GSH, and the level of ROS are determined. In another embodiment, the ratio of NADP+/NADH, and the ratio of GSSG/GSH and the level of ROS are determined.

The skilled artisan will readily appreciate that the levels of any combination of the above-described markers can be determined according to the present methods.

In certain embodiments, methods for determining the efficacy of GPP-targeting are provided, wherein the GPP-targeting comprises inhibiting the enzyme GOT2. In those embodiments, it may be concluded that the GPP-targeting was effective if the level of one or more of the markers NADP+, GSSG and ROS is increased, relative to each marker's control level, and/or if the level of one or more of the markers NADPH, GSH, and pyruvate is decreased, relative to each marker's control level; and, optionally, if the level of at least one of the markers selected from the group consisting of NAD+ and NADH is altered relative to each marker's control level. On the other hand, it may be concluded that the GPP-targeting was not effective if the level of one or more of the markers NADP+, GSSG and ROS is not increased, relative to each marker's control level, and/or if the level of one or more of the markers NADPH, GSH, and pyruvate is not decreased, relative to each marker's control level; and, optionally, if the level of at least one of the markers selected from the group consisting of NAD+ NADH is not altered relative to each marker's control level. The skilled artisan will readily appreciate that the levels of any combination of the above-described markers can be determined in order to determine the efficacy of GPP targeting comprising inhibiting the enzyme GOT2.

In another embodiment, methods for determining the efficacy of GPP-targeting are provided, wherein the GPP-targeting comprises inhibiting the enzyme Kras. In that embodiment, it may be concluded that the GPP-targeting was effective if the level of one or more of the markers NADP+, GSSG and ROS is increased, relative to each marker's control level, and/or if the level of one or more of the markers NADPH, GSH, and pyruvate is decreased, relative to each marker's control level; and/or if the level of at least one of the markers selected from the group consisting of glutamine, oxaloacetate, and NAD+ is increased relative to its control level; and/or if the level of at least one of the markers selected from the group consisting of aspartate, αKG, malate, MDH1, and ME1 is decreased relative to each marker's control level. On the other hand, it may be concluded that the GPP-targeting was not effective if the level of one or more of the markers NADP+, GSSG and ROS is not increased, relative to each marker's control level, and/or if the level of one or more of the markers NADPH, GSH, and pyruvate is not decreased, relative to each marker's control level; and, optionally, if the level of at least one of the markers selected from the group consisting of glutamine, oxaloacetate, and NAD-f is not increased relative to its control level; and/or if the level of at least one of the markers selected from the group consisting of aspartate, αKG, malate, MDH1, and ME1 is not decreased relative to each marker's control level.

In still another embodiment, a method for determining the efficacy of oncogenic Kras inhibition in a subject is provided. While not intending to be bound by any one particular theory or mechanism of action, the method is based, at least in part, on the present discovery that inhibition of Kras leads to decreased expression of the enzymes MDH1 and ME1. Thus, in certain embodiments, the method comprises determining the expression level of at least one of the enzymes MDH1 and ME1 in a sample obtained from a subject who is undergoing or has undergone the oncogenic Kras inhibition; and concluding that the oncogenic Kras inhibition was effective if the expression level of the at least one enzyme is decreased compared to a control level of the enzyme; or concluding that the oncogenic Kras inhibition was not effective if the expression level of the at least one enzyme is not decreased compared to a control level of the enzyme.

In other embodiments, methods for determining the efficacy of GPP-targeting are provided, wherein the GPP-targeting comprises inhibiting the enzyme GOT1. In those embodiments, it may be concluded that the GPP-targeting was effective if the level of one or more of the markers NADP+, GSSG and ROS is increased, relative to each marker's control level, and/or if the level of one or more of the markers NADPH, GSH, and pyruvate is decreased, relative to each marker's control level; and, optionally, if the level of at least one of the markers selected from the group consisting of aspartate, αKG, and NAD+ is increased relative to each marker's control level; and/or if the level of at least one of the markers selected from the group consisting of oxaloacetate, malate, glutamate, and NADH is decreased relative to each marker's control level. On the other hand, it may be concluded that the GPP-targeting was not effective if the level of one or more of the markers NADP+, GSSG and ROS is not increased, relative to each marker's control level, and/or if the level of one or more of the markers NADPH, GSH, and pyruvate is not decreased, relative to each marker's control level; and, optionally, if the level of at least one of the markers selected from the group consisting of aspartate, αKG, and NAD+ is not increased relative to each marker's control level; and/or if the level of at least one of the markers selected from the group consisting of oxaloacetate, malate, glutamate, and NADH is not decreased relative to each marker's control level.

In other embodiments, methods for determining the efficacy of GPP-targeting are provided, wherein the GPP-targeting comprises inhibiting the enzyme MDH1. In those embodiments, it may be concluded that the GPP-targeting was effective if the level of one or more of the markers NADP+, GSSG and ROS is increased, relative to each marker's control level, and/or if the level of one or more of the markers NADPH, GSH, and pyruvate is decreased, relative to each marker's control level; and, optionally, if the level of at least one of the markers selected from the group consisting of oxaloacetate and NAD+ is increased relative to each marker's control level; and/or if the level of at least one of the markers selected from the group consisting of malate and NADH is decreased relative to each marker's control level. On the other hand, it may be concluded that the GPP-targeting was not effective if the level of one or more of the markers NADP+, GSSG and ROS is not increased, relative to each marker's control level, and/or if the level of one or more of the markers NADPH, GSH, and pyruvate is not decreased, relative to each marker's control level; and, optionally, if the level of at least one of the markers selected from the group consisting of oxaloacetate and NAD+ is not increased relative to each marker's control level; and/or if the level of at least one of the markers selected from the group consisting of malate and NADH is not decreased relative to each marker's control level.

In other embodiments, methods for determining the efficacy of GPP-targeting are provided, wherein the GPP-targeting comprises inhibiting the enzyme GLS. In those embodiments, it may be concluded that the GPP-targeting was effective if the level of one or more of the markers NADP+, GSSG and ROS is increased, relative to each marker's control level, and/or if the level of one or more of the markers NADPH, GSH, and pyruvate is decreased, relative to each marker's control level; and, optionally, if the level of at least one of the markers selected from the group consisting of glutamine and NAD+ is increased relative to each marker's control level, or if the level of at least one of the markers selected from the group consisting of aspartate, oxaloacetate, malate, glutamate, and NADH is decreased relative to each marker's control level. On the other hand, it may be concluded that the GPP-targeting was not effective if the level of one or more of the markers NADP+, GSSG and ROS is not increased, relative to each marker's control level, and/or if the level of one or more of the markers NADPH, GSH, and pyruvate is not decreased, relative to each marker's control level; and, optionally, if the level of at least one of the markers selected from the group consisting of glutamine and NAD+ is not increased relative to each marker's control level, and/or if the level of at least one of the markers selected from the group consisting of aspartate, oxaloacetate, malate, glutamate, and NADH is not decreased relative to each marker's control level.

In yet another embodiment, a method for determining the efficacy of GPP-targeting in a subject comprising an oncogenic Kras mutation (e.g., a subject with a cancer associated with an oncogenic Kras mutation) is provided, wherein the GPP-targeting comprises targeting one or more of the enzymes catalyzing the conversion of glutamine to aspartate (e.g. GLS, GOT2). While not intending to be bound by any one particular theory or mechanism of action, the present method is based, at least in part, on the present discovery that glutamate is converted to aspartate in the GPP, rather than to αKG via the canonical pathway mediated by GLUD1. Thus, effective inhibition of the enzymes catalyzing the conversion of glutamine to aspartate can be determined by testing for alterations of any of the metabolites downstream of and including aspartate in the GPP. Preferably, the method comprises determining the level of at least one marker selected from the group consisting of GSSG, GSH, aspartate, αKG, NADP+, NADPH, NAD+, NADH, pyruvate, oxaloacetate, and malate in a sample obtained from a subject who is undergoing or has undergone the GPP-targeting. Further, it may be concluded that the GPP-targeting was effective if the level of one or more of GSSG, GSH, aspartate, αKG, NADP+, NADPH, NAD+, NADH, pyruvate, oxaloacetate, and malate is altered relative to each marker's control level.

In another method, a method for determining the efficacy of oncogenic Kras inhibition in a subject having a cell having an oncogenic Kras mutation is provided, wherein the method includes determining the expression level of at least one of the enzymes GLUD1 and GOT1 in a sample obtained from a subject who is undergoing or has undergone the oncogenic Kras inhibition; and concluding that the oncogenic Kras inhibition was effective if the expression level of GOT1 is decreased compared to a control level of the enzyme and/or if the expression level of GLUD1 is increased compared to a control level of the enzyme; or concluding that the oncogenic Kras inhibition was not effective if the expression level of GOT1 is not decreased compared to a control level of the enzyme and/or if the expression level of GLUD1 is not increased compared to a control level of the enzyme. In certain aspects of the method, the ratio of GLUD1 and GOT1 can be determined.

In certain methods disclosed herein, the method includes concluding that the GPP-targeting (e.g., with an inhibitor of GOT1 or MDH1) was not effective if the level of aspartate is not increased relative to a control level; or concluding that the GPP-targeting was effective if the level of aspartate is increased relative to a control level.

Also provided herein is a method for determining the efficacy of glutamine to pyruvate pathway (GPP)-targeting in a subject having an oncogenic Kras mutation, and the GPP-targeting comprises inhibiting GOT1, MDH1, or ME1, the method including: determining the level of aspartate in a sample obtained from a subject who is undergoing or has undergone the GPP-targeting; and concluding that the GPP-targeting was effective if the level of aspartate is increased relative to a control level; or concluding that the GPP-targeting was not effective if the level of aspartate is not increased relative to a control level.

In any of the above-disclosed methods for determining the efficacy of GPP-targeting in a subject having an oncogenic Kras mutation (e.g., a subject with a cancer associated with an oncogenic Kras mutation), the method can include further steps. For example, in one embodiment, the method can further include continuing the GPP-targeting of the subject, at the same dose or frequency or at a lower dose or frequency, if, for example, it is concluded that the GPP-targeting prior to the efficacy determination was at least partially effective. Moreover, the method can further include decreasing the dose and/or frequency or altogether discontinuing GPP-targeting in the subject, if, for example, it is concluded that the targeting was curatively effective. However, if, for example, it is concluded that GPP-targeting was not effective, it can be discontinued. Alternatively, if it was not effective, or was not optimal, the method can further include the step of administering a different treatment or repeating the GPP-targeting in the subject and/or adjusting the dose and/or frequency of GPP targeting. Different treatments are known in art and include those described herein, such as surgery, chemotherapy, and radiotherapy. In other embodiments, if, for example, it is concluded that GPP-targeting was not effective, or was not optimal, the method can further include the step of administering a combination treatment to the subject, e.g., a treatment targeting at least two members (e.g., metabolite or enzyme) of the GPP or any GPP-targeting in combination with one or more of the above-mentioned "different treatments."

VIII. Design of Metabolite and Enzyme Inhibitors

Design of inhibitors of the metabolites disclosed herein, such as, e.g., those described above, will depend on the specific metabolite being targeted. Non-limiting examples of such inhibitors include, e.g., small molecules and non-functional binding proteins, which can trap the metabolite and prevent its function. Hydrogen peroxide, for example, and without limitation, can be used to antagonize GSH, NADH, and NADPH. Further, aminooxyacentate (AOA), as disclosed in the present Examples, and in Wise, D. R. et al. (2008) *Proc Natl Acad Sci USA* 105, 18782-18787], inhibits transaminases (e.g., GOT1 and GOT2). The skilled artisan will understand how to design such inhibitors, based on methods well known in the art.

Methods for designing inhibitors of the enzymes of the invention (e.g., GLS, GOT2, GOT1, MDH1, ME1, etc.) are well known in the art. The following are thus provided as non-limiting examples of such inhibitors; the skilled artisan will understand that other inhibitors that decrease the level (e.g., expression or activity) of a target of the invention are also encompassed by the present methods.

i. Antisense Nucleic Acids

Antisense oligonucleotides can be used to inhibit the expression of a target polypeptide of the invention (e.g., Gfpt1, RPIA, RPE, etc.). Antisense oligonucleotides typically comprise from about 5 nucleotides to about 30 nucleotides in length, preferably from about 10 to about 25 nucleotides in length, and more preferably from about 20 to about 25 nucleotides in length. For a general discussion of antisense technology, see, e.g., Antisense DNA and RNA, (Cold Spring Harbor Laboratory, D. Melton, ed., 1988).

Appropriate chemical modifications of the inhibitors are made to ensure stability of the antisense oligonucleotide, as described below. Changes in the nucleotide sequence and/or in the length of the antisense oligonucleotide can be made to ensure maximum efficiency and thermodynamic stability of the inhibitor. Such sequence and/or length modifications are readily determined by one of ordinary skill in the art.

The antisense oligonucleotides can be DNA or RNA or chimeric mixtures, or derivatives or modified versions thereof, and can be single-stranded or double-stranded. Thus, for example, in the antisense oligonucleotides set forth in herein, when a sequence includes thymidine residues, one or more of the thymidine residues may be replaced by uracil residues and, conversely, when a sequence includes uracil residues, one or more of the uracil residues may be replaced by thymidine residues.

Antisense oligonucleotides comprise sequences complementary to at least a portion of the corresponding target polypeptide. However, 100% sequence complementarity is not required so long as formation of a stable duplex (for single stranded antisense oligonucleotides) or triplex (for double stranded antisense oligonucleotides) can be achieved. The ability to hybridize will depend on both the degree of complementarity and the length of the antisense oligonucleotides. Generally, the longer the antisense oligonucleotide, the more base mismatches with the corresponding nucleic acid target can be tolerated. One skilled in the art can ascertain a tolerable degree of mismatch by use of standard procedures to determine the melting point of the hybridized complex.

Antisense nucleic acid molecules can be encoded by a recombinant gene for expression in a cell (see, e.g., U.S. Pat. Nos. 5,814,500 and 5,811,234), or alternatively they can be prepared synthetically (see, e.g., U.S. Pat. No. 5,780,607).

The antisense oligonucleotides can be modified at the base moiety, sugar moiety, or phosphate backbone, or a combination thereof. In one embodiment, the antisense oligonucleotide comprises at least one modified sugar moiety, e.g., a sugar moiety selected from arabinose, 2-fluoroarabinose, xylulose, and hexose.

In another embodiment, the antisense oligonucleotide comprises at least one modified phosphate backbone selected from a phosphorothioate, a phosphorodithioate, a phosphoramidothioate, a phosphoramidate, a phosphordiamidate, a methylphosphonate, an alkyl phosphotriester, and a formacetal or analog thereof. Examples include, without limitation, phosphorothioate antisense oligonucleotides (e.g., an antisense oligonucleotide phosphothioate-modified at 3' and 5' ends to increase its stability) and chimeras between methylphosphonate and phosphodiester oligonucleotides. These oligonucleotides provide good in vivo activity due to solubility, nuclease resistance, good cellular uptake, ability to activate RNase H, and high sequence selectivity.

Other examples of synthetic antisense oligonucleotides include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with CH2-NH—O—CH2, CH2-N(CH3)-O—CH2, CH2-O—N(CH3)-CH2, CH2-N(CH3)-N(CH3)-CH2 and O—N(CH3)-CH2-CH2 backbones (where phosphodiester is O—PO2-O—CH2). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds.

In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 1991; 254:1497). Other synthetic oligonucleotides may contain substituted sugar moieties comprising one of the following at the 2' position: OH, SH, SCH3, F, OCN, O(CH2)nNH2 or O(CH2)nCH3 where n is from 1 to about 10; C1 to C10 lower alkyl, substituted lower alkyl, alkaryl or aralkyl; Cl; Br; CN; CF3; OCF3; O-; S-, or N-alkyl; O-, S-, or N-alkenyl; SOCH3; SO2CH3; ONO2; NO2; N3; NH2; heterocycloalkyl; heterocycloalkaryl; aminoalkylamino; polyalkylamino; substituted sialyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties.

Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine. In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) with a 2'-O, 4'-C methylene bridge. This bridge restricts the flexibility of the ribofuranose ring and locks the structure into a rigid C3-endo conformation, conferring enhanced hybridization performance and exceptional biostability. LNA allows the use of very short oligonucleotides (less than 10 bp) for efficient hybridization in vivo.

In one embodiment, an antisense oligonucleotide can comprise at least one modified base moiety selected from a group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the antisense oligonucleotide can include α-anomeric oligonucleotides. An α-anomeric oligonucleotide forms specific double-stranded hybrids with complementary RNA in which, contrary to the usual β-units, the strands run parallel to each other (Gautier et al., Nucl. Acids Res. 1987; 15:6625-6641).

Oligonucleotides may have morpholino backbone structures (U.S. Pat. No. 5,034,506). Thus, in yet another embodiment, the antisense oligonucleotide can be a morpholino antisense oligonucleotide (i.e., an oligonucleotide in which the bases are linked to 6-membered morpholine rings, which are connected to other morpholine-linked bases via nonionic phosphorodiamidate intersubunit linkages). Morpholino oligonucleotides are highly resistant to nucleases and have good targeting predictability, high in-cell efficacy and high sequence specificity (U.S. Pat. No. 5,034,506;

Summerton, Biochim. Biophys. Acta 1999; 1489:141-158; Summerton and Weller, Antisense Nucleic Acid Drug Dev. 1997; 7:187-195; Arora et al., J. Pharmacol. Exp. Ther. 2000; 292:921-928; Qin et al., Antisense Nucleic Acid Drug Dev. 2000; 10:11-16; Heasman et al., Dev. Biol. 2000; 222:124-134; Nasevicius and Ekker, Nat. Genet. 2000; 26:216-220).

Antisense oligonucleotides may be chemically synthesized, for example using appropriately protected ribonucleoside phosphoramidites and a conventional DNA/RNA synthesizer. Antisense nucleic acid oligonucleotides can also be produced intracellularly by transcription from an exogenous sequence. For example, a vector can be introduced in vivo such that it is taken up by a cell within which the vector or a portion thereof is transcribed to produce an antisense RNA. Such a vector can remain episomal or become chromosomally integrated, so long as it can be transcribed to produce the desired antisense RNA. Such vectors can be constructed by recombinant DNA technology methods standard in the art. Vectors can be plasmid, viral, or others known in the art, used for replication and expression in mammalian cells. In another embodiment, "naked" antisense nucleic acids can be delivered to adherent cells via "scrape delivery", whereby the antisense oligonucleotide is added to a culture of adherent cells in a culture vessel, the cells are scraped from the walls of the culture vessel, and the scraped cells are transferred to another plate where they are allowed to re-adhere. Scraping the cells from the culture vessel walls serves to pull adhesion plaques from the cell membrane, generating small holes that allow the antisense oligonucleotides to enter the cytosol.

ii. RNAi

Reversible short inhibition of a target polypeptide (e.g., Gfpt1, RPIA, RPE, etc.) of the invention may also be useful. Such inhibition can be achieved by use of siRNAs. RNA interference (RNAi) technology prevents the expression of genes by using small RNA molecules such as small interfering RNAs (siRNAs). This technology in turn takes advantage of the fact that RNAi is a natural biological mechanism for silencing genes in most cells of many living organisms, from plants to insects to mammals (McManus et al., Nature Reviews Genetics, 2002, 3(10) p. 737). RNAi prevents a gene from producing a functional protein by ensuring that the molecule intermediate, the messenger RNA copy of the gene is destroyed siRNAs can be used in a naked form and incorporated in a vector, as described below.

RNA interference (RNAi) is a process of sequence-specific post-transcriptional gene silencing by which double stranded RNA (dsRNA) homologous to a target locus can specifically inactivate gene function in plants, fungi, invertebrates, and vertebrates, including mammals (Hammond et al., Nature Genet. 2001; 2:110-119; Sharp, Genes Dev. 1999; 13:139-141). This dsRNA-induced gene silencing is mediated by short double-stranded small interfering RNAs (siRNAs) generated from longer dsRNAs by ribonuclease III cleavage (Bernstein et al., Nature 2001; 409:363-366 and Elbashir et al., Genes Dev. 2001; 15:188-200). RNAi-mediated gene silencing is thought to occur via sequence-specific RNA degradation, where sequence specificity is determined by the interaction of an siRNA with its complementary sequence within a target RNA (see, e.g., Tuschl, Chem. Biochem. 2001; 2:239-245).

For mammalian systems, RNAi commonly involves the use of dsRNAs that are greater than 500 bp; however, it can also be activated by introduction of either siRNAs (Elbashir et al., Nature 2001; 411: 494-498) or short hairpin RNAs (shRNAs) bearing a fold back stem-loop structure (Paddison et al., Genes Dev. 2002; 16: 948-958; Sui et al., Proc. Natl. Acad. Sci. USA 2002; 99:5515-5520; Brummelkamp et al., Science 2002; 296:550-553; Paul et al., Nature Biotechnol. 2002; 20:505-508).

The siRNAs are preferably short double stranded nucleic acid duplexes comprising annealed complementary single stranded nucleic acid molecules. Preferably, the siRNAs are short dsRNAs comprising annealed complementary single strand RNAs. siRNAs may also comprise an annealed RNA:DNA duplex, wherein the sense strand of the duplex is a DNA molecule and the antisense strand of the duplex is a RNA molecule.

Preferably, each single stranded nucleic acid molecule of the siRNA duplex is of from about 19 nucleotides to about 27 nucleotides in length. In preferred embodiments, duplexed siRNAs have a 2 or 3 nucleotide 3' overhang on each strand of the duplex. In preferred embodiments, siRNAs have 5'-phosphate and 3'-hydroxyl groups.

RNAi molecules may include one or more modifications, either to the phosphate-sugar backbone or to the nucleoside. For example, the phosphodiester linkages of natural RNA may be modified to include at least one heteroatom other than oxygen, such as nitrogen or sulfur. In this case, for example, the phosphodiester linkage may be replaced by a phosphothioester linkage. Similarly, bases may be modified to block the activity of adenosine deaminase. Where the RNAi molecule is produced synthetically, or by in vitro transcription, a modified ribonucleoside may be introduced during synthesis or transcription. The skilled artisan will understand that many of the modifications described above for antisense oligonucleotides may also be made to RNAi molecules. Such modifications are well known in the art.

siRNAs may be introduced to a target cell as an annealed duplex siRNA, or as single stranded sense and antisense nucleic acid sequences that, once within the target cell, anneal to form the siRNA duplex. Alternatively, the sense and antisense strands of the siRNA may be encoded on an expression construct that is introduced to the target cell. Upon expression within the target cell, the transcribed sense and antisense strands may anneal to reconstitute the siRNA.

shRNAs typically comprise a single stranded "loop" region connecting complementary inverted repeat sequences that anneal to form a double stranded "stem" region. Structural considerations for shRNA design are discussed, for example, in McManus et al., RNA 2002; 8:842-850. In certain embodiments the shRNA may be a portion of a larger RNA molecule, e.g., as part of a larger RNA that also contains U6 RNA sequences (Paul et al., supra).

In preferred embodiments, the loop of the shRNA is from about 1 to about 9 nucleotides in length. In preferred embodiments the double stranded stem of the shRNA is from about 19 to about 33 base pairs in length. In preferred embodiments, the 3' end of the shRNA stem has a 3' overhang. In particularly preferred embodiments, the 3' overhang of the shRNA stem is from 1 to about 4 nucleotides in length. In preferred embodiments, shRNAs have 5'-phosphate and 3'-hydroxyl groups.

Although RNAi molecules preferably contain nucleotide sequences that are fully complementary to a portion of the target nucleic acid, 100% sequence complementarity between the RNAi probe and the target nucleic acid is not required.

Similar to the above-described antisense oligonucleotides, RNAi molecules can be synthesized by standard methods known in the art, e.g., by use of an automated synthesizer. RNAs produced by such methodologies tend to be highly pure and to anneal efficiently to form siRNA duplexes or shRNA hairpin stem-loop structures. Following chemical synthesis, single stranded RNA molecules are deprotected, annealed to form siRNAs or shRNAs, and purified (e.g., by gel electrophoresis or HPLC). Alternatively, standard procedures may be used for in vitro transcription of RNA from DNA templates carrying RNA polymerase promoter sequences (e.g., T7 or SP6 RNA polymerase promoter sequences). Efficient in vitro protocols for preparation of siRNAs using T7 RNA polymerase have been described (Donzé and Picard, Nucleic Acids Res. 2002; 30:e46; and Yu et al., Proc. Natl. Acad. Sci. USA 2002; 99:6047-6052). Similarly, an efficient in vitro protocol for preparation of shRNAs using T7 RNA polymerase has been described (Yu et al., supra). The sense and antisense transcripts may be synthesized in two independent reactions and annealed later, or may be synthesized simultaneously in a single reaction.

RNAi molecules may be formed within a cell by transcription of RNA from an expression construct introduced into the cell. For example, both a protocol and an expression construct for in vivo expression of siRNAs are described in Yu et al., supra. The delivery of siRNA to tumors can potentially be achieved via any of several gene delivery "vehicles" that are currently available. These include viral vectors, such as adenovirus, lentivirus, herpes simplex virus, vaccinia virus, and retrovirus, as well as chemical-mediated gene delivery systems (for example, liposomes), or mechanical DNA delivery systems (DNA guns). The oligonucleotides to be expressed for such siRNA-mediated inhibition of gene expression would be between 18 and 28 nucleotides in length. Protocols and expression constructs for in vivo expression of shRNAs have been described (Brummelkamp et al., Science 2002; 296:550-553; Sui et al., supra; Yu et al., supra; McManus et al., supra; Paul et al., supra).

The expression constructs for in vivo production of RNAi molecules comprise RNAi encoding sequences operably linked to elements necessary for the proper transcription of the RNAi encoding sequence(s), including promoter elements and transcription termination signals. Preferred promoters for use in such expression constructs include the polymerase-III HI-RNA promoter (see, e.g., Brummelkamp et al., supra) and the U6 polymerase-II promoter (see, e.g., Sui et al., supra; Paul, et al. supra; and Yu et al., supra). The RNAi expression constructs can further comprise vector sequences that facilitate the cloning of the expression constructs. Standard vectors are known in the art (e.g., pSilencer 2.0-U6 vector, Ambion Inc., Austin, Tex.).

iii. Ribozyme Inhibition

The level of expression of a target polypeptide of the invention can also be inhibited by ribozymes designed based on the nucleotide sequence thereof.

Ribozymes are enzymatic RNA molecules capable of catalyzing the sequence-specific cleavage of RNA (for a review, see Rossi, Current Biology 1994; 4:469-471). The mechanism of ribozyme action involves sequence-specific hybridization of the ribozyme molecule to complementary target RNA, followed by an endonucleolytic cleavage event. The composition of ribozyme molecules must include: (i) one or more sequences complementary to the target RNA; and (ii) a catalytic sequence responsible for RNA cleavage (see, e.g., U.S. Pat. No. 5,093,246).

The use of hammerhead ribozymes is preferred. Hammerhead ribozymes cleave RNAs at locations dictated by flanking regions that form complementary base pairs with the target RNA. The sole requirement is that the target RNA has the following sequence of two bases: 5'-UG-3'. The construction of hammerhead ribozymes is known in the art, and described more fully in Myers, Molecular Biology and Biotechnology: A Comprehensive Desk Reference, VCH Publishers, New York, 1995 (see especially FIG. 4, page 833) and in Haseloff and Gerlach, Nature 1988; 334:585-591.

As in the case of antisense oligonucleotides, ribozymes can be composed of modified oligonucleotides (e.g., for improved stability, targeting, etc.). These can be delivered to cells which express the target polypeptide in vivo. A preferred method of delivery involves using a DNA construct "encoding" the ribozyme under the control of a strong constitutive pol III or pol II promoter, so that transfected cells will produce sufficient quantities of the ribozyme to catalyze cleavage of the target mRNA encoding the target polypeptide. However, because ribozymes, unlike antisense molecules, are catalytic, a lower intracellular concentration may be required to achieve an adequate level of efficacy.

Ribozymes can be prepared by any method known in the art for the synthesis of DNA and RNA molecules, as discussed above. Ribozyme technology is described further in Intracellular Ribozyme Applications: Principals and Protocols, Rossi and Couture eds., Horizon Scientific Press, 1999.

iv. Triple Helix Forming Oligonucleotides (TFOs)

Nucleic acid molecules useful to inhibit expression level of a target polypeptide of the invention via triple helix formation are preferably composed of deoxynucleotides. The base composition of these oligonucleotides is typically designed to promote triple helix formation via Hoogsteen base pairing rules, which generally require sizeable stretches of either purines or pyrimidines to be present on one strand of a duplex. Nucleotide sequences may be pyrimidine-based, resulting in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, e.g., those containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, sequences can be targeted for triple helix formation by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Similarly to RNAi molecules, antisense oligonucleotides, and ribozymes, described above, triple helix molecules can be prepared by any method known in the art. These include techniques for chemically synthesizing oligodeoxyribonucleotides and oligoribonucleotides such as, e.g., solid phase phosphoramidite chemical synthesis. Alternatively, RNA molecules can be generated by in vitro or in vivo transcription of DNA sequences "encoding" the particular RNA molecule. Such DNA sequences can be incorporated into a wide variety of vectors that incorporate suitable RNA polymerase promoters such as the T7 or SP6 polymerase promoters. See, Nielsen, P. E. "Triple Helix: Designing a New Molecule of Life", Scientific American, December, 2008; Egholm, M., et al. "PNA Hybridizes to Complementary Oligonucleotides Obeying the Watson-Crick Hydrogen Bonding Rules." (1993) Nature, 365, 566-568; Nielsen, P. E. 'PNA Technology'. Mol Biotechnol. 2004; 26:233-48.

v. Antibodies and Aptamers

The enzymes described herein, e.g., GOT1, GOT2, MDH1, ME1, can be inhibited (e.g. the level can be reduced) by the administration to or expression in a subject or a cell or tissue thereof, of blocking antibodies or aptamers against the enzyme.

Antibodies, or their equivalents and derivatives, e.g., intrabodies, or other antagonists of the enzyme, may be used in accordance with the present methods for GPP-targeting. Methods for engineering intrabodies (intracellular single chain antibodies) are well known. Intrabodies are specifically targeted to a particular compartment within the cell, providing control over where the inhibitory activity of the treatment is focused. This technology has been successfully applied in the art (for review, see Richardson and Marasco, 1995, TIBTECH vol. 13; Lo et al. (2009) Handb Exp Pharmacol. 181:343-73; Marasco, W. A. (1997) Gene Therapy 4:11-15; see also, U.S. Pat. Appln. Pub. No. 2001/0024831 by Der Maur et al. and U.S. Pat. No. 6,004,940 by Marasco et al.).

Administration of a suitable dose of the antibody or the antagonist (e.g., aptamer) may serve to block the level (expression or activity) of the enzyme in order to block the GPP, and/or e.g., inhibit growth of a cell, e.g., cancer cell, comprising an oncogenic Kras mutation.

In addition to using antibodies to inhibit the levels and/or activity of the enzyme, it may also be possible to use other forms of inhibitors. For example, it may be possible to identify antagonists that functionally inhibit the target enzyme (e.g., GOT1, GOT2, ME1, MDH1, etc.). In addition, it may also be possible to interfere with the interaction of the enzyme with its substrate. Other suitable inhibitors will be apparent to the skilled person.

The antibody (or other inhibitors or intrabody) can be administered by a number of methods. One method is set forth by Marasco and Haseltine in PCT WO 94/02610. This method discloses the intracellular delivery of a gene encoding the intrabody. In one embodiment, a gene encoding a single chain antibody is used. In another embodiment, the antibody would contain a nuclear localization sequence. By this method, one can intracellularly express an antibody, which can block activity of the enzyme in desired cells.

Aptamers are oligonucleic acid or peptide molecules that bind to a specific target molecule. Aptamers can be used to inhibit gene expression and to interfere with protein interactions and activity. Nucleic acid aptamers are nucleic acid species that have been engineered through repeated rounds of in vitro selection (e.g. by SELEX (systematic evolution of ligands by exponential enrichment)) to bind to various molecular targets such as small molecules, proteins, nucleic acids, and even cells, tissues and organisms. Peptide aptamers consist of a variable peptide loop attached at both ends to a protamersein scaffold. Aptamers are useful in biotechnological and therapeutic applications as they offer molecular recognition properties that rival that of antibodies. Aptamers can be engineered completely in a test tube, are readily produced by chemical synthesis, possess desirable storage properties, and elicit little or no immunogenicity in therapeutic application. Aptamers can be produced using the methodology disclosed in a U.S. Pat. No. 5,270,163 and WO 91/19813.

vi. Small Molecules

Chemical agents, referred to in the art as "small molecule" compounds are typically organic, non-peptide molecules, having a molecular weight less than 10,000 Da, preferably less than 5,000 Da, more preferably less than 1,000 Da, and most preferably less than 500 Da. This class of modulators includes chemically synthesized molecules, for instance, compounds from combinatorial chemical libraries. Synthetic compounds may be rationally designed or identified utilizing the screening methods described below. Methods for generating and obtaining small molecules are well known in the art (Schreiber, Science 2000; 151:1964-1969; Radmann et al., Science 2000; 151:1947-1948).

IX. Administration

Compositions and formulations comprising an inhibitor (or agonist) of the invention (e.g., an inhibitor or agonist of an enzyme or metabolite associated with an enzyme-catalyzed reaction in the GPP, can be administered topically, parenterally, orally, by inhalation, as a suppository, or by other methods known in the art. The term "parenteral" includes injection (for example, intravenous, intraperitoneal, epidural, intrathecal, intramuscular, intraluminal, intratracheal or subcutaneous). Preferred routes of administration are oral and intravenous (IV), although intratumoral administration is also possible.

While it is possible to use an inhibitor or agonist or other composition of the invention for therapy as is, it may be preferable to administer a composition as a pharmaceutical formulation, e.g., in admixture with a suitable pharmaceutical excipient, diluent, or carrier selected with regard to the intended route of administration and standard pharmaceutical practice. Pharmaceutical formulations comprise at least one active compound, or a pharmaceutically acceptable derivative thereof, in association with a pharmaceutically acceptable excipient, diluent, and/or carrier. The excipient, diluent and/or carrier must be "acceptable," as defined above.

Administration of a composition of the invention (e.g., inhibitor or agonist) can be once a day, twice a day, or more often. Frequency may be decreased during a treatment maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the present compounds.

It will be appreciated that the amount of a composition of the invention (e.g. inhibitor or agonist) required for use in treatment will vary with the route of administration, the nature of the condition for which treatment is required, and the age, body weight and condition of the patient, and will be ultimately at the discretion of the attendant physician or veterinarian. Compositions will typically contain an effective amount of the active agent(s), alone or in combination. Preliminary doses can be determined according to animal tests, and the scaling of dosages for human administration can be performed according to art-accepted practices.

Length of treatment, i.e., number of days, will be readily determined by a physician treating the subject; however the number of days of treatment may range from 1 day to about 20 days. As provided by the present methods, the efficacy of treatment can be monitored during the course of treatment to determine whether the treatment has been successful, or whether additional (or modified) treatment is necessary.

X. Kits

In certain embodiments, kits are provided for use in GPP-targeting, e.g., for the treatment of a cancer associated with an oncogenic Kras mutation. For example, a kit comprising an inhibitor of ME1 and one or more inhibitors of one or more of the enzymes selected from the group consisting of Kras, GOT2, GLS, GOT1, and MDH1 is provided. In another embodiment, a kit comprising an inhibitor of GLS and one or more inhibitors of one or more of the enzymes selected from the group consisting of Kras, GOT2, ME1, GOT1, and MDH1 is provided. In yet another embodiment, a kit comprising an inhibitor of at least one of the enzymes selected from the group consisting of Kras, ME1, GLS, GOT1, GOT2, and MDH1, and an inhibitor of one or more metabolites associated with an enzyme-catalyzed reaction in the GPP is provided. The above described kits may comprise an inhibitor of two or more metabolites associated with an enzyme-catalyzed reaction in the GPP. In certain embodiments, the inhibitor(s) in the above-described kits can target a metabolite selected from the group consisting of glutamine, glutamate, aspartate, oxaloacetate, malate, pyruvate, NADH, NADPH, and GSH.

The kits, regardless of type, will generally comprise one or more containers into which the biological agents (e.g. inhibitors) are placed and, preferably, suitably aliquotted. The components of the kits may be packaged either in aqueous media or in lyophilized form.

The above-described kits may come with instructions for using the kit for GPP targeting, e.g., for treating or preventing a cancer associated with an oncogenic Kras mutation.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

The following examples are meant to illustrate, not limit, the invention.

EXAMPLES

Example 1: Materials and Methods

The following are the materials and methods used in the Examples set forth below.

Proliferation and clonogenic assays were performed as previously described (Yang, S. et al. *Genes Dev* 25, 717-729 (2011)). To characterize Gln metabolism, targeted liquid chromatography-tandem mass spectrometry was performed (Ying et al. supra). Briefly, cells were grown in complete media and transferred into Gln-free media supplemented with [U-$^{13}$C5]-Gln overnight (steady state) or for the indicated timepoints (flux analyses). For subcutaneous xenografts, PDAC cells infected with lentiviral shRNAs to suppress target gene expression were suspended in 100 μl HBSS and injected subcutaneously into the lower flank of NCr nude mice. For mouse xenografts, murine PDAC cells stably infected with a doxycycline-inducible GOT1 shRNA construct were injected. Animals were fed with doxycycline water starting on the day of injection or when tumor volume reached ~50 mm$^3$.

Cell Culture

Cell lines were obtained from the American Type Culture Collection or the German Collection of Microorganisms and Cell Cultures. All cell lines were tested routinely, and prior to all metabolomic analyses, for mycoplasma contamination. RPMI-1640, fetal bovine serum and dialyzed fetal bovine serum (dFBS) were purchased from Invitrogen. Glucose free DMEM (containing 2 mM Gln), dimethyl αKG, Asp, GSH reduced ethyl ester, OAA, dimethyl malate and DMEM power (without glucose and Gln) were obtained from Sigma, and Gln-free RPMI 1640 was purchased from Cellgro. Cosmic calf serum (CCS) was obtained from Thermo Scientific. Cells were cultured in the following media: 8988T, Panc1, MPanc96, Miapaca2 and PL45 in DMEM supplemented with 10 mM glucose and 10% CCS; 8902 in RPMI with 10% CCS; IMR90 in MEM with 10% FBS; HPDE cells were cultured as described previously [Ouyang, H. et al. (2000) *Am J Pathol* 157, 1623-1631]. Primary human PDAC lines were generated from ascites fluid under IRB approved protocols 02-240 and 2007P001918. The lines were confirmed to have Kras mutations by DNA sequencing.

Cell Proliferation Assay

Cells were plated in 24-well plates at 2,000 cells per well in 0.5 mL of media. To deprive Gln, cells were plated in complete culture medium (10 mM glucose and 2 mM Gln) which was exchanged with Gln-free culture medium supplemented with 10% dFBS the following day. Cell culture media was not changed throughout the course of the experiment. At the indicated time points, cells were fixed in 10% formalin and stained with 0.1% crystal violet. Dye was extracted with 10% acetic acid and the relative proliferation was determined by OD at 595 nm.

Clonogenic Assay

Cells were plated in 6-well plates at 300 cells per well in 2 mL of media. Cell culture media was not changed throughout the course of the experiment. After 7-10 days, colonies were fixed in 80% methanol and stained with 0.2% crystal violet.

Quantitative RT-PCR

Total RNA was extracted using TRIzol (Invitrogen) and reverse transcription was performed from 2 μg of total RNA using oligo-dT and MMLV HP reverse transcriptase (Epicentre), according to the manufacturer's instructions. Quantitative RT-PCR was performed with SYBR Green dye using an Mx3000P™ (Stratagene). PCR reactions were performed in triplicate and the relative amount of cDNA was calculated by the comparative CT method using the 18S ribosomal RNA sequences as a control. Primer sequences available upon request.

Oxygen Consumption Rate

Oxygen consumption rates (OCRs) were monitored with the Seahorse XF24 instrument (Seahorse Biosciences).

30,000 cells were plated in quadruplicate in a 24-well Seahorse plate in 250 μL of appropriate growth medium and incubated overnight. Prior to measurements, cells were washed with unbuffered medium, then immersed in unbuffered medium and incubated in a 37° incubator without $CO_2$ for 1 hr. Measurements were reported in pmol/min for oxygen consumption.

Xenograft Studies

For subcutaneous xenografts, 8988T cells were infected with lentiviral shRNAs targeting GLUD1 (n=2), GOT1 (n=2), MDH1 (n=2), ME1 (n=2) and GFP (control hairpin, n=1) and subjected to a short puromycin selection (2 μg/mL); shRNA ARE sequences below. $1.5 \times 10^6$ cells, suspended in 100 μL Hanks Buffered Saline Solution (HBSS), were injected subcutaneously into the lower flank of NCr nude mice (Taconic). Tumor length and width were measured twice weekly and the volume was calculated according to the formula (length×width$^2$)/2. All xenograft experiments with human PDAC lines were approved by the HMS Institutional Animal Care and Use Committee (IACUC) under protocol number 04-605. For mouse xenografts, a doxycycline-inducible GOT1 shRNA construct was first generated. For generation of the construct, oligonucleotides to mouse GOT1 shRNA (forward: CCGGCCACAT-GAGAAGACGTTTCTTCTCGAGAAGAAACGTCT-TCTCATGTGTTTG (SEQ ID NO: 19); reverse: AAT-TCAAAAACCACATGAGAAGACGTTTCTTCTCGAGAA GAAACGTCTTCTCATGTGG (SEQ ID NO: 20)) were digested to generate sticky ends (AgeI and EcoRI) and immediately subcloned into the AgeI-EcoRI sites of the pLKO-Tet-on vector. For subcutaneous xenograft, $10^6$ stably infected murine PDAC cells were suspended in 100 μl Hanks Buffered Saline Solution and injected subcutaneously into the lower flank of NCr nude mice (Taconic). Animals were fed with doxycycline water (doxycycline 2 g/L, sucrose 20 g/L) starting on the day of injection or when tumor diameter reached 50 mm. Tumor volumes were measured every third day starting from day 4 post-injection and calculated as above. These xenograft experiments were approved under MDACC IACUC protocol 111113931.

Western Blot Analysis

After SDS-PAGE, proteins were transferred to Hybond-N Nitrocellulose (Amersham Biosciences). Membranes were blocked in Tris-buffered saline (TBS) containing 5% non-fat dry milk and 0.1% Tween 20 (TBS-T), prior to incubation with the primary antibody overnight at 40. The membranes were then washed with TBS-T followed by exposure to the appropriate horseradish peroxidase-conjugated secondary antibody for h and visualized on Kodak X-ray film using the enhanced chemiluminescence (ECL) detection system (Thermo Scientific). The following antibodies were used: Kras (F234, Santa Cruz), GOT1 (NBP1-54778, Novus), GLUD1 (ab55061, Abcam) and β-Actin (A2066, Sigma).

ROS Quantification

The DCFDA assay was performed 24 hr after supplementing Gln-free media with either OAA (4 mM) or dimethyl malate (4 mM). Cells were incubated with 5 μM 2',7'-dichlorodihydrofluorescein diacetate (DCFDA, Invitrogen) for 30 min. Excess DCFDA was removed by washing the cells twice with PBS, and labeled cells were then trypsinized, rinsed, and resuspended in PBS. Oxidation of DCFDA to the highly fluorescent 2',7'-dichloro-fluorescein (DCF) is proportionate to ROS generation and was analyzed by flow cytometry.

Metabolomics

For steady state metabolomic analysis, PDAC cell lines were grown to ~50% confluence in growth medium (DMEM, 2 mM Gln, 10 mM glucose, 10% CCS) on 10 cm tissue culture dishes in biological quadruplicate. A complete medium change was performed two hours prior to metabolite collection. To trace Gln metabolism, PDAC cell lines were grown as above and then transferred into Gln-free DMEM (with 10 mM glucose) containing 10% dialyzed FBS and 2 mM U-$^{13}C_5$-Gln (Cambridge Isotope Labs) overnight (for steady state labeling). Additionally, tissue culture media was replaced with fresh media containing [U-$^{13}C_5$]-Gln 2 hr prior to metabolite extraction for steady state analyses. The quantity of the metabolite fraction analyzed was adjusted to the corresponding protein concentration calculated upon processing a parallel 10 cm tissue culture dish. Metabolite fractions were collected and analyzed by targeted LC-MS/MS via selected reaction monitoring (SRM), as described [Ying, H. et al. (2012) *Cell* 149, 656-670; Yuan, M., et al. (2012) *Nat Protoc* 7, 872-881]. Processed data was analyzed using Cluster 3.0 and TreeViewer software.

Measurement of Sensitization of PDAC Cells to ROS

PDAC cell lines were plated into 96-well plates at $10^3$ cells/well in 200 μL of growth medium. The following day, growth medium was replaced with that containing GLS inhibitors and/or $H_2O_2$. Parallel plates were analyzed at 3, 6 and 9 days by Cell Titer Glo analysis (Promega), per the manufacturer's instruction. The GLS inhibitors 968 (active) and 365 (structurally similar, inactive) were provided as a kind gift from the Cerione laboratory [Wang, J. B. et al. (2010) *Cancer Cell* 18, 207-219]. BPTES was a kind gift from Jaime Escobedo (Forma Therapeutics, Watertown, Mass.).

Lentiviral-Mediated shRNA Targets

All shRNA vectors were obtained from the RNA Interference Screening Facility of Dana Farber Cancer Institute. The RNAi Consortium clone IDs for the shRNAs used in this study are as follows:

```
shGLS-1:
                                     (SEQ ID NO: 21)
GCACAGACATGGTTGGTATAT (TRCN0000051135);

shGLS-2:
                                     (SEQ ID NO: 22)
GCCCTGAAGCAGTTCGAAATA (TRCN0000051136);

shMDH1-1:
                                     (SEQ ID NO: 23)
CCCTGTTGTAATCAAGAATAA (TRCN0000221892);

shMDH1-2:
                                     (SEQ ID NO: 24)
GCAACAGATAAAGAAGACGTT (TRCN0000221893);

shME1-1:
                                     (SEQ ID NO: 25)
GCCTTCAATGAACGGCCTATT (TRCN0000064728);

shME1-2:
                                     (SEQ ID NO: 26)
CCAACAATATAGTTTGGTGTT (TRCN0000064729);

shGLUD1-1:
                                     (SEQ ID NO: 27)
CCCAAGAACTATACTGATAAT (TRCN0000220878);

shGLUD1-2:
                                     (SEQ ID NO: 28)
GCAGAGTTCCAAGACAGGATA (TRCN0000220880);

shGOT1-1:
                                     (SEQ ID NO: 29)
GCGTTGGTACAATGGAACAAA (TRCN0000034784);
```

```
-continued
shGOT1-2:
                                    (SEQ ID NO: 30)
GCTAATGACAATAGCCTAAAT (TRCN0000034785);

shGPT2-1:
                                    (SEQ ID NO: 31)
CGGCATTTCTACGATCCTGAA (TRCN0000035024);

shGPT2-2:
                                    (SEQ ID NO: 32)
CCATCAAATGGCTCCAGACAT;

shPSAT1-1:
                                    (SEQ ID NO: 33)
GCCAAGAAGTTTGGGACTATA (TRCN0000035264);

shPSAT1-2:
                                    (SEQ ID NO: 34)
CCAGACAACTATAAGGTGATT (TRCN0000035265);

shKras-1:
                                    (SEQ ID NO: 35)
CCTCGTTTCTACACAGAGAAA (TRCN0000040148);
and shKras-2:
                                    (SEQ ID NO: 36)
GAGGGCTTTCTTTGTGTATTT (TRCN0000033260).
```

Reagents

NADP+/NADPH ratios were determined using the NADP/NADPH assay kit (Abcam; ab65349) according to the manufacturer's instructions. Briefly, $10^5$ cells (n=6 wells of a 6-well dish) were collected on ice in extraction buffer and subject to two rounds of freeze-thaw at −80° C. NADP+ and NADPH values were determined in biological sextuplet and concentration was obtained by comparison to standard curves. Mitochondrial fractions were obtained as described previously [Son, J. K., et al. (2010) *Cell Death Differ* 17, 1288-1301]. OAA was not analyzed by targeted LC/MS-MS due to its limited stability in aqueous solvents at room temperature [Bajad, S. U. et al. (2006) *J Chromatogr A* 1125, 76-88]. As such, the abundance of this metabolite was determined using a quantification kit (Biovision, Milpitas, Calif.), according the manufacturer's instruction. Briefly, $2\times10^6$ cells (n=4 10 cm tissue culture dishes) were collected during log-phase growth by trypsinization, re-suspended immediately in the buffers provided (on ice), analyzed and compared to standard curves. The signals obtained were normalized to the protein concentration calculated upon processing a parallel 10 cm tissue culture dish. NEAA mixture consisted of a mixture of 0.1 mM glycine, alanine, aspartate, asparagine, proline and serine.

Statistical Analysis

Comparisons were performed using the unpaired Student's t-test. For all experiments with error bars, standard deviation was calculated to indicate the variation within each experiment and data, and values represent mean±standard deviation (s.d.).

Example 2: Dependence of PDAC on Glutamine

This example demonstrates that both glucose and Gln are critical for PDAC growth.

Figure 1B:
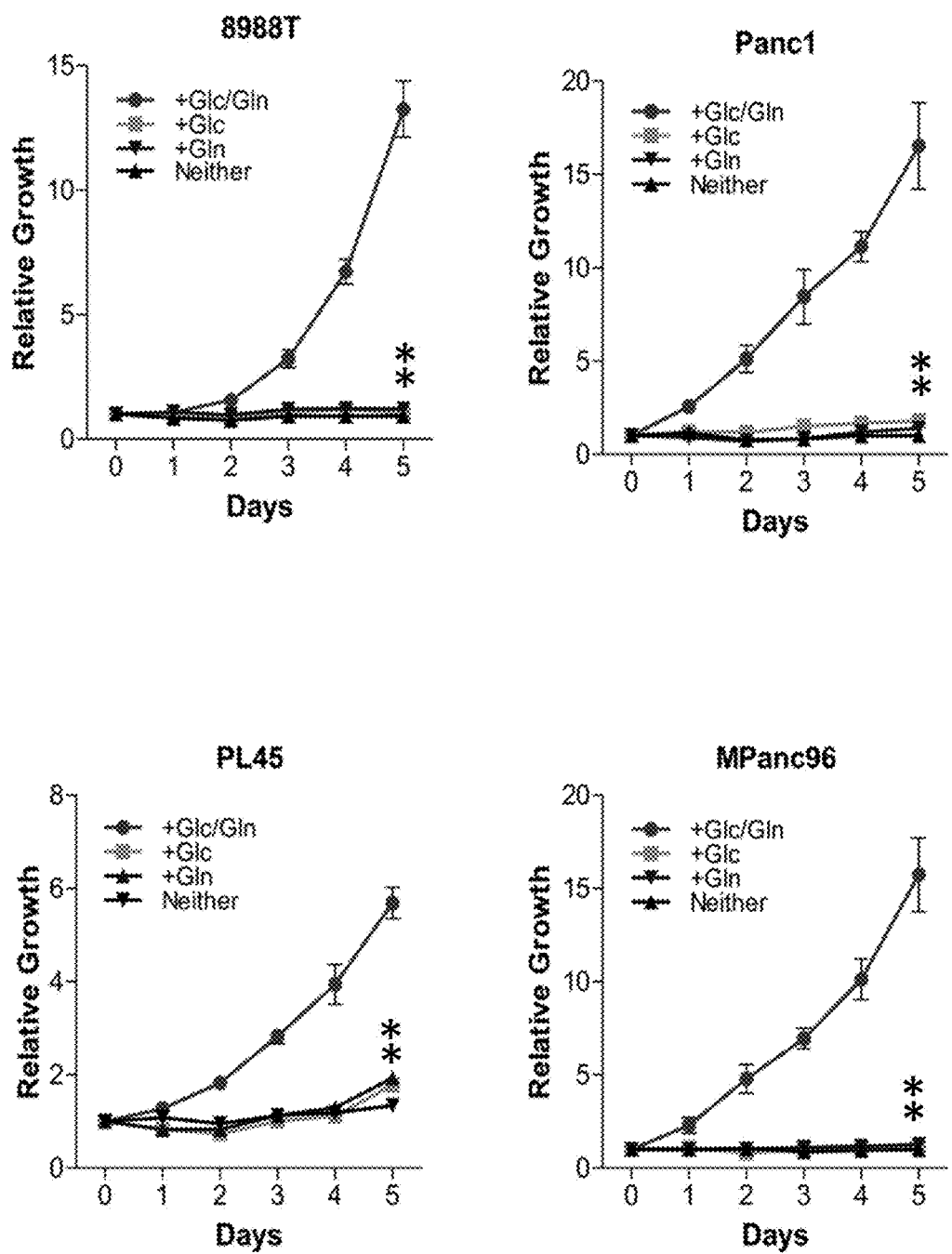
FIG. 1B contains line graphs with the relative growth of the indicated cells types (8988T—upper left quadrant; Panc1—upper right quadrant; PL45—lower left quadrant; MPanc96—lower right quadrant) on the y-axis and the number of days of culture under the indicated conditions on the x-axis. Cells were plated in the complete culture medium (10 mM glucose and 2 mM Gln) which was replaced the following day with glucose-free (+Gln) or Gln-free medium (+Glc), or with Glc-free and Gln-free medium (Neither), or with medium containing both Glc and Gln (+Glc/Gln). In each condition, the medium was supplemented with 10% dialyzed FBS. Error bars represent s.d. (n=3); **, p<0.01.

To explore the dependence of PDAC on glucose and Gln, and, in particular, to examine the functional role of Gln in PDAC tumor metabolism, it was first determined whether glucose and Gln were required for PDAC growth. As expected from previous work [Ying et al. supra, and U.S. provisional application No. 61/578,116], glucose was required for PDAC growth. Additionally, PDAC cells were also profoundly sensitive to Gln deprivation, indicating that Gln is also critical for PDAC growth (FIG. 1A and FIG. 1B).

Figure 2:
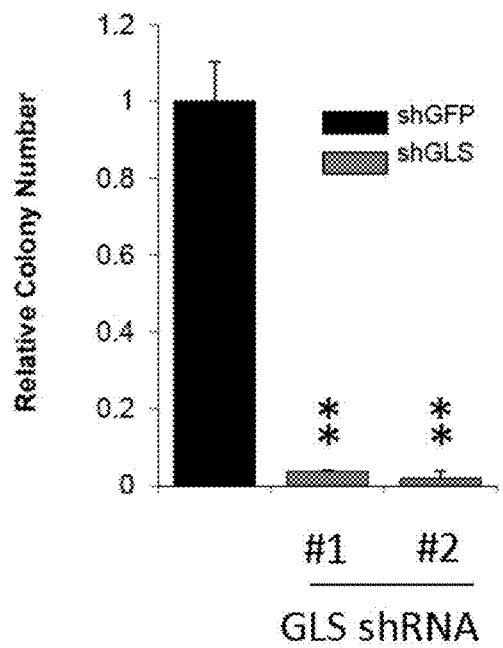
FIG. 2 contains a bar graph showing the relative colony number (clonogenic growth) on the y-axis for each of the indicated groups of 8988T cells expressing a control shRNA (GFP) or two independent shRNAs to GLS (#1 and #2) and cultured in 10 cm tissue culture dishes. Error bars represent s.d. (n=3); **, p<0.01.
Figure 3:
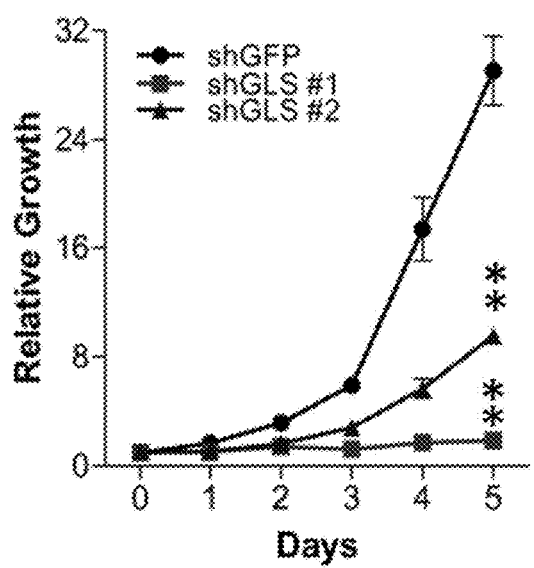
FIG. 3 is a line graph plotting the relative growth of 8988T cells expressing a control shRNA (GFP) or shRNAs to GLS (#1 and #2) on the y-axis versus the number of days of culture on the x-axis. Error bars represent s.d. (n=3); **, p<0.01.

Gln supports tumor cell growth through two primary mechanisms: (i) the glutaminase (GLS)-mediated conversion of Gln into glutamate (Glu) allows for the use of the Gln carbon skeleton in anaplerotic reactions to replenish TCA cycle intermediates, and (ii) the side chain amide of Gln provides nitrogen for nucleotide, nonessential amino acid (NEAA) and hexosamine biosynthesis. To assess the role of Gln metabolism in PDAC growth, GLS activity was impaired genetically, using RNA interference (RNAi). Notably, GLS knockdown markedly reduced PDAC clonogenic growth and proliferation (FIG. 2 and FIG. 3).

Figure 4:
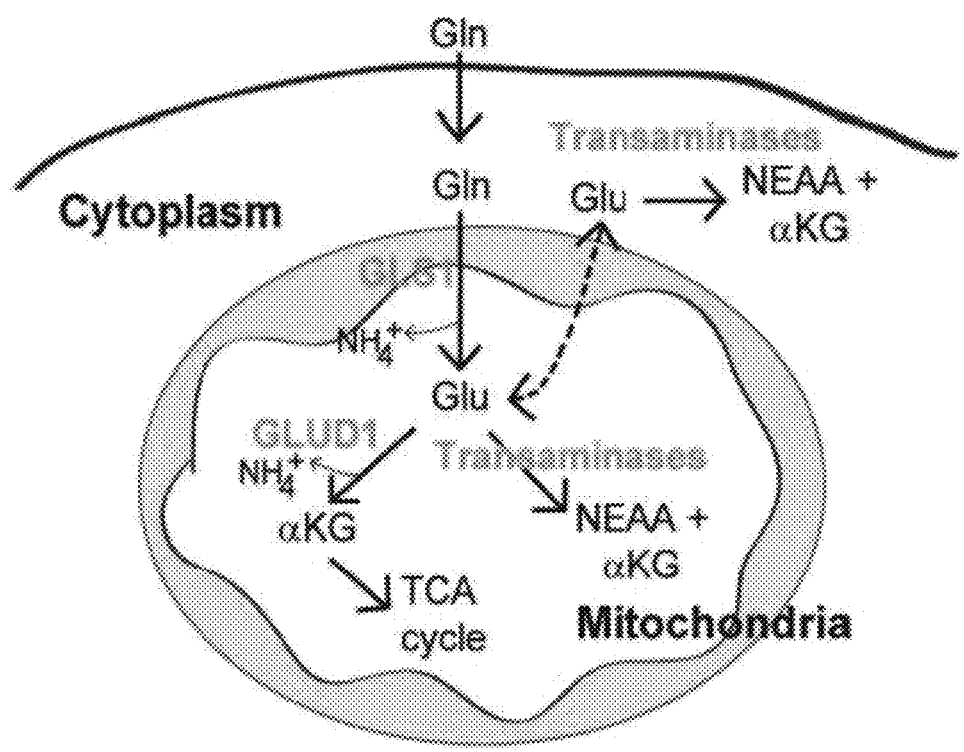
FIG. 4 is a schematic diagram of Gln metabolism. Abbreviations are as follows: Gln: glutamine; Glu: glutamate; αKG: α-ketoglutarate; TCA cycle: tricarboxylic acid cycle; NEAA; nonessential amino acid; GLS: glutaminase; GLUD: glutamate dehydrogenase. The dashed-line arrow indicates transport of glutamate in and out of the mitochondria/cytoplasm; solid-line arrows indicate an enzymatic reaction, and are drawn from the substrate metabolite to the product metabolite of the reaction.
Figure 5:
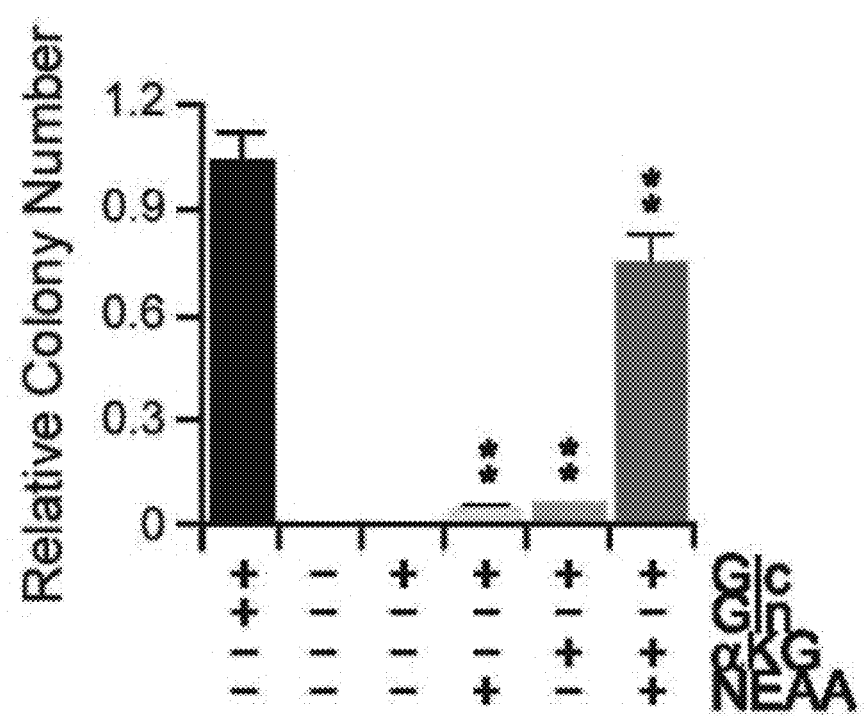
FIG. 5 contains a bar graph showing the relative colony number (clonogenic growth) of 8988T cells cultured in 10 cm dishes in the presence (+) or absence (−) of glucose (Glc), glutamine (Gln), α-ketoglutarate (αKG), and nonessential amino acid (NEAA). Error bars represent s.d. (n=3); **, p<0.01.
Figure 6:
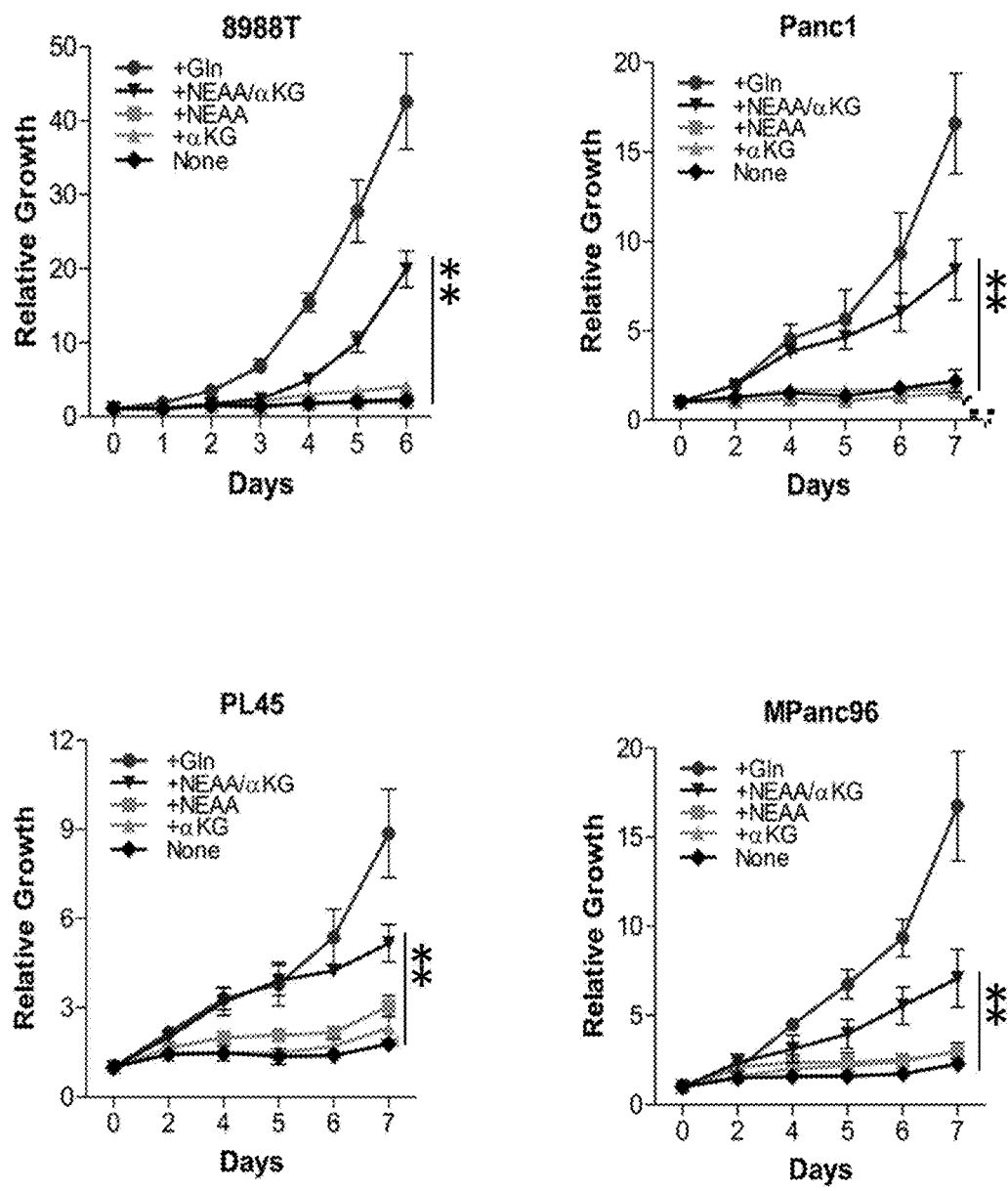
FIG. 6 contains line graphs with the relative growth of the indicated cells types (8988T—upper left quadrant; Panc1—upper right quadrant; PL45—lower left quadrant; MPanc96—lower right quadrant) on the y-axis and the number of days of culture under the indicated conditions on the x-axis following glutamine deprivation. Cells were plated in the complete culture medium (10 mM glucose and 2 mM glutamine (Gln)) which was replaced the following day with glutamine-free medium containing 1×NEAA (+NEAA), or 3 mM of dimethyl αKG (+αKG), or the combination (+NEAA/αKG). One group received medium containing glutamine as a positive control (+Gln) and one group was deprived of glutamine as a negative control (none). Error bars represent s.d. (n=3); **, p<0.01.

The Gln-derived carbon skeleton of Glu plays an important role in replenishing intermediates of the TCA cycle that are precursors for biosynthetic reactions. In particular, Glu can be converted into α-ketoglutarate (αKG) by glutamate dehydrogenase (GLUD1) or by transaminases (FIG. 4). Indeed, many cancer cells rely on GLUD1-mediated Glu deamination to fuel the TCA cycle, and αKG has been shown to be an essential metabolite in Gln metabolism. Therefore, it was next examined whether αKG can rescue cell proliferation upon Gln deprivation. Surprisingly, dimethyl αKG (a cell permeable αKG analog) did not restore growth upon Gln deprivation (FIG. 5). Thus, the combination of αKG and NEAA, which recapitulates the metabolic output of transaminase-mediated Glu metabolism, was next tested. This combination dramatically rescued cell proliferation in multiple PDAC lines (FIG. 5 and FIG. 6), indicating that PDAC cells may metabolize Gln in a manner different from canonical models. Furthermore, as transaminases catalyze a reaction that generates both NEAA and αKG, the metabolite rescue data suggested that this class of enzymes may be critical for Gln metabolism in PDAC.

Example 3: Identification of a Non-Canonical Pathway of Glutamine Metabolism in PDAC This example identifies a novel pathway of glutamine metabolism in PDAC that involves the enzymes GOT1, MDH1 and ME1.

Figure 7A:
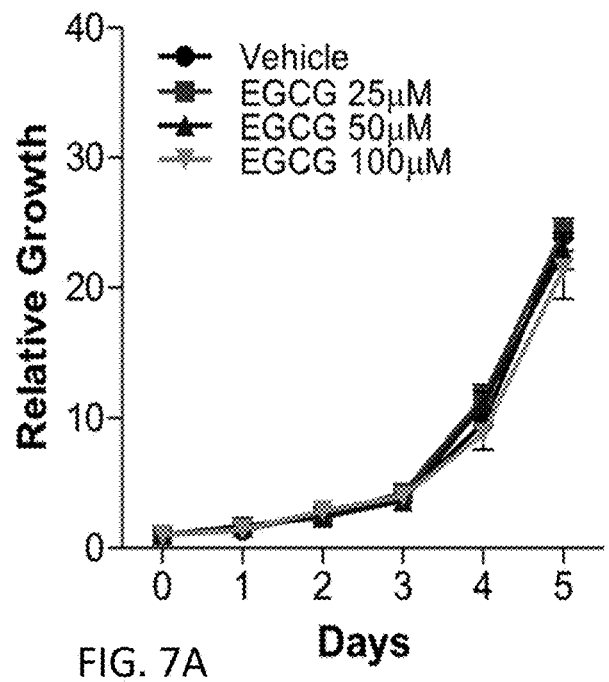
FIGS. 7A and 7B contain line graphs plotting relative growth of 8988T cells treated with the indicated concentration of either EGCG (Epigallocatechin Gallate)) (FIG. 7A) or AOA (aminooxyacetate (FIG. 7B) or vehicle and assayed for cell growth. The number of days of culture is shown on the x-axis; error bars represent s.d. (n=3); **, p<0.01.
Figure 7B:
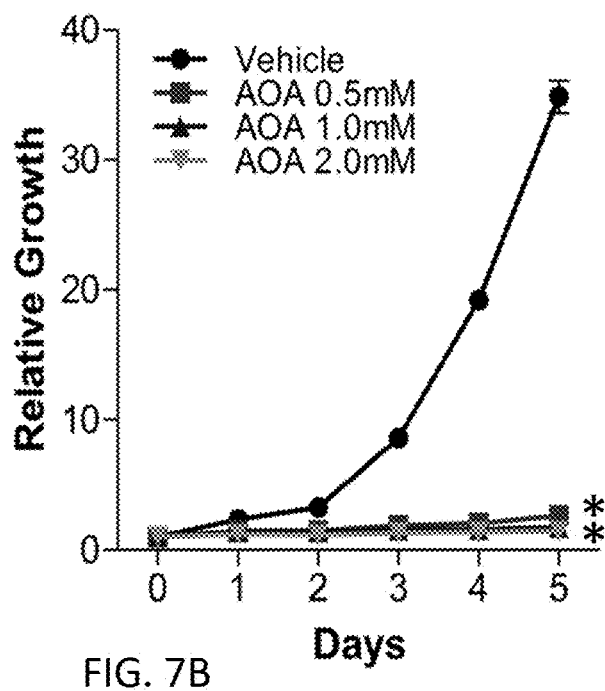
Figure 8:
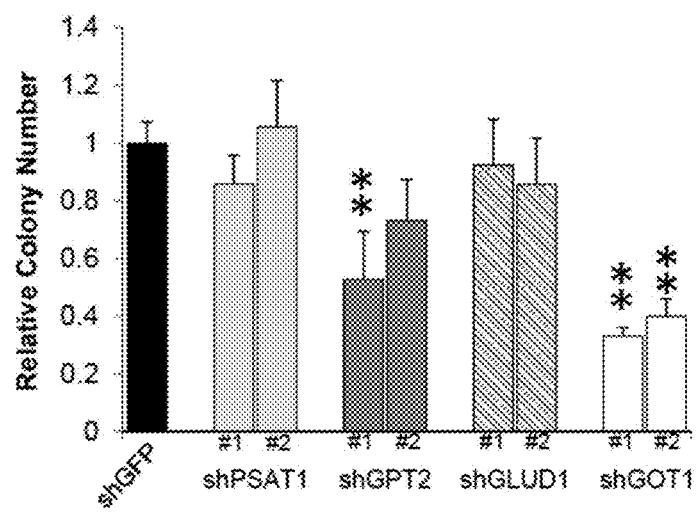
FIG. 8 contains a bar graph showing the relative colony number (clonogenic growth) of 8988T cells expressing a control shRNA (shGFP) or two independent shRNAs to PSAT1 (#1 and #2); GPT2 (#1 and #2); GLUD1 (#1 and #2); and GOT1 (#1 and #2) cultured in 10 cm tissue culture dishes. Error bars represent s.d. (n=3); **, p<0.01.

PDAC cells were treated with aminooxyacetate (AOA), a potent inhibitor of transaminases [Wise, D. R. et al. (2008) *Proc Natl Acad Sci USA* 105, 18782-18787]. In parallel, Epigallocatechin Gallate (EGCG), an antioxidant and inhibitor of GLUD, was also utilized. Previously, it was shown that EGCG (but not AOA) could inhibit the proliferation of tumor cells driven by mTOR activation, indicating that GLUD1 is essential to Gln metabolism in this setting. However in a fibroblast system with overexpression of mutant Kras, both transaminases and GLUD1 were critical for cell growth. In contrast, it was found that EGCG (FIG. 7A) had little effect on PDAC growth, whereas AOA (FIG. 7B) treatment robustly inhibited the growth of PDAC cells. Consistent with these results, GLUD1 knockdown also had no effect on PDAC growth (FIG. 8). Together, these data indicates that oncogene-induced metabolic alterations are context dependent with PDAC relying predominantly on transaminases for growth.

Figure 9:
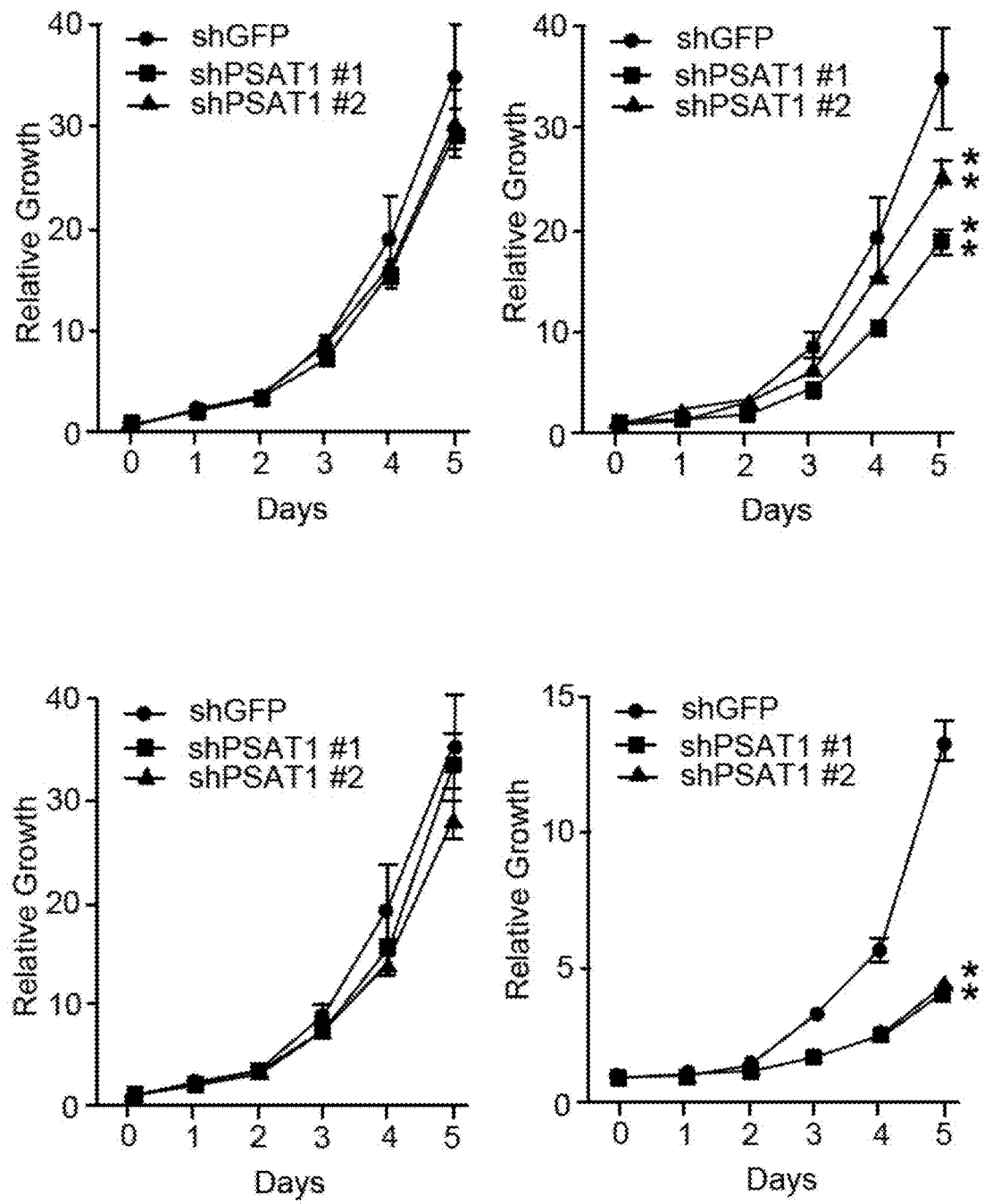
FIG. 9 contains line graphs plotting the relative growth of 8988T cells expressing a control shRNA (GFP), or shRNAs to PSAT1 (#1 and #2) (upper left quadrant); shRNAs to GPT2 (#1 and #2) (upper right quadrant); shRNAs to GLUD1 (#1 and #2) (lower left quadrant), or shRNAs to GOT1 (#1 and #2) (lower right quadrant) versus the number of days of culture on the x-axis; error bars represent s.d. (n=3); **, p<0.01.
Figure 10:
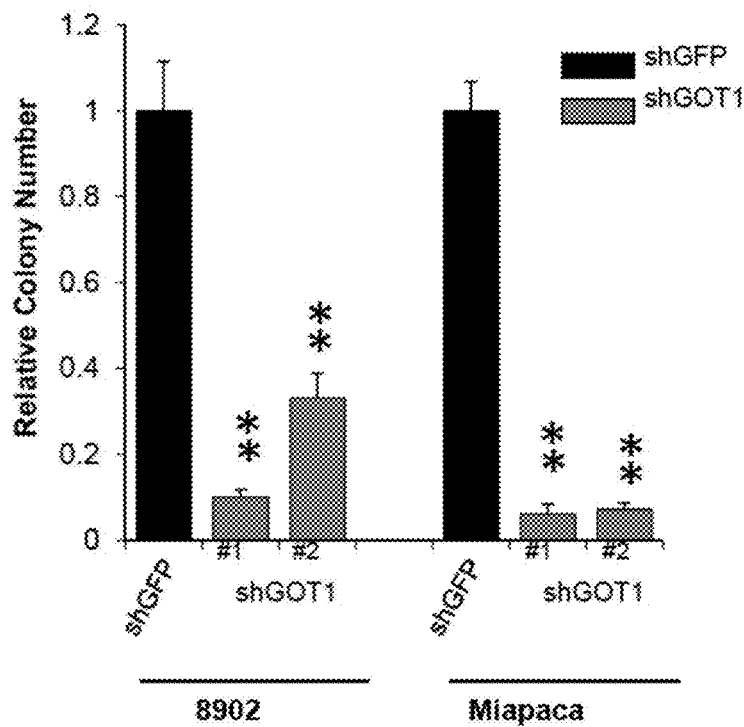
FIG. 10 contains a bar graph plotting the relative clonogenic growth of 8902 or Miapaca pancreatic cancer cells expressing a control shRNA (shGFP) or shRNAs to GOT1 (#1 and #2) cultured in 10 cm tissue culture dishes. Error bars represent s.d. (n=3); **, p<0.01.
Figure 11A:
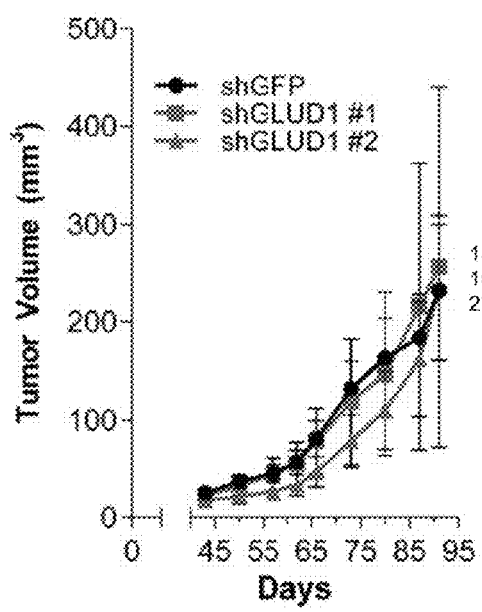
FIG. 11A is a line graph plotting the xenograft growth (expressed as tumor volume (mm$^3$)) of 8988T cells expressing a control shRNA (shGFP) or shRNAs targeting GLUD1 (#1 and #2) in mice (n=10). The numbers to right of graph represent the knockdown efficiency of shRNAs measured before injecting the cells into mice; error bars represent s.e.m. (n=10).
Figure 11B:
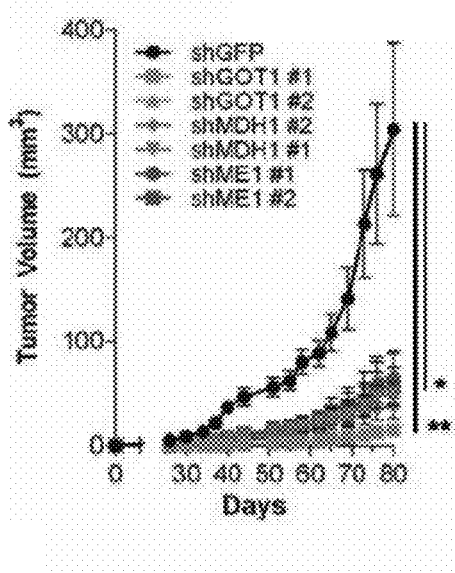
FIG. 11 is a line graph plotting the xenograft growth (expressed as tumor volume (mm$^3$)) of 8988T cells expressing a control shRNA (shGFP), shRNAs to GOT1 (#1 and #2), MDH1 (#1 and #2) or ME1 (#1 and #2) in mice; error bars represent s.e.m. (n=10); *, p<0.05; **, p<0.01.

Next, to identify the specific transaminases involved in PDAC Gln metabolism, each of the Glu-dependent transaminases (aspartate, alanine and phosphoserine transaminase) was inhibited individually using RNAi and the effect on PDAC growth was examined. Interestingly, knockdown of the aspartate aminotransferase, GOT1, had the most significant impact on PDAC growth (FIG. 8 and FIG. 9), and these observations were reproducible in multiple PDAC cell lines (FIG. 10). As further confirmation of the importance of this pathway in PDAC. GOT1, GLUD1, MDH1, and ME1 expression was suppressed using two lentiviral shRNAs in PDAC cells and the cells' ability to grow as xenografts was assessed. Consistent with in vitro results, both GLUD1 shRNAs had no effect on tumor growth (FIG. 11A). In contrast, GOT1, MDH1, and ME1 knockdown each robustly diminished tumor growth (FIG. 11A and FIG. 11B). These data provide further support for the critical role of this pathway in Gln metabolism and PDAC tumor growth.

Figure 12:
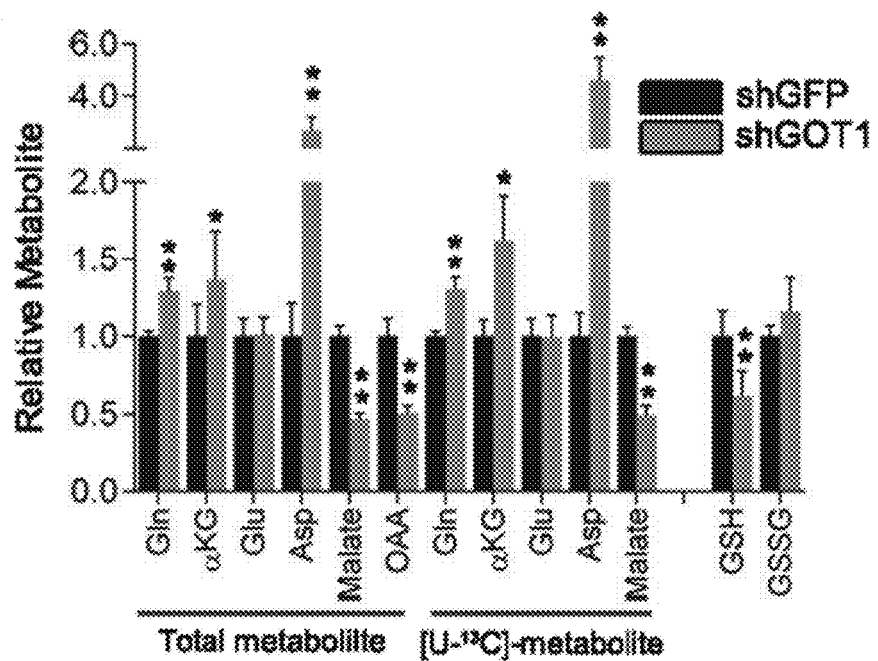
FIG. 12 is a bar graph plotting the relative metabolite abundance of 8988T cells grown in U-$^{13}$C Gln upon GOT1 knockdown and presented as those derived from Gln (U-$^{13}$C) or total metabolite pools ($^{12}$C+U-$^{13}$C) ("total metabolite"). shGFP was used as a control. Abbreviations are as follows: glutamine (Gln); α-ketoglutarate (αKG), glutamate (Glu); aspartate (Asp); oxaloacetate (OAA); reduced glutathione (GSH); oxidized glutathione (GSSG). Error bars represent s.d. (n=3); *, p<0.05; **, p<0.01.
Figure 13:
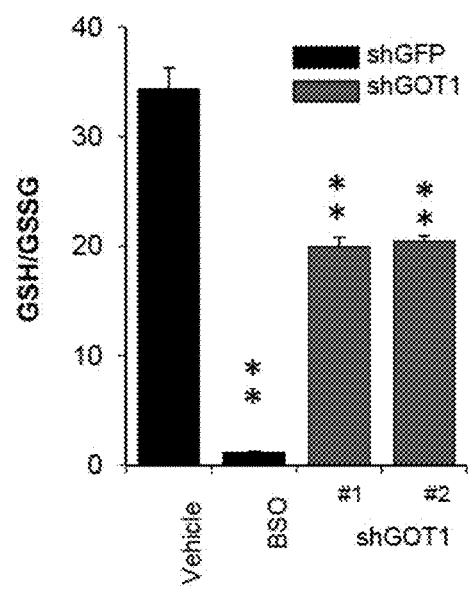
FIG. 13 is a bar graph plotting the ratio of reduced to oxidized glutathione (GSH/GSSG) in 8988T cells expressing a control shRNA (shGFP) or a GOT1 shRNA (#1 or #2) as measured in a biochemical assay. In the shGFP groups, BSO (buthionine sulfoximine) was included as a positive control for GSH depletion. Error bars represent s.d. (n=3); **, p<0.01.

Next, the direct effects of GOT1 knockdown on Gln metabolism were explored. Toward this end, targeted liquid chromatography-tandem mass spectrometry (LC-MS/MS) based metabolomic analysis in GOT1 knockdown PDAC cells was performed using uniformly-labeled $^{13}C_5$-Gln ($U^{13}$-Gln) as a tracer [Ying et al. supra; Yuan et al. supra]. GOT1 catalyzes the conversion of aspartate (Asp) and αKG into OAA and Glu in the cytoplasm. Based on the functional data, it was speculated that GOT1 knockdown would lead to an increase in Asp and a decrease in OAA. Indeed, GOT1 knockdown led to increased Gln-derived Asp (and total Asp) and decreased OAA. Interestingly, a significant decrease in the ratio of reduced-to-oxidized glutathione (GSH:GSSG) was also observed (FIG. 12 and FIG. 13), demonstrating that GOT1 plays a role in the maintenance of cellular redox homeostasis.

One mechanism by which cells maintain redox homeostasis is through the shunting of glucose into the oxidative arm of the PPP, which generates cellular reducing power in the form of NADPH. In PDAC, it was recently demonstrated that glucose is not used to generate NADPH through the PPP, and, moreover, that glucose metabolism has minimal effects on the redox state in PDAC [Ying et al. supra, and U.S. provisional application No. 61/578,116]. Therefore, it was speculated that the GOT1-mediated conversion of Gln into OAA, via Asp, may facilitate the downstream production of NADPH.

Figure 14:
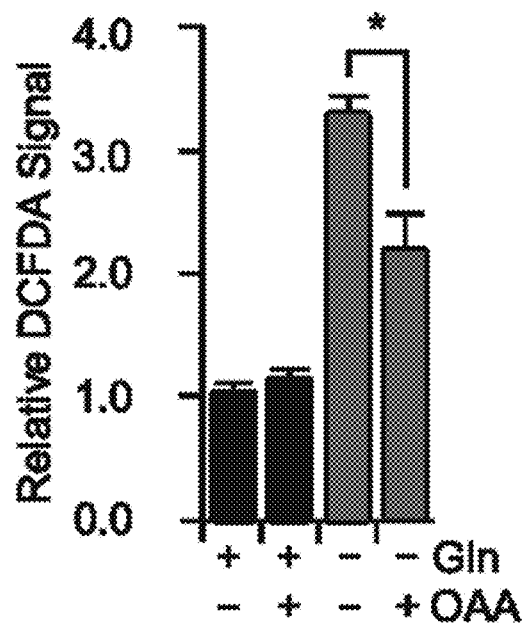
FIGS. 14-17 contain bar graphs plotting the relative ROS (reactive oxygen species) levels (expressed as DCFDA signal) of 8988T cells expressing a control shRNA (shGFP) or a GOT1 shRNA (shGOT1) and cultured under the indicated conditions: with (+) or without (−) glutamine (Gln), oxaloacetate (OAA), and/or malate, as indicated. Each bar represents the mean of three separate experiments; *, p<0.05.
Figure 15:
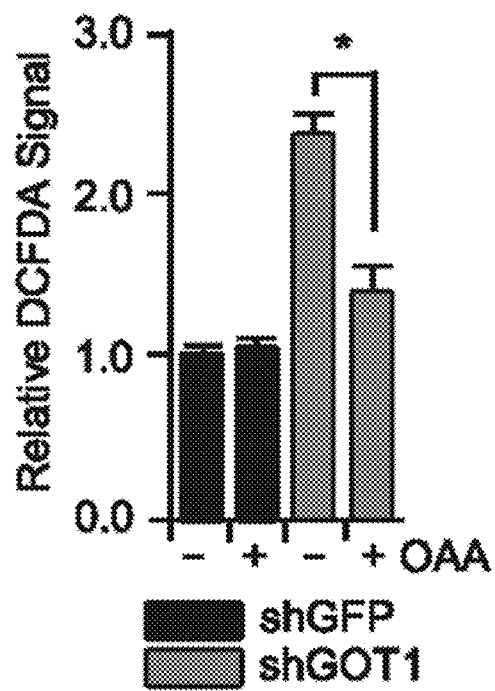

To test this hypothesis, ROS levels were assessed upon Gln deprivation in the absence or presence of OAA. Indeed, it was found that Gln deprivation induced ROS and that OAA could rescue the elevated ROS levels caused by Gln deprivation (FIG. 14). Consistent with this result, GOT1 knockdown also increased ROS levels, which again were restored upon medium supplementation with OAA (FIG. 15). These results demonstrate that GOT1-mediated OAA production from Gln is required for the regulation of ROS.

Figure 16:
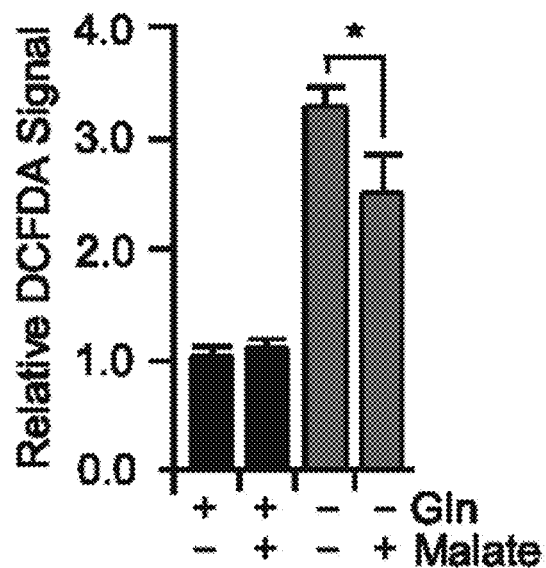
Figure 17:
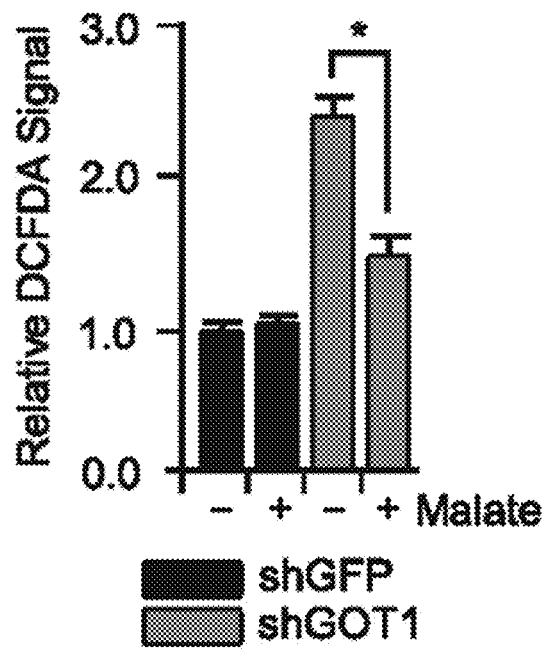
Figure 18:
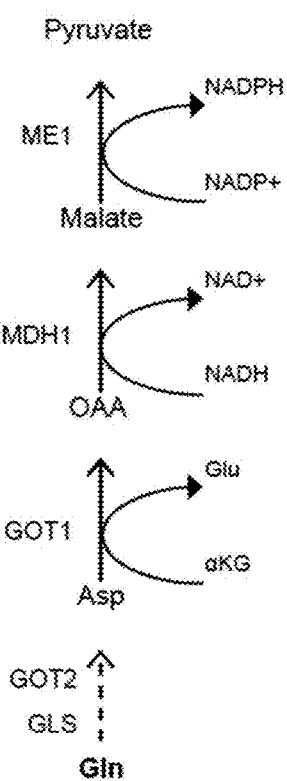
FIG. 18 is a schematic diagram of the pathway by which pyruvate is derived from Gln (in a pathway termed the "glutamine to pyruvate pathway (GPP)"). The dashed-line straight arrow indicates multiple enzymatic reactions; solid-line straight arrow indicates a single enzymatic reaction; curved arrows represent the conversion of additional substrates of the indicated reactions to the listed metabolites.
Figure 19A:
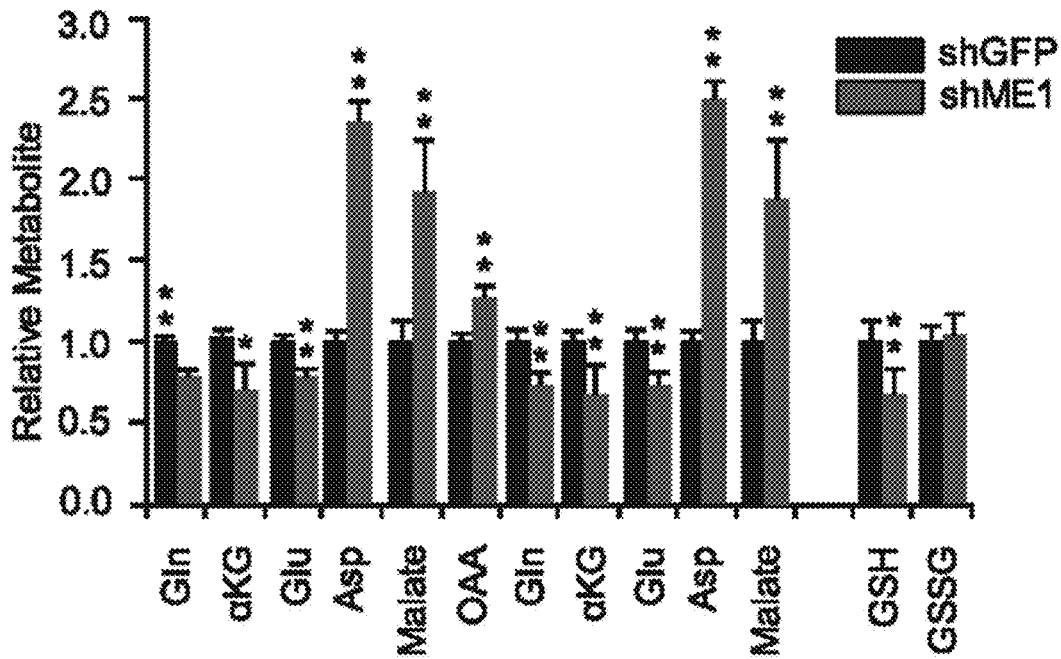
FIG. 19A is a bar graph plotting the relative metabolite abundance in 8988T cells grown in U-$^{13}$C Gln upon ME1 knockdown with shME1 and presented as those metabolites derived from Gln (U-$^{13}$C) or total pools ($^{12}$C+U-$^{13}$C). shGFP was used as a control. Abbreviations are as follows: glutamine (Gln); α-ketoglutarate (αKG), glutamate (Glu); aspartate (Asp); oxaloacetate (OAA); reduced glutathione (GSH); oxidized glutathione (GSSG). Error bars represent s.d. (n=3); *, p<0.05; **, p<0.01.
Figure 19B:
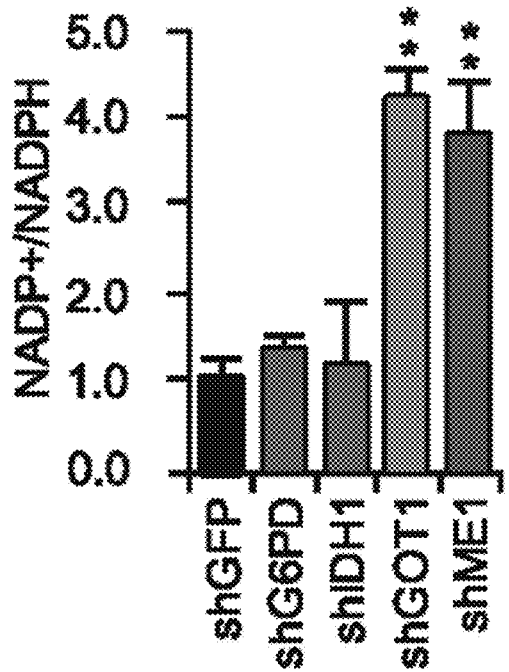
FIG. 19B is a bar graph plotting the NADP1/NADPH ratio in 8988T cells expressing a control shRNA(shGFP), or an shRNA to G6PD, IDH1 (G6PD or isocitrate dehydrogenase), GOT1 or ME1; error bars represent s.d. of six replicate wells from a representative experiment; **p<0.01.

Given the observation that Gln-derived malate (and total malate) was significantly reduced upon GOT1 knockdown (FIG. 12), it was speculated that Gln-derived OAA is metabolized into malate, which is ultimately utilized by malic enzyme (ME1) to create NADPH, which would provide reducing power to maintain pools of reduced glutathione (GSH) necessary for redox homeostasis. Consistent with this notion, malate rescued the oxidative stress imposed by Gln-deprivation (FIG. 16) and GOT1 knockdown (FIG. 17). Collectively, these data are consistent with a model whereby Gln-derived Asp is converted by GOT1 into OAA. This OAA is then converted into malate by malate dehydrogenase (MDH1) and subsequently oxidized by ME1 into pyruvate and NADPH (FIG. 18). Consistent with this pathway, metabolomic analysis of $U^{13}$-Gln tracing in ME1 knockdown cells revealed a significant increase in Asp, malate and OAA and decreased GSH (FIG. 19A). Furthermore, knockdown of GOT1 and ME1 markedly increased the cellular NADP+/NADPH ratio, whereas inhibition of other cytosolic sources of NADPH (G6PD or isocitrate dehydrogenase, IDH1) had no effect on NADP+/NADPH ratios (FIG. 19B) or ROS. Together the data suggest that PDAC utilize Gln through the pathway depicted in FIG. 18 to increase the NADPH/NADP+ ratio for maintenance of redox homeostasis. Lastly, Gln tracing kinetic flux experiments in GOT1 knockdown cells clearly demonstrate decreased flux through this pathway. Interestingly, lactate labeling in the $^{13}C$-labeling experiments was typically at very low levels, indicating that the pyruvate produced by ME1 is not utilized to make lactate by lactate dehydrogenase.

Example 4: Role of GOT1, MDH1 and ME1 in PDAC

This example demonstrates that GOT1, MDH1 and ME1 activity is required in PDAC cells but not normal cells for redox homeostasis and cell proliferation.

Figure 20A:
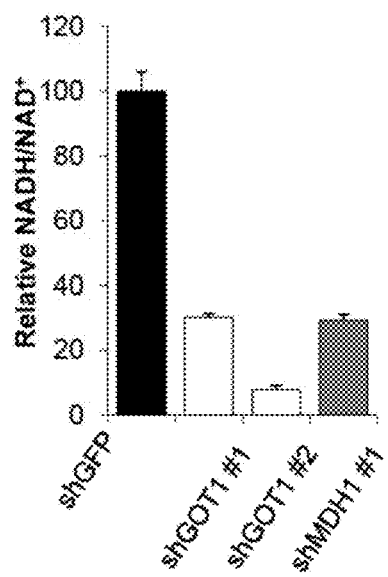
FIGS. 20A and 20B are bar graphs plotting the mitochondrial NADH/NAD+ ratio (FIG. 20A) and the oxidative phosphorylation, as measured by oxygen consumption (FIG. 20B) determined in 8988T cells expressing a control shRNA (GFP), shRNAs to GOT1 (#1 and #2) or MDH1 (#1) or GLUD (#1 and #2), as indicated; error bars represent s.d. (n=3); *, p<0.05.
Figure 20B:
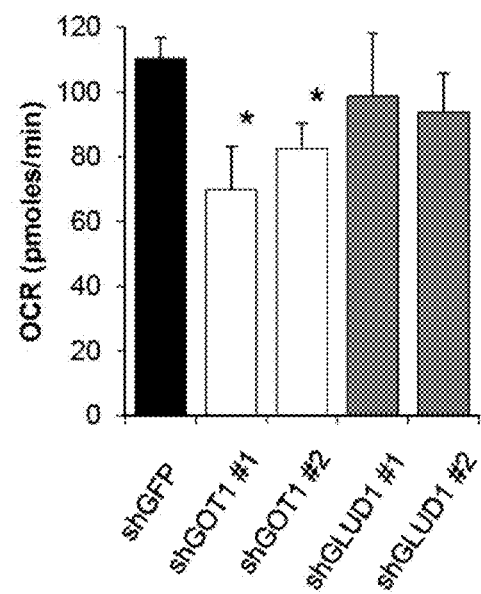
Figure 20C:
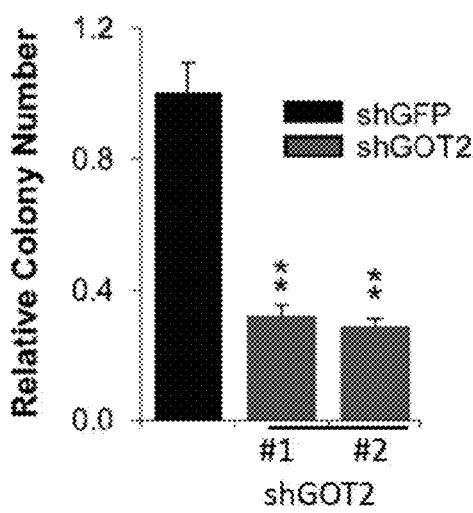
FIG. 20C is a bar graph quantifying the relative clonogenic growth of 8988T expressing a control shRNA (shGFP) or shRNAs to GOT2 (#1 and #2); error bars represent s.d. of triplicate wells from a representative experiment. **, p<0.01.
Figure 20D:
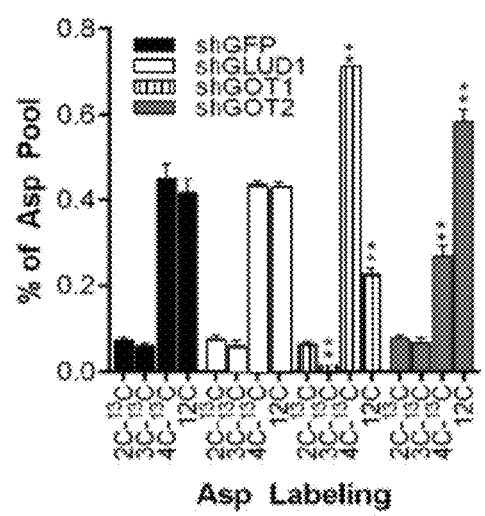
FIG. 20D is a bar graph quantifying the fraction of the total metabolite pool that is unlabeled ($^{12}$C), $^{13}$C-labeled on 2 carbons ($^{2}$C-$^{13}$C), 3 carbons ($^{3}$C-$^{13}$C) or uniformly labeled ($^{4}$C-$^{13}$C), as determined by Asp isotopomer analysis following GLUD1, GOT1 or GOT2 knockdown, as compared to shGFP control.
Figure 20E:
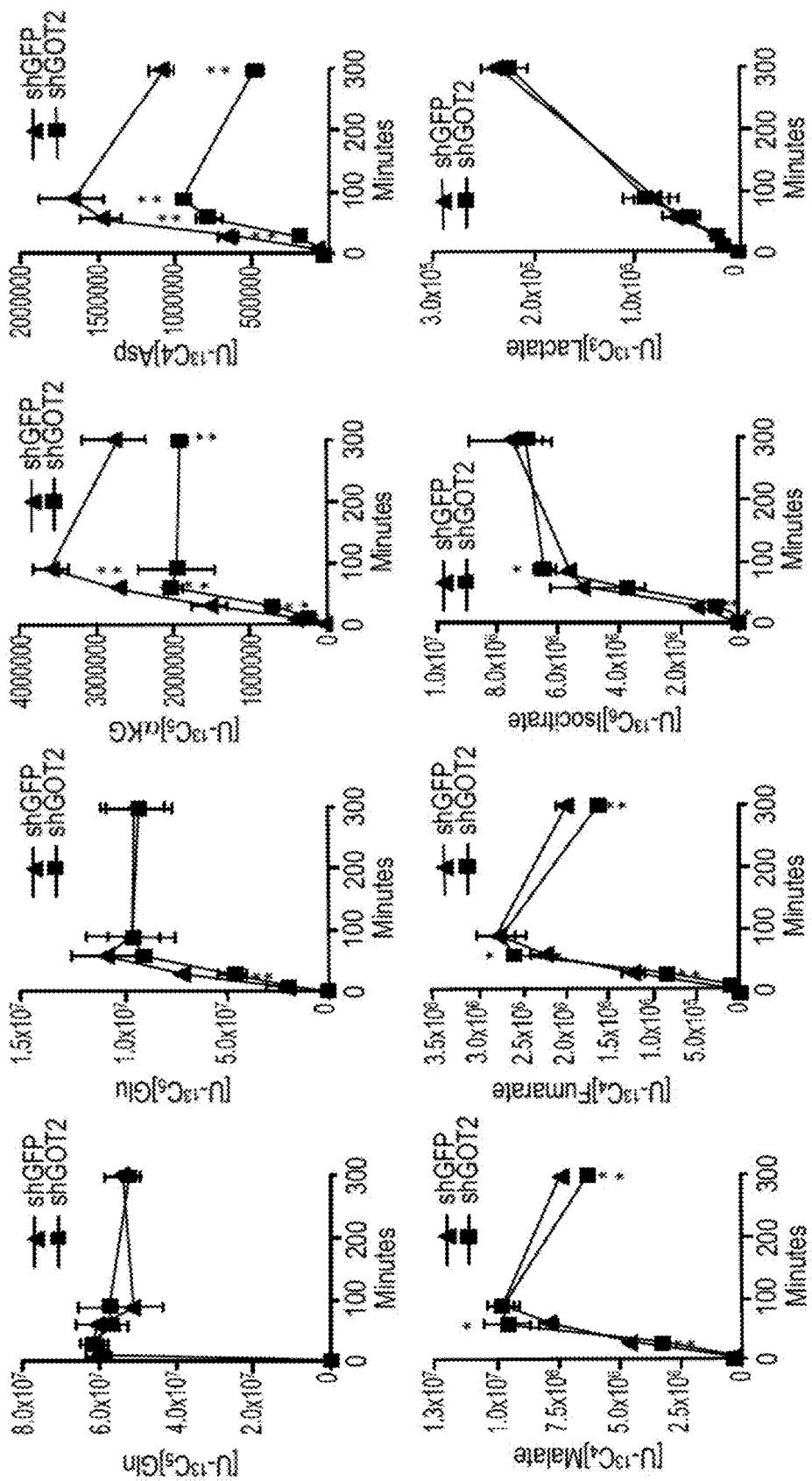
FIG. 20E contains line graphs plotting the flux of the Gln carbon skeleton into downstream metabolites as a function of time. Reads for ion current for [U-$^{13}$C]-labeled metabolites are plotted for cells expressing a control shRNA (shGFP) or shRNA to GOT2; error bars represent the s.d. of three independently prepared samples. *, p<0.05; **, p<0.01.

The canonical role of GOT1 is to facilitate the shuttling of electrons from cytosolic NADH (produced during glycolysis) into the mitochondria for oxidative phosphorylation. Thus, it was speculated that GOT1 knockdown may result in decreased oxidative phosphorylation. To test this hypothesis, the mitochondrial NADH/NAD+ ratio and the oxygen consumption rate (OCR) were measured. It was observed that both the mitochondrial NADH/NAD+ ratio and oxygen consumption were significantly decreased upon GOT1 knockdown (FIG. 20A, FIG. 20B), demonstrating that the GOT1-mediated conversion of Gln-derived Asp into OAA and then malate allows PDAC cells to simultaneously provide NADH for oxidative phosphorylation while generating NADPH to maintain redox homeostasis. The majority of Asp in PDAC cells (50-75%) is derived from Gln, as evidenced by $^{13}C$-labeling (FIG. 20C). In principle, uniformly $^{13}C$-labeled Asp can be derived from Gln following either (i) the GLUD1-mediated conversion of Glu to αKG (and its subsequent traversing through the TCA cycle) or (ii) the mitochondrial aspartate transaminase (GOT2)-mediated conversion of Glu and OAA to αKG and Asp. Of these two enzymes, only GOT2 knockdown significantly impacted PDAC growth (FIG. 20C). Consistent with this observation, GLUD1 knockdown did not affect Asp biosynthesis from Gln, whereas GOT2 knockdown resulted in a significant decrease in Gln-derived Asp in PDAC cells (FIGS. 20D, 20E).

Figure 21A:
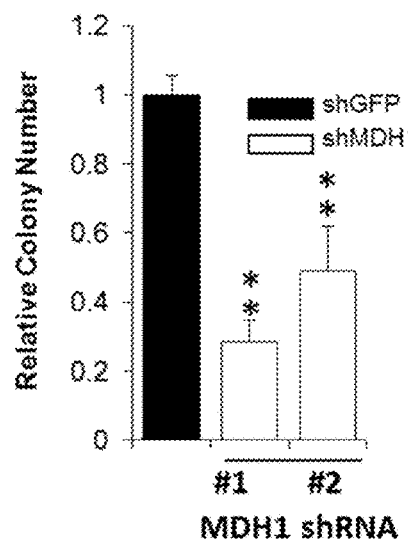
FIGS. 21A and 21B contain bar graphs plotting the relative clonogenic growth of 8988T cells expressing a control shRNA (shGFP) or shMDH1 (#1 or #2) or shME1 (#1 or #2) and cultured in 10 cm tissue culture dishes; error bars represent s.d. (n=3); **, p<0.01.
Figure 21B:
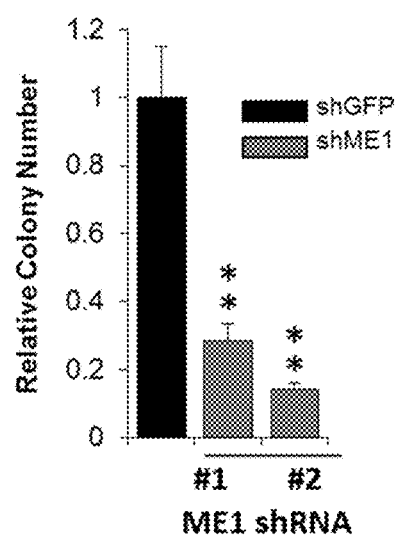

Since GOT1 is required to support PDAC growth, potentially through mechanisms involving redox balance, it was next tested whether other components of this pathway are also required to sustain PDAC growth. Indeed, both MDH1 and ME1 knockdown also dramatically inhibited clonogenic survival of PDAC cells (FIG. 21A, FIG. 21B) in a manner similar to GOT1 knockdown (FIG. 8, 11).

Figure 22:
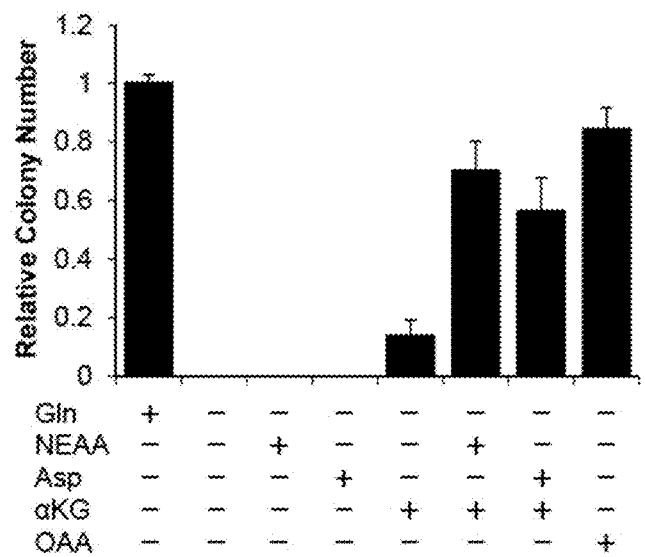
FIG. 22 is a bar graph plotting the relative colony number (clonogenic growth) of 8988T cells plated in complete culture medium (10 mM glucose and 2 mM Gln) which was replaced the following day with Gln-free medium supplemented with the indicated combinations (with (+) or without (−)) of nonessential amino acid (NEAA), aspartate (Asp) (2 mM), α-ketoglutarate (αKG) (4 mM) or oxaloacetate (OAA) (4 mM); error bars represent s.d. (n=3).
Figure 23:
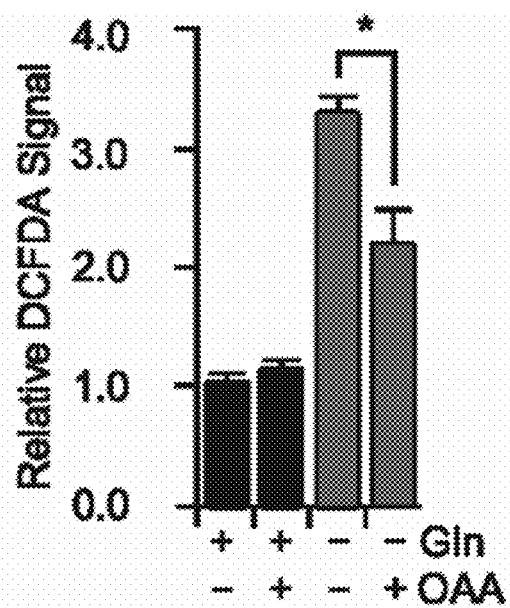
FIG. 23 is a bar graph plotting the relative colony number (clonogenic growth) of 8988T cells cultured in 10 cm tissue culture dishes under the indicated conditions: with (+) or without (−) glutamine (Gln) and oxaloacetate (OAA); error bars represent s.d. (n=3); *, p<0.05.
Figure 24:
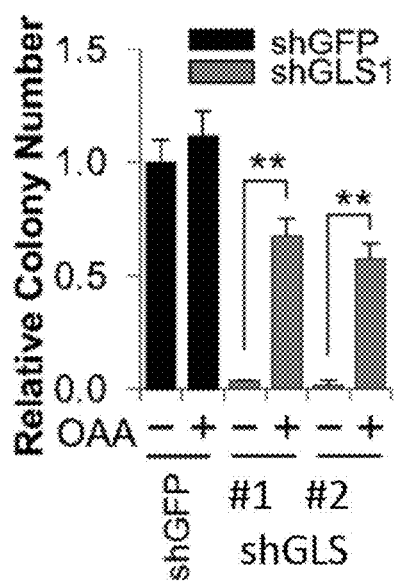
FIG. 24 contains a bar graph plotting the relative colony number (clonogenic growth) of 8988T cells expressing a control shRNA (shGFP) or shRNAs to GLS (#1 and #2) and cultured in complete medium supplemented with (+) or without (−) oxaloacetate (OAA), as indicated; error bars represent s.d. (n=3); **, p<0.01.
Figure 25:
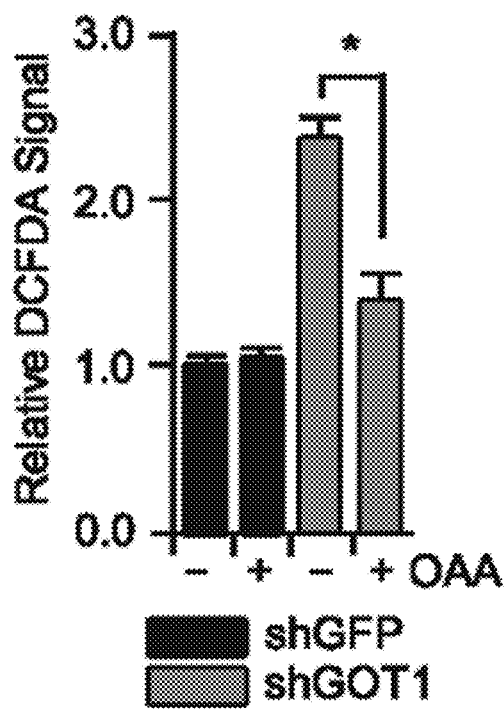
FIG. 25 is a bar graph plotting the relative ROS levels in 8988T cells under conditions indicated as determined by DCFDA (29,79-dichlorodihydrofluorescein diacetate) staining. DCFDA assay was performed 24 h after supplementing Gln-free media with OAA (4 mM). Each bar represents the mean of three independent experiments with error bars representing the s.d.;*, p<0.05.
Figure 26:
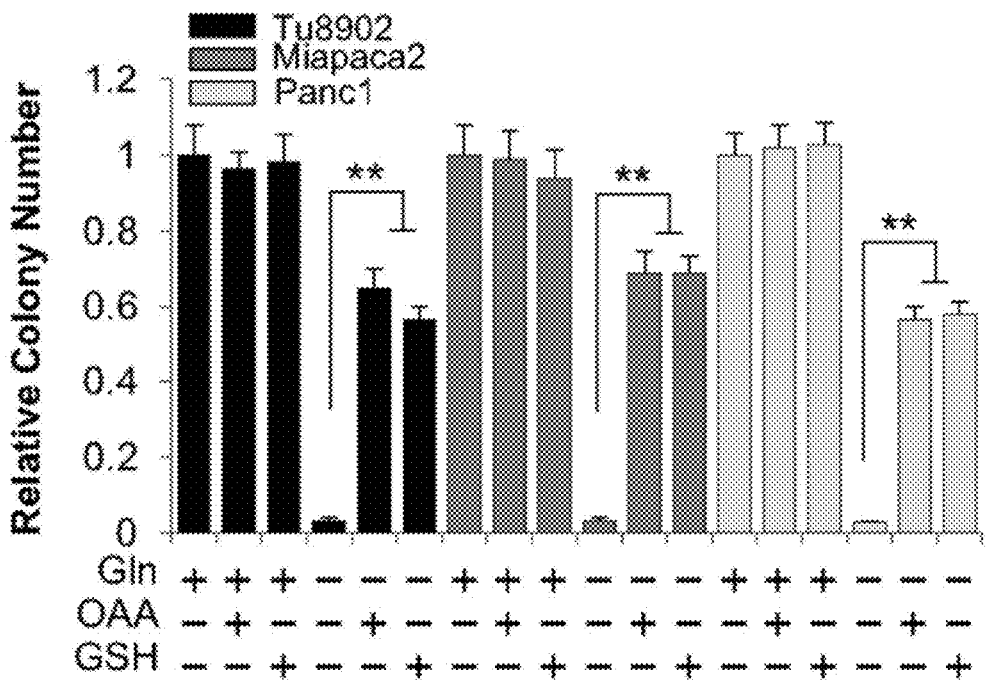
FIG. 26 contains a bar graph plotting the relative clonogenic growth of Tu8902, Miapaca2 and Panc1 cells. OAA (4 mM) or GSH (4 mM) was added (indicated by "+") to media after Gln-withdrawal (indicated by "−"); error bars represent s.d. of triplicate wells from a representative experiment. **, p<0.01.
Figure 27:
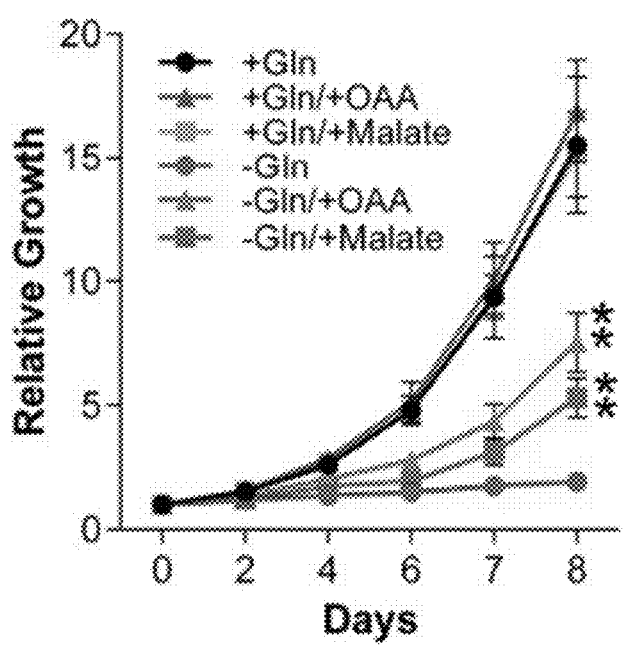
FIG. 27 is a line graph plotting the relative growth of 8988T cells plated in complete culture media, which was replaced the following day with Gln-free medium containing dimethyl-malate (4 mM) or OAA (4 mM). Error bars represent s.d. of triplicate wells from a representative experiment. **, p<0.01.
Figure 28:
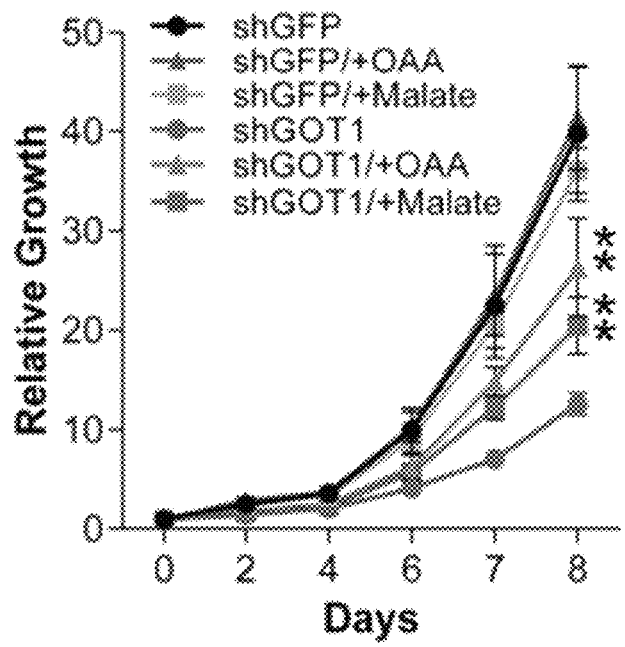
FIG. 28 is a line graph plotting the relative growth of 8988T cells expressing a control shRNA (shGFP) or shRNAs targeting GOT1, which were plated in the complete culture media with or without dimethyl-malate (4 mM) or OAA (4 mM) and assayed for proliferation; error bars represent s.d. of triplicate wells from a representative experiment; **, p<0.01.

The ability of the combination of the GOT1 substrates Asp and αKG to rescue PDAC cell growth upon Gln deprivation was assessed. Indeed, this combination robustly rescued cell growth in Gln-free conditions (FIG. 22). It was speculated that the GOT1-mediated conversion of Gln-derived Asp into OAA functions in a pathway that is used to generate the NADPH which could be used to maintain redox balance. To test this hypothesis, ROS levels were assessed upon Gln deprivation in the absence or presence of OAA. Gln deprivation induced ROS and OAA could partially rescue the elevated ROS levels (FIG. 23). Additionally, OAA permitted PDAC growth under Gln-free conditions in multiple PDAC cell lines (FIG. 26) as well as upon both GLS (FIG. 24) and GOT1 knockdown. GOT1 knockdown also increased ROS levels, which again were significantly restored upon supplementation with OAA (FIG. 25). Lastly, the addition of dimethyl-malate was able to partially rescue PDAC cell growth upon Gln deprivation (FIG. 27) or GOT1 knockdown (FIG. 28).

Example 5: PDAC Use the GPP to Generate Reducing Power

This example demonstrates that OAA- or malate-mediated rescue of PDAC growth upon Gln deprivation is via the generation of reducing potential.

Figure 29:
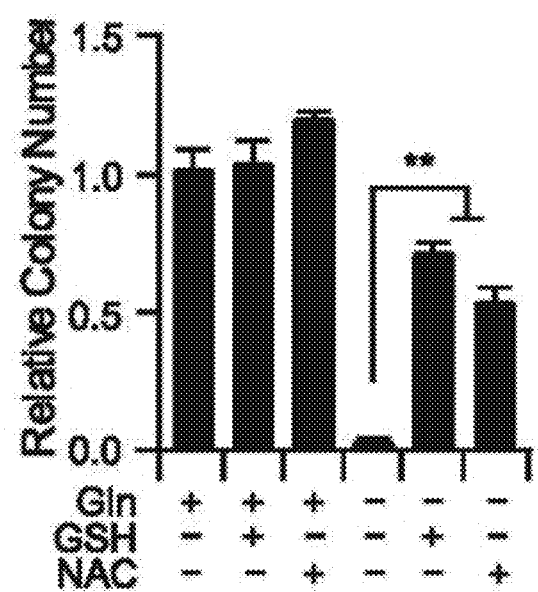
FIG. 29 contains a bar graph plotting the relative clonogenic growth of 8988T cells under conditions indicated. Cells were plated in complete culture media (10 mM glucose and 2 mM Gln), which was replaced the following day with Gln-free medium supplemented with OAA (4 mM), GSH (4 mM) or N-acetylcysteine (NAC) (4 mM); error bars represent s.e.m. (n=10); **, p<0.01.

Cells grown in Gln-free conditions were treated with cell permeable GSH. Remarkably, the addition of GSH dramatically rescued the clonogenic survival of Gln-deprived cells (FIG. 29). Together, these data support the idea that Gln is utilized by PDAC cells to produce reducing equivalents, which are required to support continued tumor growth.

Figure 31A:
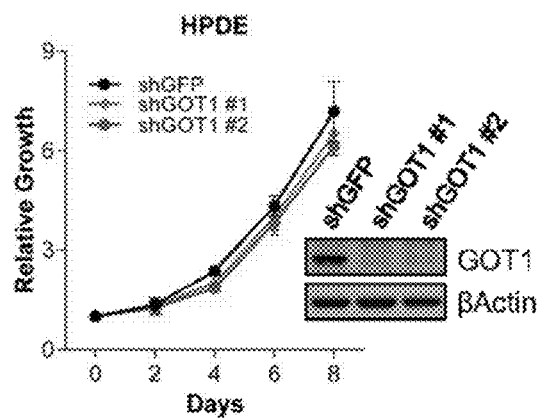
FIGS. 31A and 31B contain line graphs plotting the relative proliferation of HPDE (FIG. 31A) and IMR90 (FIG. 31B) cells expressing a control shRNA (shGFP) or shRNAs targeting GOT1 (#1 and #2); error bars represent s.d. of triplicate wells from a representative experiment. The inset in each graph is a photograph of a Western blot result demonstrating GOT1 knockdown with the shRNA targeting GOT1 in the cells.
Figure 31B:
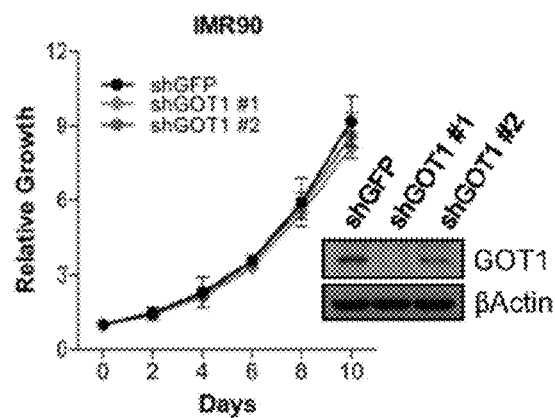

In contrast to PDAC, which rely on Gln for redox homeostasis, this pathway appears to be dispensable in normal cells. Indeed, treatment of non-transformed human pancreatic ductal cells (HPDE) and human diploid fibroblasts (IMR90) with AOA had no significant effect on growth (FIG. 30A, 30B). Interestingly, HPDE cells, unlike PDAC cells, were significantly sensitive to EGCG, suggesting a greater reliance on the activity of GLUD1. Consistent with these results, GOT1 knockdown did not impair the growth of the normal cell lines HPDE and IMR90 (FIG. 31A, FIG. 31B). Thus, the GOT1-mediated utilization of the Gln carbon skeleton appears to be a metabolic adaptation that PDAC have acquired as a means to generate reducing power. Indeed, this reliance is so complete that knockdown of any component in this pathway disrupts redox homeostasis and impairs proliferation in PDAC cells.

Example 6: Role of Oncogenic Kras in PDAC Glutamine Metabolism

This example demonstrates that rewiring of Gln metabolism in PDAC is controlled by oncogenic Kras.

It was next investigated whether the rewiring of Gln metabolism in PDAC may be controlled by genetic events that promote PDAC transformation. Mutations in the Kras oncogene are a critical event in PDAC development. Indeed, previous work has demonstrated that glucose metabolism in PDAC is controlled by oncogenic Kras, which leads to altered expression of a number of rate-limiting metabolic enzymes [Ying et al. supra, and U.S. provisional application No. 61/578,116]. To investigate the role of Kras in the metabolic reprogramming of Gln flux, the expression of GOT and GLUD1 upon knockdown of Kras in PDAC cells was assessed.

Figure 32A:
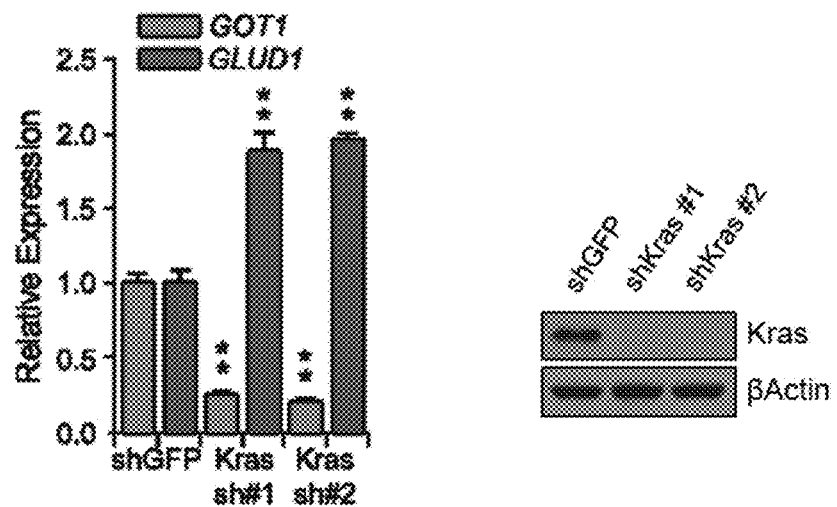
FIG. 32A contains a bar graph (left panel) plotting the relative expression of GLUD1 and GOT1 as determined by quantitative RT-PCR in 8988T cells expressing a control shRNA (shGFP) or two independent shRNAs to Kras (#1 and #2); error bars represent s.d. (n=3); **, p<0.01. The right panel of the figure shows a Western blot result confirming knockdown of Kras expression; βActin was used as a loading control.
Figure 32B:
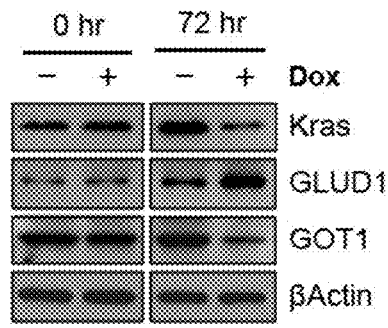
FIG. 32B is an image of Western blot results showing the protein levels of Kras, GLUD1, GOT1 and βActin (loading control) in Panc1 cells expressing a doxycycline-inducible Kras shRNA at the indicated time points (0 and 72 hours (hr)). Error bars represent s.d. (n=3).
Figure 32C:
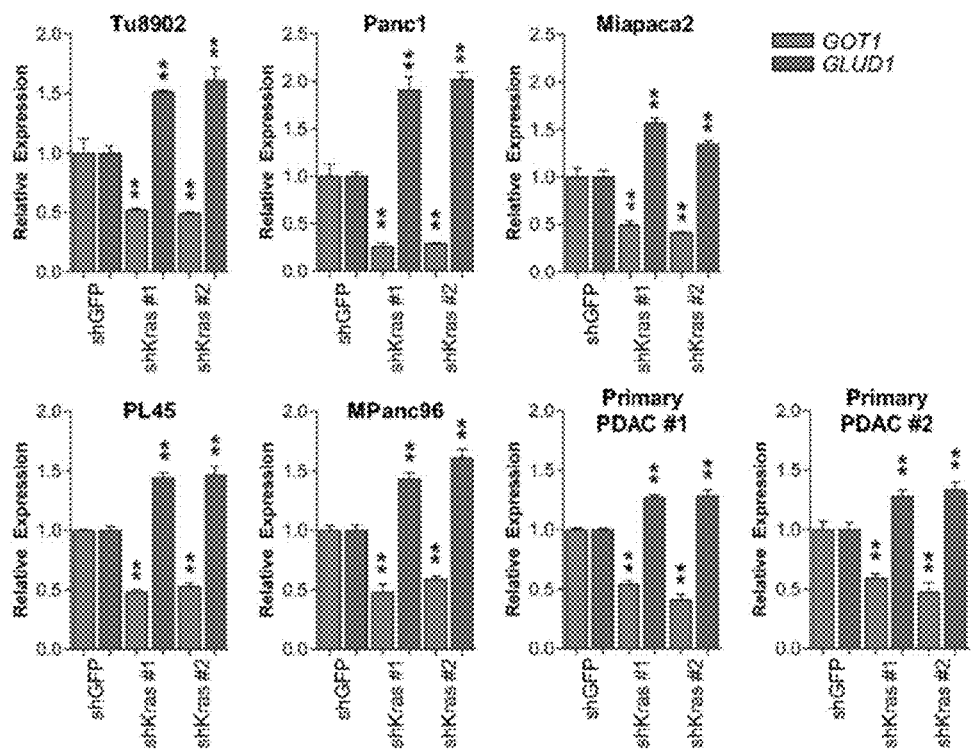
FIG. 32C contains bar graphs quantifying relative expression of GLUD1 and GOT1 as determined by quantitative RT-PCR in PDAC cell lines (8988T, Tu8902, Panc1, Miapaca2, PL45 and MPanc96) and low passage primary human PDAC cell lines (#1 and #2) expressing a control shRNA (shGFP) or two independent shRNAs to Kras (#1 and #2); error bars represent s.d.; **, p<0.01.
Figure 32D:
FIG. 32D is a bar graph quantifying the relative expression (relative to $Kras^{G12D}$ "On") of GLUD1 and GOT1 determined by quantitative RT-PCR in five independent orthotopic tumors derived from inducible Kras mice; error bars represent s.d.; **, p<0.01.

Interestingly, Kras knockdown resulted in a marked increase in GLUD1 and a decrease in GOT1 expression at the transcriptional level (FIG. 32A), as well at the protein level (FIG. 32B) in multiple PDAC lines (FIG. 32C). Additionally, using five independent orthotopic tumors derived from the inducible Kras PDAC model described in Ying et al. (supra), it was determined that expression of GOT1 increased and GLUD1 decreased in an oncogenic Kras-dependent manner in vivo (FIG. 32D). These findings demonstrate that, in PDAC, oncogenic Kras plays a critical role in coordinating the shift in Gln metabolism to maintain tumor growth and survival.

Figure 33:
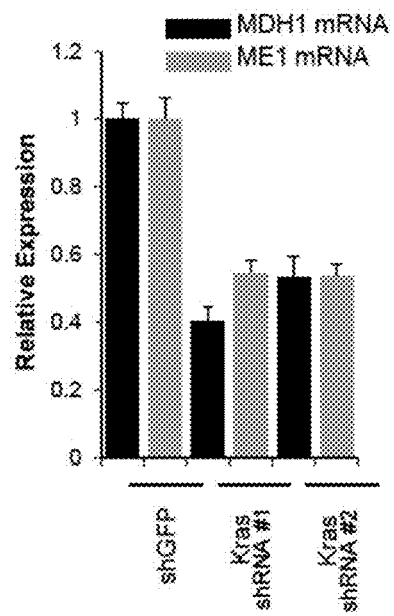
FIG. 33 is a bar graph plotting the relative expression of MDH1 or ME1 mRNA as determined by quantitative RT-PCR in 8988T cells expressing shRNAs to Kras (#1 or #2) or a control shRNA (shGFP); error bars represent s.d. (n=3).

Additionally, expression of both MDH1 and ME1, enzymes involved in the pathway maintaining the cellular redox state, were significantly decreased upon Kras knockdown (FIG. 33). These results demonstrate that in PDAC, oncogenic Kras plays a critical role in coordinating this shift in Gln metabolism to maintain tumor growth and survival. While it has been shown previously in other tumor types that transformation with oncogenic Ras promotes Gln uptake to balance redox demands, this occurs through mechanisms that are distinct from the pathway shown herein to be utilized in PDAC [Weinberg, F. et al. (2010) *Proc Natl Acad Sci USA* 107, 8788-8793; Trachootham, D. et al. (2006) *Cancer Cell* 10, 241-252; DeBerardinis, R. J. et al. (2007) *Proc Natl Acad Sci USA* 104, 19345-19350]. In addition, there may also be context-dependent effects on Gln metabolism, as different oncogenic drivers also have roles in promoting Gln metabolism in other tumor types [Ward, P. S. & Thompson, C. B. (2012) *Cancer Cell* 21, 297-308; Wise et al. supra; Gao, P. et al. (2009) *Nature* 458, 762-765].

Figure 34:
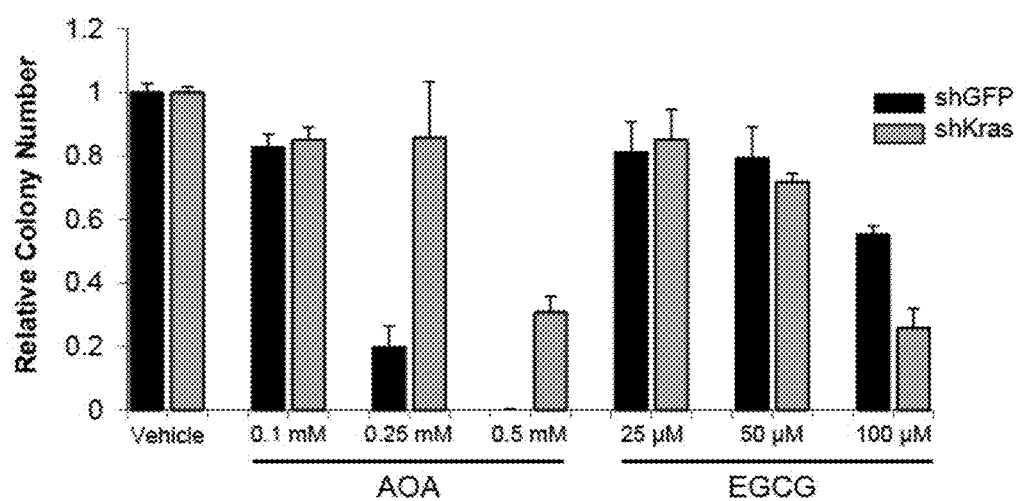
FIG. 34 contains a bar graph plotting the relative colony number (clonogenic growth) of 8988T cells cultured in 10 cm tissue culture dishes and expressing a control shRNA (GFP) or shRNA to Kras (shKras) following treatment with the indicated concentrations of aminooxyacetate (AOA) or Epigallocatechin Gallate (EGCG); error bars represent s.d. (n=3).

Next, the sensitivity of PDAC cells to either AOA or EGCG upon Kras knockdown using 8988T cells, a cell line that is not dependent on Kras for survival [Singh, A. et al. (2009) *Cancer Cell* 15, 489-500], was assessed. Consistent with previous results, AOA significantly inhibited clonogenic growth, whereas EGCG had minimal effects. Interestingly, Kras knockdown made the cells significantly more resistant to AOA and sensitive to EGCG (FIG. 34).

Figure 35:
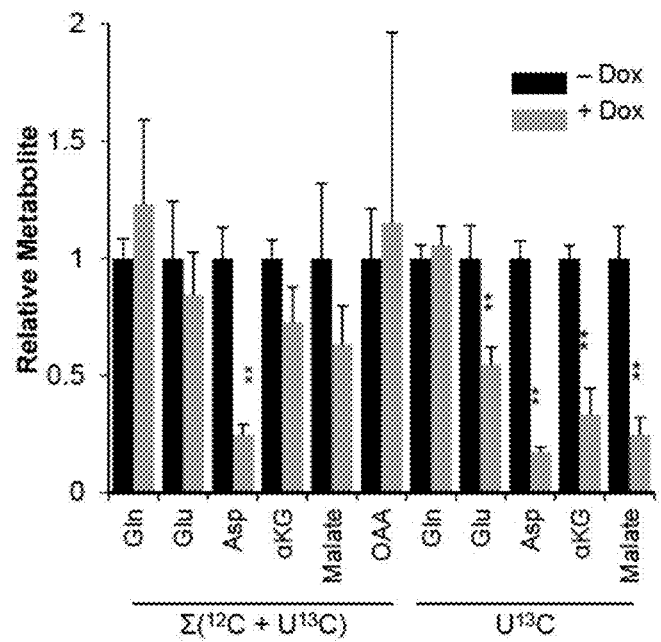
FIG. 35 is a bar graph plotting the relative metabolite abundance presented as those derived from Gln (U-$^{13}$C) or total pools ($^{12}$C+U-$^{13}$C) upon Dox-inducible Kras knockdown in Miapaca pancreatic cancer cells. Abbreviations are as follows: glutamine (Gln); glutamate (Glu); aspartate (Asp); α-ketoglutarate (αKG), oxaloacetate (OAA); error bars represent s.d. (n=3); **, p<0.01.

To confirm the role of oncogenic Kras in the reprogramming of Gln metabolism, a targeted metabolomic analysis using $U^{13}$-Gln was performed to characterize alterations upon Kras knockdown. Indeed, the changes observed were consistent with Kras-supporting the anabolic metabolism of Gln, where multiple metabolites in the GOT1-dependent pathway mediating NAPDH production were significantly deregulated in a manner consistent with the proposed pathway (FIG. 35).

Figure 36:
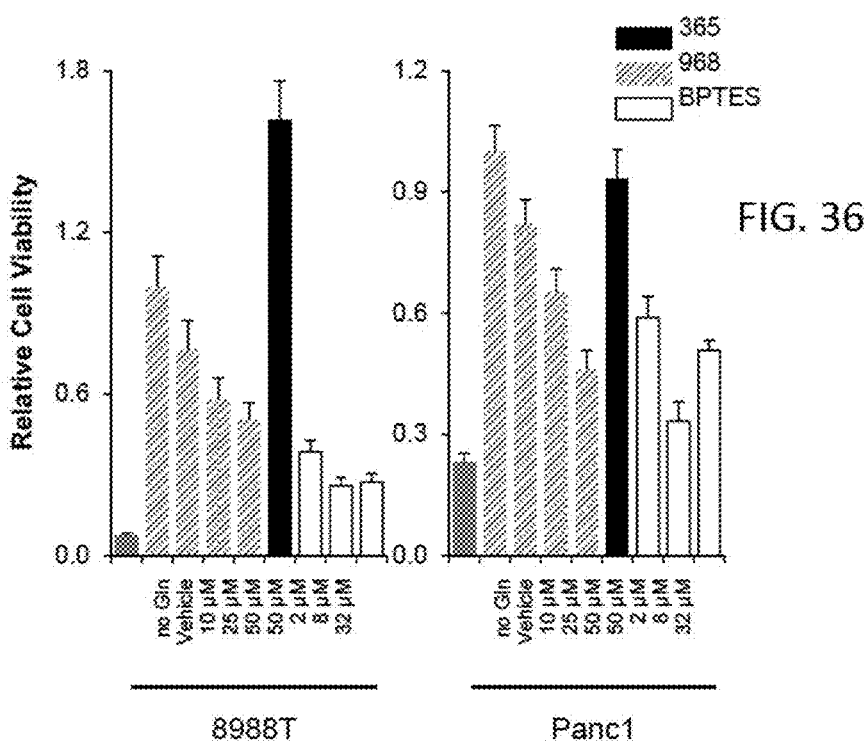
FIG. 36 is a bar graph plotting the relative cell viability of 8988T or Panc1 cells treated with the indicated concentrations of glutaminase (GLS) inhibitors 365 (inactive form), 968 (active form), or BPTES. Error bars represent s.d. (n=3).
Figure 37:
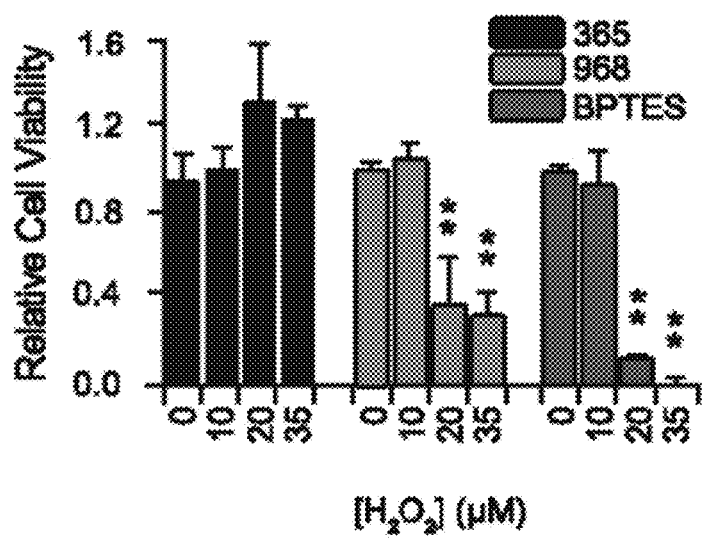
FIGS. 37 and 38 are bar graphs plotting the relative cell viability of 8988T cells (FIG. 37) or Panc1 cells (FIG. 38) treated with GLS inhibitors 968 (active form) (10 mM), 365 (inactive form) (50 mM), or BPTES (100 nM) with increasing concentrations of $H_2O_2$; error bars represent s.d. (n=3)); **, p<0.01.
Figure 38:
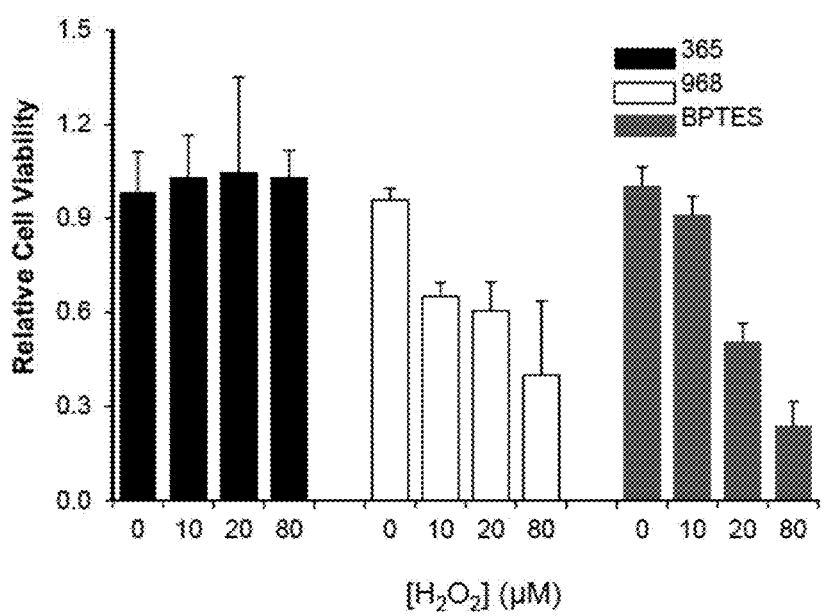

Given the importance of Gln metabolism in maintaining the redox state of PDAC, it was speculated that low Gln and/or Glutaminase (GLS) inhibition may sensitize PDAC to oxidative stress. To test this concept, Gln metabolism was inhibited in PDAC cells using a GLS inhibitor and it was examined whether this would synergize with hydrogen peroxide ($H_2O_2$) treatment. Indeed, two chemically distinct GLS inhibitors (968/365 (active/inactive form) or BPTES) [Wang et al., supra; DeLaBarre, B. et al. (2011) *Biochemistry* 50, 10764-10770] had a growth suppressive effect on PDAC cells, consistent with the GLS knockdown data (FIG. 36). Furthermore, when combined with $H_2O_2$, this effect was dramatically augmented, indicating that PDAC cells are markedly more sensitive to ROS when Gln metabolism is impaired (FIG. 37 and FIG. 38). This finding has significant therapeutic implications, as clinical grade GLS inhibitors are being developed [Vander Heiden, M. G. (2011) *Nat Rev Drug Discov* 10, 671-684], and standard PDAC therapies (such as radiation) lead to the generation of ROS. Moreover, since this aspect of Gln metabolism does not appear as critical in normal cells, these data suggest attractive treatment combinations with an accessible therapeutic window for patients with PDAC.

Collectively, the present Examples demonstrate that PDAC utilizes Gln to generate OAA via GOT1, and, sequentially, this OAA is converted into malate and then pyruvate. This series of reactions results in the transport of NADH into the mitochondria (for oxidative phosphorylation), while simultaneously providing the reducing power necessary to sustain PDAC growth and survival through reducing equivalents generated by ME1 upon conversion of malate into pyruvate. Importantly, oncogenic Kras appears to support this pathway through the regulation of expression of key metabolic enzymes, and this reprogramming of Gln metabolism is indispensable for tumor maintenance in PDAC (FIG. 39).

A number of embodiments of the invention have been described. Nevertheless, it will be understood that various modifications may be made without departing from the spirit and scope of the invention. It is further to be understood that all values are approximate, and are provided for description. Accordingly, other embodiments are within the scope of the following claims.

What is claimed is:

1. A method for treating cancer in a subject comprising a cancer cell comprising an oncogenic Kras mutation, the method comprising administering to the subject a therapeutically effective amount of a composition comprising an inhibitor of the glutamine to pyruvate pathway (GPP) enzyme ME1,
wherein the oncogenic Kras mutation is selected from the group consisting of $Kras^{G12D}$, $Kras^{G12V}$, $Kras^{G13D}$, $Kras^{G12C}$, $Kras^{Q61R}$, $Kras^{Q61L}$, $Kras^{Q61K}$, and $Kras^{G12R}$.

2. The method of claim 1, the method further comprising:
determining the level of one or more markers selected from the group consisting of NADP+, NADPH, GSSG, GSH, pyruvate, and reactive oxygen species (ROS), in a sample obtained from the subject; and
concluding that the treatment was effective if the level of one or more of the markers NADP+, GSSG and ROS is increased, relative to each marker's control level, or if the level of one or more of the markers NADPH, GSH and pyruvate is decreased, relative to each marker's control level; or
concluding that the treatment was not effective if the level of one or more of the markers NADP+, GSSG, and ROS is not increased, relative to each marker's control level, or if the level of one or more of the markers NADPH, GSH and pyruvate is not decreased, relative to each marker's control level.

3. The method of claim 2, comprising determining the level of two or more of the markers selected from the group consisting of NADP+, NADPH, GSSG, GSH, pyruvate, and ROS.

4. The method of claim 3, comprising determining the level of three or more of the markers selected from the group consisting of NADP+, NADPH, GSSG, GSH, pyruvate, and ROS.

5. The method of claim 4, comprising determining the level of four or more of the markers selected from the group consisting of NADP+, NADPH, GSSG, GSH, pyruvate, and ROS.

6. The method of claim 5, comprising determining the level of five or more of the markers selected from the group consisting of NADP+, NADPH, GSSG, GSH, pyruvate, and ROS.

7. The method of claim 6, comprising determining the level of NADP+, NADPH, GSSG, GSH, pyruvate, and ROS.

8. The method of claim 2, wherein each marker's control level is the level of the marker in a sample obtained from the same subject prior to or at the beginning of the treatment or from another subject who is known to comprise an oncogenic Kras mutation and is not undergoing or has not undergone a GPP-targeting treatment.

9. The method of claim 2, wherein each marker's control level is a predetermined reference level of the marker.

10. The method of claim 2, wherein the ROS is a member selected from the group consisting of hydrogen peroxide, super oxide, hydroxyl radical, hypochlorous acid, nitric oxide, peroxyl radical, and singlet oxygen.

11. The method of claim 2, wherein the method further comprises determining the level of at least one additional marker selected from the group consisting of glutamine, glutamate, aspartate, αKG, NAD+, NADH, oxaloacetate, malate, MDH1, and ME1.

12. The method of claim 1, wherein the method further comprises administering a therapeutically effective amount of a composition comprising an inhibitor that targets an additional enzyme of the GPP or that targets a metabolite associated with an enzyme-catalyzed reaction in the GPP.

13. The method of claim 12, wherein the additional enzyme is selected from the group consisting of Kras, GLS, GOT2, GOT1 and MDH1.

14. The method of claim 12, wherein the inhibitor targets a metabolite selected from the group consisting of glutamine, glutamate, aspartate, GSH, NADH, NADPH, oxaloacetate, and malate.

15. The method of claim 1, wherein the subject is a human subject.

16. The method of claim 13, wherein the subject is a human subject.

17. The method of claim 15, wherein the cancer is pancreatic cancer, non-small cell lung cancer, colorectal cancer, or biliary cancer.

18. The method of claim 15, wherein the cancer is pancreatic cancer.

19. The method of claim 1, wherein the oncogenic Kras mutation is selected from the group consisting of $Kras^{G12C}$, $Kras^{Q61R}$, $Kras^{Q61L}$, $Kras^{Q61K}$, and $Kras^{G12R}$.

20. A method for inhibiting growth of a cancer cell in a subject comprising an oncogenic Kras mutation, the method comprising administering to the subject a therapeutically effective amount of a composition comprising an inhibitor of the glutamine to pyruvate pathway (GPP) enzyme ME1,
wherein the oncogenic Kras mutation is selected from the group consisting $Kras^{G12D}$, $Kras^{G12V}$, $Kras^{G13D}$, $Kras^{G12C}$, $Kras^{Q61R}$, $Kras^{Q61L}$, $Kras^{Q61K}$, and $Kras^{G12R}$.

21. The method of claim 20, wherein the method further comprises administering a therapeutically effective amount of a composition comprising an inhibitor that targets an additional enzyme associated with an enzyme-catalyzed reaction of the glutamine to pyruvate pathway (GPP) or that targets a metabolite associated with an enzyme-catalyzed reaction in the GPP.

22. The method of claim 21, wherein the additional enzyme is selected from the group consisting of Kras, GLS, GOT2, GOT1 and MDH1.

23. The method of claim 15, wherein the cancer is pancreatic ductal adenocarcinoma.

24. The method of claim 20, wherein the subject is a human subject.

25. The method of claim 22, wherein the subject is a human subject.

26. The method of claim 24, wherein the cancer cell is a pancreatic cancer cell, a non-small cell lung cancer cell, a colorectal cancer cell, or a biliary cancer cell.

27. The method of claim 24, wherein the cancer cell is a pancreatic cancer cell.

28. The method of claim 24, wherein the cancer cell is a pancreatic ductal adenocarcinoma cell.

29. The method of claim 20, wherein the oncogenic Kras mutation is selected from the group consisting of $Kras^{G12C}$, $Kras^{Q61R}$, $Kras^{Q61L}$, $Kras^{Q61K}$, and $Kras^{G12R}$.

* * * * *

UNITED STATES PATENT AND TRADEMARK OFFICE
CERTIFICATE OF CORRECTION

PATENT NO. : 10,837,015 B2
APPLICATION NO. : 16/158634
DATED : November 17, 2020
INVENTOR(S) : Alec C. Kimmelman et al.

Page 1 of 1

It is certified that error appears in the above-identified patent and that said Letters Patent is hereby corrected as shown below:

On the Title Page

Right column, U.S. Patent Documents, Line 12:
Delete "Cohn" and insert -- Colin --, therefor.

Right column, U.S. Patent Documents, Line 13:
Delete "Cohn" and insert -- Colin --, therefor.

In the Specification

Column 1, Line 9:
Delete "continuation" and insert -- divisional --, therefor.

In the Claims

Column 100, Line 59:
In Claim 11, delete "MEI." and insert -- ME1. --, therefor.

Column 101, Line 22:
In Claim 20, delete "group consisting $Kras^{G12D}$" and insert -- group consisting of $Kras^{G12D}$ --, therefor.

Column 102, Line 17:
In Claim 26, delete "cell ," and insert -- cell, --, therefor.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 36

<210> SEQ ID NO 1
<211> LENGTH: 5436
<212> TYPE: DNA
<213> ORGANISM: Homo sapien

<400> SEQUENCE: 1

| | | | | | | |
|---|---|---|---|---|---|---|
| ggccgcggcg | gcggaggcag | cagcggcggc | ggcagtggcg | gcggcgaagg | tggcggcggc | 60 |
| tcggccagta | ctcccggccc | ccgccatttc | ggactgggag | cgagcgcggc | gcaggcactg | 120 |
| aaggcggcgg | cggggccaga | ggctcagcgg | ctcccaggtg | cgggagagag | gcctgctgaa | 180 |
| aatgactgaa | tataaacttg | tggtagttgg | agctggtggc | gtaggcaaga | gtgccttgac | 240 |
| gatacagcta | attcagaatc | attttgtgga | cgaatatgat | ccaacaatag | aggattccta | 300 |
| caggaagcaa | gtagtaattg | atggagaaac | ctgtctcttg | gatattctcg | acacagcagg | 360 |
| tcaagaggag | tacagtgcaa | tgagggacca | gtacatgagg | actggggagg | gctttctttg | 420 |
| tgtatttgcc | ataaataata | ctaaatcatt | tgaagatatt | caccattata | gagaacaaat | 480 |
| taaaagagtt | aaggactctg | aagatgtacc | tatggtccta | gtaggaaata | atgtgatttt | 540 |
| gccttctaga | acagtagaca | caaacaggc | tcaggactta | gcaagaagtt | atggaattcc | 600 |
| ttttattgaa | acatcagcaa | agacaagaca | gagagtggag | gatgcttttt | atacattggt | 660 |
| gagggagatc | cgacaataca | gattgaaaaa | aatcagcaaa | gaagaaaaga | ctcctggctg | 720 |
| tgtgaaaatt | aaaaaatgca | ttataatgta | atctgggtgt | tgatgatgcc | ttctatacat | 780 |
| tagttcgaga | aattcgaaaa | cataaagaaa | agatgagcaa | agatggtaaa | agaagaaaa | 840 |
| agaagtcaaa | gacaaagtgt | gtaattatgt | aaatacaatt | tgtacttttt | tcttaaggca | 900 |
| tactagtaca | agtggtaatt | tttgtacatt | acactaaatt | attagcattt | gttttagcat | 960 |
| tacctaattt | ttttcctgct | ccatgcagac | tgttagcttt | taccttaaat | gcttatttta | 1020 |
| aaatgacagt | ggaagttttt | ttttcctcta | agtgccagta | ttcccagagt | tttggttttt | 1080 |
| gaactagcaa | tgcctgtgaa | aaagaaactg | aataccctaag | atttctgtct | tggggttttt | 1140 |
| ggtgcatgca | gttgattact | tcttatttt | cttaccaatt | gtgaatgttg | gtgtgaaaca | 1200 |
| aattaatgaa | gcttttgaat | catccctatt | ctgtgtttta | tctagtcaca | taaatggatt | 1260 |
| aattactaat | ttcagttgag | accttctaat | tggtttttac | tgaaacattg | agggaacaca | 1320 |
| aatttatggg | cttcctgatg | atgattcttc | taggcatcat | gtcctatagt | ttgtcatccc | 1380 |
| tgatgaatgt | aaagttacac | tgttcacaaa | ggttttgtct | cctttccact | gctattagtc | 1440 |
| atggtcactc | tccccaaaat | attatatttt | ttctataaaa | agaaaaaat | ggaaaaaat | 1500 |
| tacaaggcaa | tggaaactat | tataaggcca | tttccttttc | acattagata | aattactata | 1560 |
| aagactccta | atagcttttc | ctgttaaggc | agacccagta | tgaaatgggg | attattatag | 1620 |
| caaccatttt | ggggctatat | ttacatgcta | ctaaatttt | ataataattg | aaaagatttt | 1680 |
| aacaagtata | aaaaattctc | ataggaatta | aatgtagtct | ccctgtgtca | gactgctctt | 1740 |
| tcatagtata | actttaaatc | ttttcttcaa | cttgagtctt | tgaagatagt | tttaattctg | 1800 |
| cttgtgacat | taaaagatta | tttgggccag | ttatagctta | ttaggtgttg | aagagaccaa | 1860 |

```
ggttgcaagg ccaggccctg tgtgaacctt tgagctttca tagagagttt cacagcatgg    1920
actgtgtccc cacggtcatc cagtgttgtc atgcattggt tagtcaaaat ggggagggac    1980
tagggcagtt tggatagctc aacaagatac aatctcactc tgtggtggtc ctgctgacaa    2040
atcaagagca ttgcttttgt ttcttaagaa aacaaactct ttttttaaaaa ttacttttaa    2100
atattaactc aaaagttgag attttggggt ggtggtgtgc caagacatta atttttttt    2160
taaacaatga agtgaaaaag ttttacaatc tctaggtttg gctagttctc ttaacactgg    2220
ttaaattaac attgcataaa cacttttcaa gtctgatcca tatttaataa tgctttaaaa    2280
taaaaataaa aacaatcctt tgataaaatt taaaatgtta cttattttaa aataaatgaa    2340
gtgagatggc atggtgaggt gaaagtatca ctggactagg aagaaggtga cttaggttct    2400
agataggtgt cttttaggac tctgattttg aggacatcac ttactatcca tttcttcatg    2460
ttaaaagaag tcatctcaaa ctcttagttt ttttttttta caactatgta atttatattc    2520
catttacata aggatacact tatttgtcaa gctcagcaca atctgtaaat ttttaaccta    2580
tgttacacca tcttcagtgc cagtcttggg caaaattgtg caagaggtga agtttatatt    2640
tgaatatcca ttctcgtttt aggactcttc ttccatatta gtgtcatctt gcctccctac    2700
cttccacatg ccccatgact tgatgcagtt ttaatacttg taattcccct aaccataaga    2760
tttactgctg ctgtggatat ctccatgaag ttttcccact gagtcacatc agaaatgccc    2820
tacatcttat ttcctcaggg ctcaagagaa tctgacagat accataaagg gatttgacct    2880
aatcactaat tttcaggtgg tggctgatgc tttgaacatc tctttgctgc ccaatccatt    2940
agcgacagta ggattttca aacctggtat gaatagacag aaccctatcc agtggaagga    3000
gaatttaata agatagtgc tgaaagaatt ccttaggtaa tctataacta ggactactcc    3060
tggtaacagt aatacattcc attgttttag taaccagaaa tcttcatgca atgaaaaata    3120
cttaaattca tgaagcttac tttttttttt tggtgtcaga gtctcgctct tgtcacccag    3180
gctggaatgc agtggcgcca tctcagctca ctgcaacctc catctcccag gttcaagcga    3240
ttctcgtgcc tcggcctcct gagtagctgg gattacaggc gtgtgccact acactcaact    3300
aattttttgta ttttttaggag agacggggtt tcaccctgtt ggccaggctg gtctcgaact    3360
cctgacctca agtgattcac ccaccttggc ctcataaacc tgttttgcag aactcattta    3420
ttcagcaaat atttattgag tgcctaccag atgccagtca ccgcacaagg cactgggtat    3480
atggtatccc caaacaagag acataatccc ggtccttagg tagtgctagt gtggtctgta    3540
atatcttact aaggcctttg gtatacgacc cagagataac acgatgcgta ttttagtttt    3600
gcaaagaagg ggtttggtct ctgtgccagc tctataattg ttttgctacg attccactga    3660
aactcttcga tcaagctact ttatgtaaat cacttcattg ttttaaagga ataaacttga    3720
ttatattgtt ttttatttg gcataactgt gattcttta ggacaattac tgtacacatt    3780
aaggtgtatg tcagatattc atattgaccc aaatgtgtaa tattccagtt ttctctgcat    3840
aagtaattaa aatatactta aaaattaata gttttatctg ggtacaaata aacaggtgcc    3900
tgaactagtt cacagacaag gaaacttcta tgtaaaaatc actatgattt ctgaattgct    3960
atgtgaaact acagatcttt ggaacactgt ttaggtaggg tgttaagact tacacagtac    4020
ctcgtttcta cacagagaaa gaaatggcca tacttcagga actgcagtgc ttatgagggg    4080
atatttaggc ctcttgaatt tttgatgtag atgggcattt ttttaaggta gtggttaatt    4140
acctttatgt gaactttgaa tggtttaaca aaagattgt ttttgtagag attttaaagg    4200
gggagaattc tagaaataaa tgttacctaa ttattacagc cttaaagaca aaaatccttg    4260
```

| | |
|---|---|
| ttgaagttttt tttaaaaaaa gctaaattac atagacttag gcattaacat gtttgtggaa | 4320 |
| gaatatagca gacgtatatt gtatcatttg agtgaatgtt cccaagtagg cattctaggc | 4380 |
| tctatttaac tgagtcacac tgcataggaa tttagaacct aacttttata ggttatcaaa | 4440 |
| actgttgtca ccattgcaca attttgtcct aatatataca tagaaacttt gtggggcatg | 4500 |
| ttaagttaca gtttgcacaa gttcatctca tttgtattcc attgattttt ttttcttct | 4560 |
| aaacattttt tcttcaaaca gtatataact ttttttaggg gattttttt tagacagcaa | 4620 |
| aaactatctg aagatttcca tttgtcaaaa agtaatgatt tcttgataat tgtgtagtaa | 4680 |
| tgttttttag aacccagcag ttaccttaaa gctgaattta tatttagtaa cttctgtgtt | 4740 |
| aatactggat agcatgaatt ctgcattgag aaactgaata gctgtcataa aatgaaactt | 4800 |
| tctttctaaa gaaagatact cacatgagtt cttgaagaat agtcataact agattaagat | 4860 |
| ctgtgtttta gtttaatagt ttgaagtgcc tgtttgggat aatgataggt aatttagatg | 4920 |
| aatttagggg aaaaaaaagt tatctgcaga tatgttgagg gcccatctct ccccccacac | 4980 |
| ccccacagag ctaactgggt tacagtgttt tatccgaaag tttccaattc cactgtcttg | 5040 |
| tgttttcatg ttgaaaatac ttttgcattt ttcctttgag tgccaatttc ttactagtac | 5100 |
| tatttcttaa tgtaacatgt ttacctgaaa tgtatttaa ctattttgt atagtgtaaa | 5160 |
| ctgaaacatg cacattttgt acattgtgct ttcttttgtg ggacatatgc agtgtgatcc | 5220 |
| agttgttttc catcatttgg ttgcgctgac ctaggaatgt tggtcatatc aaacattaaa | 5280 |
| aatgaccact cttttaattg aaattaactt ttaaatgttt ataggagtat gtgctgtgaa | 5340 |
| gtgatctaaa atttgtaata ttttgtcat gaactgtact actcctaatt attgtaatgt | 5400 |
| aataaaaata gttacagtga caaaaaaaaa aaaaaa | 5436 |

<210> SEQ ID NO 2
<211> LENGTH: 5312
<212> TYPE: DNA
<213> ORGANISM: homo sapien

<400> SEQUENCE: 2

| | |
|---|---|
| ggccgcggcg gcggaggcag cagcggcggc ggcagtggcg gcggcgaagg tggcggcggc | 60 |
| tcggccagta ctcccggccc ccgccatttc ggactgggag cgagcgcggc gcaggcactg | 120 |
| aaggcggcgg cggggccaga ggctcagcgg ctcccaggtg cggagagag gcctgctgaa | 180 |
| aatgactgaa tataaacttg tggtagttgg agctggtggc gtaggcaaga gtgccttgac | 240 |
| gatacagcta attcagaatc attttgtgga cgaatatgat ccaacaatag aggattccta | 300 |
| caggaagcaa gtagtaattg atggagaaac ctgtctcttg gatattctcg acacagcagg | 360 |
| tcaagaggag tacagtgcaa tgagggacca gtacatgagg actggggagg ctttctttg | 420 |
| tgtatttgcc ataaataata ctaaatcatt tgaagatatt caccattata gagaacaaat | 480 |
| taaaagagtt aaggactctg aagatgtacc tatggtccta gtaggaaata atgtgatttt | 540 |
| gccttctaga acagtagaca aaaacaggc tcaggactta gcaagaagtt atggaattcc | 600 |
| ttttattgaa acatcagcaa agacaagaca gggtgttgat gatgccttct atacattagt | 660 |
| tcgagaaatt cgaaacata agaaaagat gagcaaagat ggtaaaaaga agaaaaagaa | 720 |
| gtcaaagaca aagtgtgtaa ttatgtaaat acaatttgta cttttttctt aaggcatact | 780 |
| agtacaagtg gtaatttttg tacattacac taaattatta gcatttgttt tagcattacc | 840 |
| taatttttt cctgctccat gcagactgtt agcttttacc ttaaatgctt atttaaaat | 900 |
| gacagtggaa gttttttttt cctctaagtg ccagtattcc cagagttttg gtttttgaac | 960 |

```
tagcaatgcc tgtgaaaaag aaactgaata cctaagattt ctgtcttggg gttttggtg      1020 catgcagttg attacttctt attttcttta ccaattgtga atgttggtgt gaaacaaatt      1080
aatgaagctt ttgaatcatc cctattctgt gttttatcta gtcacataaa tggattaatt      1140
actaatttca gttgagacct tctaattggt ttttactgaa acattgaggg aacacaaatt      1200
tatgggcttc ctgatgatga ttcttctagg catcatgtcc tatagtttgt catccctgat      1260
gaatgtaaag ttacactgtt cacaaaggtt ttgtctcctt tccactgcta ttagtcatgg      1320
tcactctccc caaaatatta tatttttct ataaaagaa aaaatggaa aaaaattaca        1380 aggcaatgga aactattata aggccatttc cttttcacat tagataaatt actataaaga      1440
ctcctaatag cttttcctgt taaggcagac ccagtatgaa atggggatta ttatagcaac      1500
cattttgggg ctatatttac atgctactaa attttataa taattgaaaa gattttaaca      1560
agtataaaaa attctcatag gaattaaatg tagtctccct gtgtcagact gctctttcat      1620
agtataactt taaatctttt cttcaacttg agtctttgaa gatagtttta attctgcttg      1680
tgacattaaa agattatttg ggccagttat agcttattag gtgttgaaga gaccaaggtt      1740
gcaaggccag gccctgtgtg aacctttgag cttcataga gagtttcaca gcatggactg       1800
tgtccccacg gtcatccagt gttgtcatgc attggttagt caaaatgggg agggactagg      1860
gcagtttgga tagctcaaca agatacaatc tcactctgtg gtggtcctgc tgacaaatca      1920
agagcattgc ttttgtttct taagaaaaca aactcttttt taaaaattac ttttaaatat      1980
taactcaaaa gttgagattt tggggtggtg gtgtgccaag acattaattt ttttttaaa      2040 caatgaagtg aaaagttttt acaatctcta ggtttggcta gttctcttaa cactggttaa      2100
attaacattg cataaacact tttcaagtct gatccatatt taataatgct ttaaaataaa      2160
aataaaaaca atccttttga taaatttaaa atgttactta ttttaaaata aatgaagtga      2220
gatggcatgg tgaggtgaaa gtatcactgg actaggaaga aggtgactta ggttctagat      2280
aggtgtcttt taggactctg attttgagga catcacttac tatccatttc ttcatgttaa      2340
aagaagtcat ctcaaactct tagttttttt ttttacaac tatgtaattt atattccatt       2400
tacataagga tacacttatt tgtcaagctc agcacaatct gtaaattttt aacctatgtt      2460
acaccatctt cagtgccagt cttgggcaaa attgtgcaag aggtgaagtt tatatttgaa      2520
tatccattct cgttttagga ctcttcttcc atattagtgt catcttgcct ccctaccttc      2580
cacatgcccc atgacttgat gcagttttaa tacttgtaat tcccctaacc ataagattta      2640
ctgctgctgt ggatatctcc atgaagtttt cccactgagt cacatcagaa atgccctaca      2700 tcttattcc tcagggctca agagaatctg acagatacca taagggatt tgacctaatc        2760 actaattttc aggtggtggc tgatgctttg aacatctctt tgctgcccaa tccattagcg      2820
acagtaggat ttttcaaacc tggtatgaat agacagaacc ctatccagtg gaaggagaat      2880
ttaataaaga tagtgctgaa agaattcctt aggtaatcta taactaggac tactcctggt      2940
aacagtaata cattccattg ttttagtaac cagaaatctt catgcaatga aaaatacttt      3000
aattcatgaa gcttactttt tttttttggt gtcagagtct cgctcttgtc acccaggctg      3060
gaatgcagtg gcgccatctc agctcactgc aacctccatc tcccaggttc aagcgattct      3120
cgtgcctcgg cctcctgagt agctgggatt acaggcgtgt gccactacac tcaactaatt      3180
tttgtatttt taggagagac ggggtttcac cctgttggcc aggctggtct cgaactcctg      3240
acctcaagtg attcacccac cttggcctca taaacctgtt ttgcagaact catttattca      3300
gcaaatattt attgagtgcc taccagatgc cagtcaccgc acaaggcact gggtatatgg      3360
```

```
tatccccaaa caagagacat aatcccggtc cttaggtagt gctagtgtgg tctgtaatat   3420
cttactaagg cctttggtat acgacccaga gataacacga tgcgtatttt agttttgcaa   3480
agaaggggtt tggtctctgt gccagctcta taattgtttt gctacgattc cactgaaact   3540
cttcgatcaa gctactttat gtaaatcact tcattgtttt aaaggaataa acttgattat   3600
attgtttttt tatttggcat aactgtgatt cttttaggac aattactgta cacattaagg   3660
tgtatgtcag atattcatat tgacccaaat gtgtaatatt ccagttttct ctgcataagt   3720
aattaaaata tacttaaaaa ttaatagttt tatctgggta caaataaaca ggtgcctgaa   3780
ctagttcaca gacaaggaaa cttctatgta aaaatcacta tgatttctga attgctatgt   3840
gaaactacag atctttggaa cactgtttag gtagggtgtt aagacttaca cagtacctcg   3900
tttctacaca gagaaagaaa tggccatact tcaggaactg cagtgcttat gagggggatat   3960
ttaggcctct tgaattttg atgtagatgg gcatttttt aaggtagtgg ttaattacct     4020
ttatgtgaac tttgaatggt ttaacaaaag atttgttttt gtagagattt taaaggggga   4080
gaattctaga aataaatgtt acctaattat tacagcctta aagacaaaaa tccttgttga   4140
agttttttta aaaaaagcta aattacatag acttaggcat taacatgttt gtggaagaat   4200
atagcagacg tatattgtat catttgagtg aatgttccca gtaggcatt ctaggctcta    4260
tttaactgag tcacactgca taggaattta gaacctaact tttataggtt atcaaaactg   4320
ttgtcaccat tgcacaattt tgtcctaata tatacataga aacttgtggg ggcatgttaa   4380
gttacagttt gcacaagttc atctcatttg tattccattg atttttttt tcttctaaac    4440
attttttctt caaacagtat ataactttt ttaggggatt tttttttaga cagcaaaaac    4500
tatctgaaga tttccatttg tcaaaagta atgatttctt gataattgtg tagtaatgtt    4560
ttttagaacc cagcagttac cttaaagctg aatttatatt tagtaacttc tgtgttaata   4620
ctggatagca tgaattctgc attgagaaac tgaatagctg tcataaaatg aaactttctt   4680
tctaaagaaa gatactcaca tgagttcttg aagaatagtc ataactagat taagatctgt   4740
gttttagttt aatagtttga agtgcctgtt tgggataatg ataggtaatt tagatgaatt   4800
taggggaaaa aaaagttatc tgcagatatg ttgagggccc atctctcccc ccacaccccc   4860
acagagctaa ctgggttaca gtgttttatc cgaaagtttc caattccact gtcttgtgtt   4920
ttcatgttga aaatactttt gcattttttcc tttgagtgcc aatttcttac tagtactatt   4980
tcttaatgta acatgtttac ctggaatgta ttttaactat ttttgtatag tgtaaactga   5040
aacatgcaca ttttgtacat tgtgctttct tttgtgggac atatgcagtg tgatccagtt   5100
gttttccatc atttggttgc gctgacctag gaatgttggt catatcaaac attaaaaatg   5160
accactcttt taattgaaat taacttttaa atgtttatag gagtatgtgc tgtgaagtga   5220
tctaaaattt gtaatatttt tgtcatgaac tgtactactc ctaattattg taatgtaata   5280
aaaatagtta cagtgacaaa aaaaaaaaaa aa                                 5312
```

<210> SEQ ID NO 3
<211> LENGTH: 189
<212> TYPE: PRT
<213> ORGANISM: Homo sapien

<400> SEQUENCE: 3

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

```
Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 4
<211> LENGTH: 188
<212> TYPE: PRT
<213> ORGANISM: Homo sapien

<400> SEQUENCE: 4

```
Met Thr Glu Tyr Lys Leu Val Val Val Gly Ala Gly Gly Val Gly Lys
 1                   5                  10                  15

Ser Ala Leu Thr Ile Gln Leu Ile Gln Asn His Phe Val Asp Glu Tyr
             20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 5
<211> LENGTH: 4509
<212> TYPE: DNA
<213> ORGANISM: Homo sapien

```
<400> SEQUENCE: 5
agtgcggagc cttaggcgga gcgaagagaa ccggtcgcgg caatcctagc gcgcagcagc        60
agcagcagca gcagcagcag cagcagcagc agcagcagca cccgcatccg ctgcgggagt       120
ccgagccgga accacaccca agtagctgcc ctttcctctt ctgtcatctc accgccccac       180
cacagaccgc gttccccgag gaaaccggcc gcccacgccc ggagcatcct cccctgttga       240
gcgggcgctg acggacccgg cggcatgatg cggctgcgag gctcggggat gctgcgggac       300
ctgctcctgc ggtcgcccgc cggcgtgagc gcgactctgc ggcgggcaca gcccttggtc       360
accctgtgcc ggcgtccccg aggcggggga cggccggccg cgggcccggc tgccgccgcg       420
cgactccacc cgtggtgggg cggggcggc tggcggcgg agccctcgc gcggggcctg          480
tccagctctc cttcggagat cttgcaggag ctgggcaagg ggagcacgca tccgcagccc       540
ggggtgtcgc cacccgctgc cccggcggcg cccggcccca aggacggccc cggggagacg       600
gacgcgtttg gcaacagcga gggcaaagag ctggtggcct caggtgaaaa taaaataaaa       660
cagggtctgt tacctagctt ggaagatttg ctgttctata caattgctga aggacaagag       720
aaaatacctg ttcataaatt tattacagca ctcaaatcta caggattgcg aacgtctgat       780
cccaggttga aagagtgtat ggatatgtta agattaactc ttcaaacaac atcagatggt       840
gtcatgctag acaaagatct tttaaaaaa tgtgttcaga gcaacattgt tttgttgaca        900
caagcattta aagaaagtt tgtgattcct gactttatgt cttttacctc acacattgat        960
gagttatatg aaagtgctaa aaagcagtct ggaggaaagg ttgcagatta tattcctcaa      1020
ctggccaaat tcagtcccga tttgtggggt gtgtctgttt gtacagtaga tggacagagg      1080
cattctactg gagataccaa agttcccttc tgtcttcagt cctgtgtaaa acctttgaaa      1140
tatgccattg ctgttaatga tcttggaact gaatatgtgc atcgatatgt tggaaaagag      1200
ccgagtggac taagattcaa caaactattt ttgaatgaag atgataaacc acataatcct      1260
atggtaaatg ctggagcaat tgttgtgact tcactaataa agcaaggagt aaataatgct      1320
gaaaaatttg actatgtcat gcagtttttg aataagatgg ctggtaatga atatgttgga      1380
ttcagtaatg caacgtttca gtctgaaaga gaaagtggag atcgaaattt tgcaatagga      1440
tattacttaa aagaaaagaa gtgttttcca gaaggcacag acatggttgg tatattagac      1500
ttctacttcc agctgtgctc cattgaagtg acttgtgaat cagccagtgt gatggctgcg      1560
acactggcta atggtggttt ctgcccaatt actggtgaaa gagtactgag ccctgaagca      1620
gttcgaaata cattgagttt gatgcattcc tgtggcatgt atgacttctc agggcagttt      1680
gctttccatg ttggtcttcc tgcaaaatct ggagttgctg ggggcattct tttagttgtc      1740
cccaatgtta tgggtatgat gtgctggtct cctcctctgg ataagatggg caacagtgtt      1800
aagggaattc acttttgtca cgatcttgtt tctctgtgta atttccataa ctatgataat      1860
ttgagacact ttgcaaaaaa acttgatcct cgaagagaag gtggtgatca aaggcattcc      1920
tttggaccat tggactatga aagtctccaa caagaacttg ctttaaaaga gacagtatgg      1980
aaaaaagtgt cacctgagtc aaatgaggac atctctacaa ctgtagtata tagaatggaa      2040
agtctgggag agaaaagcta agaaatggg ttctagtttc agaatgtttc ttcatttaat       2100
cttttcaaaca tctttagctt ttttttgcaa gttataaata tttatttgag gtattttttg      2160
ttctcaatct tgggtgctgg agccataaag cttttttttc cttttaatct tgtataaag       2220
gcagtagatt aagaagtgca tttgttggtc tttaaaaagt atttacaagt acataaattt      2280
gctttatttt taaaaataca aaaaggaaaa atttaaattt tttttgatgt aattaaaatg      2340
```

```
ttaactatgt ggtcagataa tcccatttta caatagtaac agaaaattgt aattcttagt    2400
tctaaaattc acaaattaaa ctcataagtt ttgttgcatt ttgttttttc ttttccattt    2460
ttaaaactaa tgtgatgtct ttagtggcaa tagaaggtac ttctatgcta aatacaaaac    2520
taaaaaggca aaataatgaa ccccaaatta ttttatttaa aatagcagtg gattataaaa    2580
ttagcttgtg tttacattta tgccattttt ggtgatagat tggctttaca ttttaaaaaa    2640
tttatttaaa aatttatcaa atgctttaaa atatgactcc tactttttt atttttgcaac    2700 tcctctgttc tgtcagagtt gttatataca ggagtgtctt atgttactaa aacattccag    2760
ccaaagaatt tcagatgtga gataatgatg tttcatcaat aaaaagctat aatggttagt    2820
tactcagaag gagaaacagt gagtgtcttc aagtgaattg ttcacctaaa caattttatt    2880
ttcatattat ccacataact ttttctatgt tatatttaaa tatgaatggc aaattttggt    2940
ttttagcttt tacattttat tatcttaatt ttataaatgc taatatttct tttgtgataa    3000
gttatagcat ctcataaagt ttgttctatt tgaagttttt tagagtactt gagaaatgaa    3060
tttagtctgc aggtagtaag tatgctacta aaatacgtta gatctaaatc cttttatttg    3120
gtataaaaat gcaatattga gaatcaaaac ttgtttttaa gagaactata gattctacac    3180
aacctgattt caagtaatta ttcatagtat ttatagttgt cttggcaaag tgattgtaaa    3240
attctgtagg acctattcac acttcttcct tcttccatat acttctctgg ttttccccat    3300
agttccccta aatttcaag tttgttgaaa cctgttaatt ttagtggggg attagaagaa    3360
aaacttggtg gtttcttagc atgatggtgt atgtatgtgg taatggaaag tctgtaaaag    3420
taaatatagt gtagcaaaaa agatttcact gagtatttta gatactagtg caaataaaga    3480
tagaaaatct tgatcataat gtcttaagtt tgggaactgt gatattaaga aaagaaattc    3540
ccttctagag gtgctggcca aaaagccttt tgggctaact taagtattaa atttatatat    3600
ttaaataatt atattttaag ttgtagagga ttttcccaag gattttatgc ttacttgaat    3660
gttctttgaa tgttcagatg catatcctaa ctggatgctt ctcaaggcct tactgcatat    3720
ttgtgttgca tatttatgtt agttgcacca gggccatttg tagtttgggc aaccgaatgc    3780
cttaattgga aaaaaggcat tgtggttttcc cctatgatct aaattgttac atttaccat     3840 ttcattccga agttggtttt actttattaa atgaagattt agttttcata tcgtatacat    3900
agctgtatag atttcaaaat taggttgtta atttgtgtca cttactattt ttgtgttggt    3960
aatgctttaa atgcatactt aaaaatgaag tactgttatc taagctactg tgtttagaaa    4020
atgttaagaa tgagcagaaa ttttttataga aaagtataaa cggaagaaga gataagatac    4080
tgcgaatagg ccctcaaact taaaaagaa aaaactttgc cagttttaag gacatatttt    4140
gattctttca gtattcttaa caccttttta aacaaagttc ttgatagtac ccactattat    4200
tgggtttgtt ttatgccatt attgattctt gatattcaag catttacaat gtagcatatt    4260
tgattttctt ttttctttct ttttttggca tcattaacat ttcatttgaa atgcatattg    4320
ttcttgaagt actttgtttt tagcataaat gttgtgcatt ttatcttagt gtttggatga    4380
aaacatttgt gttgtttagc tttcatttgc tttgtatatt taataatgta cctttatttt    4440
ccagtatgcc tacattttgt attgcacaat aaatttattt taagctgaaa aaaaaaaaa    4500 aaaaaaaaa                                                            4509
```

<210> SEQ ID NO 6
<211> LENGTH: 598
<212> TYPE: PRT
<213> ORGANISM: Homo sapien

<400> SEQUENCE: 6

```
Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Arg Pro Ala Ala Gly Pro
        35                  40                  45

Ala Ala Ala Ala Arg Leu His Pro Trp Trp Gly Gly Gly Trp Pro
    50                  55                  60

Ala Glu Pro Leu Ala Arg Gly Leu Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
    290                 295                 300

Val His Arg Tyr Val Gly Lys Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
        355                 360                 365

Glu Tyr Val Gly Phe Ser Asn Ala Thr Phe Gln Ser Glu Arg Glu Ser
    370                 375                 380

Gly Asp Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
                405                 410                 415
```

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
            435                 440                 445

Ser Pro Glu Ala Val Arg Asn Thr Leu Ser Leu Met His Ser Cys Gly
        450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
        530                 535                 540

Glu Gly Gly Asp Gln Arg His Ser Phe Gly Pro Leu Asp Tyr Glu Ser
545                 550                 555                 560

Leu Gln Gln Glu Leu Ala Leu Lys Glu Thr Val Trp Lys Lys Val Ser
                565                 570                 575

Pro Glu Ser Asn Glu Asp Ile Ser Thr Thr Val Val Tyr Arg Met Glu
            580                 585                 590

Ser Leu Gly Glu Lys Ser
        595

<210> SEQ ID NO 7
<211> LENGTH: 2473
<212> TYPE: DNA
<213> ORGANISM: Homo sapien

<400> SEQUENCE: 7
tctggcccag ggaagtccct gtccttacct tcagcaggag ccggttccct gtgtgtgtgt      60
ccgctcgccc tctgctccgt cctgcggctg cccactgccc tcctacggtc caccatggcc     120
ctgctgcact ccggccgcgt cctccccggg atcgccgccg ccttccaccc gggcctcgcc     180
gccgcggcct ctgccagagc cagctcctgg tggacccatg tggaaatggg acctccagat     240
cccattctgg gagtcactga agcctttaag agggacacca atagcaaaaa gatgaatctg     300
ggagttggtg cctaccggga tgataatgga aagccttacg ttctgcctag cgtccgcaag     360
gcagaggccc agattgccgc aaaaaatttg gacaaggaat acctgcccat gggggactg      420 gctgaatttt gcaaggcatc tgcagaacta gccctgggtg agaacagcga agtcttgaag     480
agtggccggt tgtcactgt gcagaccatt tctggaactg agccttaag gatcggagcc      540 agttttctgc aaagattttt taagttcagc cgagatgtct ttctgcccaa accaacctgg     600
ggaaaccaca cacccatctt cagggatgct ggcatgcagc tacaaggtta tcggtattat     660
gaccccaaga cttgcggttt tgacttcaca ggcgctgtgg aggatatttc aaaaatacca     720
gagcagagtg ttcttcttct gcatgcctgc gcccacaatc ccacgggagt ggacccgcgt     780
ccggaacagt ggaaggaaat agcaacagtg gtgaagaaaa ggaatctctt gcgttctttt     840
gacatggcct accaaggctt tgccagtggt gatggtgata aggatgcctg gctgtgcgc      900 cacttcatcg aacagggcat taatgtttgc tctctgccaa tcatatgccaa gaacatgggc    960 ttatatggtg agcgtgtagg agccttcact atggtctgca aagatgcgga tgaagccaaa    1020
agggtagagt cacagttgaa gatcttgatc cgtcccatgt attccaaccc tccctcaat    1080

```
ggggcccgga ttgctgctgc cattctgaac accccagatt tgcgaaaaca atggctgcaa   1140
gaagtgaaag tcatggctga ccgcatcatt ggcatgcgga ctcaactggt ctccaacctc   1200
aagaaggagg gttccaccca caattggcaa cacatcaccg accaaattgg catgttctgt   1260
ttcacagggc taaagcctga acaggtggag cggctgatca aggagttctc catctacatg   1320
acaaaagatg ccgcatctc tgtggcaggg gtcacctcca gcaacgtggg ctaccttgcc   1380
catgccattc accaggtcac caagtaatgt ccctggtgcg aggaaacaga gacaaccttt   1440
ctgtcttcag cctctgctat tgagagcttc acacagacaa tgagagaggg tggatggtgg   1500
tgagtggatc atttctttca gccacagtgt gtaacactca gcatttgaat gtttctcaga   1560
aaagaacatg tagtgacaca gggcagaggc atccatggct ggcgtctgga atattaaacc   1620
aaactctccc cggtcctttt ttctccaact tttctcaaag agtttacatg tgcaagaaag   1680
tcatcgcacc aaaaaacctg tcaattatgc cattgcaata tttcagaagc tttaactgaa   1740
gtgtcaggtt cctcgtgaga acagcacac gttagaggct ttgagagaag gcctagttct   1800
gtcatgagta gtcggcctcg tgtctgtcct cccatcttgg aacaaccttta tcaacaggcc   1860
gcactgcaga aatgatgttt tatgaaaacc aatgaggctg ctgccactcc agcaagggaa   1920
ataatgcagt ttcctgtctt atttaagaaa agagaaggc tctcttttct cccttgtcat   1980
tgccgttctt ttccttacac gcaaagattt tttaactatt gcagattttc atcccattct   2040
actgcttgat tgaccatcaa ctccatccta tcgagattta tttaagaatg aagaacataa   2100
ttttctgctg atgctgtacc ctcacccttt tcagcaaaga atagtggaga gtaggaaact   2160
gtactttatc tcggcatcct cttgaatgat agtgcaagtt tctccagttg ggatgttgtc   2220
tctgcccggt tggacctcct cccttttgttg aatgtggtgt gcagcctctc atctcacact   2280
gtgagtccag cggcgcaggg tggtaccagg aaagaggata ttctaggctt tgcgtgctgc   2340
tagctgggtt caggcttcac ccactggaaa gaaccaccat ctgctctaac catgtagact   2400
tattgcggcc tggtttctct gttacaataa aattactgta gacccaaaaa aaaaaaaaa   2460
aaaaaaaaaa aaa                                                      2473
```

<210> SEQ ID NO 8
<211> LENGTH: 430
<212> TYPE: PRT
<213> ORGANISM: Homo sapien

<400> SEQUENCE: 8

Met Ala Leu Leu His Ser Gly Arg Val Leu Pro Gly Ile Ala Ala Ala
1               5                   10                  15

Phe His Pro Gly Leu Ala Ala Ala Ser Ala Arg Ala Ser Ser Trp
                20                  25                  30

Trp Thr His Val Glu Met Gly Pro Pro Asp Pro Ile Leu Gly Val Thr
        35                  40                  45

Glu Ala Phe Lys Arg Asp Thr Asn Ser Lys Met Asn Leu Gly Val
    50                  55                  60

Gly Ala Tyr Arg Asp Asp Asn Gly Lys Pro Tyr Val Leu Pro Ser Val
65                  70                  75                  80

Arg Lys Ala Glu Ala Gln Ile Ala Ala Lys Asn Leu Asp Lys Glu Tyr
                85                  90                  95

Leu Pro Ile Gly Gly Leu Ala Glu Phe Cys Lys Ala Ser Ala Glu Leu
            100                 105                 110

Ala Leu Gly Glu Asn Ser Glu Val Leu Lys Ser Gly Arg Phe Val Thr
        115                 120                 125

Val Gln Thr Ile Ser Gly Thr Gly Ala Leu Arg Ile Gly Ala Ser Phe
            130                 135                 140

Leu Gln Arg Phe Phe Lys Phe Ser Arg Asp Val Phe Leu Pro Lys Pro
145                 150                 155                 160

Thr Trp Gly Asn His Thr Pro Ile Phe Arg Asp Ala Gly Met Gln Leu
                165                 170                 175

Gln Gly Tyr Arg Tyr Tyr Asp Pro Lys Thr Cys Gly Phe Asp Phe Thr
            180                 185                 190

Gly Ala Val Glu Asp Ile Ser Lys Ile Pro Glu Gln Ser Val Leu Leu
            195                 200                 205

Leu His Ala Cys Ala His Asn Pro Thr Gly Val Asp Pro Arg Pro Glu
    210                 215                 220

Gln Trp Lys Glu Ile Ala Thr Val Val Lys Lys Arg Asn Leu Phe Ala
225                 230                 235                 240

Phe Phe Asp Met Ala Tyr Gln Gly Phe Ala Ser Gly Asp Gly Asp Lys
                245                 250                 255

Asp Ala Trp Ala Val Arg His Phe Ile Glu Gln Gly Ile Asn Val Cys
            260                 265                 270

Leu Cys Gln Ser Tyr Ala Lys Asn Met Gly Leu Tyr Gly Glu Arg Val
    275                 280                 285

Gly Ala Phe Thr Met Val Cys Lys Asp Ala Asp Glu Ala Lys Arg Val
    290                 295                 300

Glu Ser Gln Leu Lys Ile Leu Ile Arg Pro Met Tyr Ser Asn Pro Pro
305                 310                 315                 320

Leu Asn Gly Ala Arg Ile Ala Ala Ala Ile Leu Asn Thr Pro Asp Leu
                325                 330                 335

Arg Lys Gln Trp Leu Gln Glu Val Lys Val Met Ala Asp Arg Ile Ile
            340                 345                 350

Gly Met Arg Thr Gln Leu Val Ser Asn Leu Lys Lys Glu Gly Ser Thr
    355                 360                 365

His Asn Trp Gln His Ile Thr Asp Gln Ile Gly Met Phe Cys Phe Thr
370                 375                 380

Gly Leu Lys Pro Glu Gln Val Glu Arg Leu Ile Lys Glu Phe Ser Ile
385                 390                 395                 400

Tyr Met Thr Lys Asp Gly Arg Ile Ser Val Ala Gly Val Thr Ser Ser
                405                 410                 415

Asn Val Gly Tyr Leu Ala His Ala Ile His Gln Val Thr Lys
            420                 425                 430

<210> SEQ ID NO 9
<211> LENGTH: 2140
<212> TYPE: DNA
<213> ORGANISM: Homo sapien

<400> SEQUENCE: 9
gcgttccttc tcccctgtgc cttcgtcgtc agaagctggc gattggttaa tcgcgttgcc      60
aagctttgga cgcggctcga ccattggagg ccgcgggccc gccccgccg gctaggtgaa      120 ggtgagtgtc tcctccagtc gcaacggcca gacctgacct gccagctccg ggcgtggggt      180
gaaatctctt gattcctagt ctctcgatat ggcacctccg tcagtctttg ccgaggttcc      240
gcaggcccag cctgtcctgg tcttcaagct cactgccgac ttcagggagg atccggaccc      300
ccgcaaggtc aacctgggag tgggagcata tcgcacggat gactgccatc ctgggttttt      360
gccagtagtg aagaaagtgg agcagaagat tgctaatgac aatagcctaa atcacgagta      420

```
tctgccaatc ctgggcctgg ctgagttccg agctgtgct tctcgtcttg cccttgggga    480
tgacagccca gcactcaagg agaagcgggt aggaggtgtg caatctttgg ggggaacagg    540
tgcacttcga attggagctg atttcttagc gcgttggtac aatggaacaa acaacaagaa    600
cacacctgtc tatgtgtcct caccaacctg ggagaatcac aatgctgtgt tttccgctgc    660
tggttttaaa gacattcggt cctatcgcta ctgggatgca gagaagagag gattggaccct   720
ccagggcttc ctgaatgatc tggagaatgc tcctgagttc tccattgttg tcctccacgc    780
ctgtgcacac aacccaactg ggattgaccc aactccggag cagtggaagc agattgcttc    840
tgtcatgaag caccggtttc tgttccccctt ctttgactca gcctatcagg gcttcgcatc   900
tggaaacctg gagagagatg cctgggccat tcgctatttt gtgtctgaag gcttcgagtt    960
cttctgtgcc cagtccttct ccaagaactt cgggctctac aatgagagag tcgggaatct   1020
gactgtggtt ggaaaagaac ctgagagcat cctgcaagtc ctttcccaga tggagaagat   1080
cgtgcggatt acttggtcca atcccccgc ccagggagca cgaattgtgg ccagcaccct    1140
ctctaaccct gagctctttg aggaatggac aggtaatgtg aagacaatgg ctgaccggat   1200
tctgaccatg agatctgaac tcagggcacg actagaagcc ctcaaaaccc ctgggacctg   1260
gaaccacatc actgatcaaa ttggcatgtt cagcttcact gggttgaacc ccaagcaggt   1320
tgagtatctg gtcaatgaaa agcacatcta cctgctgcca agtggtcgaa tcaacgtgag   1380
tggcttaacc accaaaaatc tagattacgt ggccacctcc atccatgaag cagtcaccaa   1440
aatccagtga agaaacacca cccgtccagt accaccaaag tagttctctg tcatgtgtgt   1500
tccctgcctg cacaaaccta catgtacata ccatggatta gagacacttg caggactgaa   1560
aggctgctct ggtgaggcag cctctgttta accggcccc acatgaagag aacatccctt    1620
gagacgaatt tggagactgg gattagagcc tttggaggtc aaagcaaatt aagattttta   1680
tttaagaata aaagagtact tgatcatga gacataggta tcttgtccct ctcactaaaa    1740
aggagtgttg tgtgtggcgg ccacgtgctt ctatgtggtg tttgactctg tacaaattct   1800
agtcccaaag atcaagttgt ctgaaggagc caaagtgtga atgtgggtgt cggctgcggc   1860
attaaattca tcatctcaac ccagagtgtc tggtctccct gctctttctg catggttgtg   1920
tccctagtcc taagctttgg ttctttaggg tgactgtggt aagaaggata tttaatcatg   1980
acatgcacgg acacgtacat atttaactga aacaagtttt accaaacagt atttactcgt   2040
gatgtgcgta gtgcattctg atatttttga gccattctat tgtgttctac ttcacctaaa   2100
aaaataaaat aaaaatgttg atcaagaaaa aaaaaaaaa                           2140
```

<210> SEQ ID NO 10
<211> LENGTH: 413
<212> TYPE: PRT
<213> ORGANISM: Homo sapien

<400> SEQUENCE: 10

Met Ala Pro Pro Ser Val Phe Ala Glu Val Pro Gln Ala Gln Pro Val
1               5                   10                  15

Leu Val Phe Lys Leu Thr Ala Asp Phe Arg Glu Asp Pro Asp Pro Arg
            20                  25                  30

Lys Val Asn Leu Gly Val Gly Ala Tyr Arg Thr Asp Asp Cys His Pro
        35                  40                  45

Trp Val Leu Pro Val Val Lys Lys Val Glu Gln Lys Ile Ala Asn Asp
    50                  55                  60

```
Asn Ser Leu Asn His Glu Tyr Leu Pro Ile Leu Gly Leu Ala Glu Phe
 65                  70                  75                  80

Arg Ser Cys Ala Ser Arg Leu Ala Leu Gly Asp Asp Ser Pro Ala Leu
                 85                  90                  95

Lys Glu Lys Arg Val Gly Val Gln Ser Leu Gly Gly Thr Gly Ala
            100                 105                 110

Leu Arg Ile Gly Ala Asp Phe Leu Ala Arg Trp Tyr Asn Gly Thr Asn
            115                 120                 125

Asn Lys Asn Thr Pro Val Tyr Val Ser Ser Pro Thr Trp Glu Asn His
130                 135                 140

Asn Ala Val Phe Ser Ala Ala Gly Phe Lys Asp Ile Arg Ser Tyr Arg
145                 150                 155                 160

Tyr Trp Asp Ala Glu Lys Arg Gly Leu Asp Leu Gln Gly Phe Leu Asn
                165                 170                 175

Asp Leu Glu Asn Ala Pro Glu Phe Ser Ile Val Leu His Ala Cys
            180                 185                 190

Ala His Asn Pro Thr Gly Ile Asp Pro Thr Pro Glu Gln Trp Lys Gln
            195                 200                 205

Ile Ala Ser Val Met Lys His Arg Phe Leu Phe Pro Phe Phe Asp Ser
210                 215                 220

Ala Tyr Gln Gly Phe Ala Ser Gly Asn Leu Glu Arg Asp Ala Trp Ala
225                 230                 235                 240

Ile Arg Tyr Phe Val Ser Glu Gly Phe Glu Phe Cys Ala Gln Ser
                245                 250                 255

Phe Ser Lys Asn Phe Gly Leu Tyr Asn Glu Arg Val Gly Asn Leu Thr
            260                 265                 270

Val Val Gly Lys Glu Pro Glu Ser Ile Leu Gln Val Leu Ser Gln Met
            275                 280                 285

Glu Lys Ile Val Arg Ile Thr Trp Ser Asn Pro Pro Ala Gln Gly Ala
290                 295                 300

Arg Ile Val Ala Ser Thr Leu Ser Asn Pro Glu Leu Phe Glu Glu Trp
305                 310                 315                 320

Thr Gly Asn Val Lys Thr Met Ala Asp Arg Ile Leu Thr Met Arg Ser
                325                 330                 335

Glu Leu Arg Ala Arg Leu Glu Ala Leu Lys Thr Pro Gly Thr Trp Asn
            340                 345                 350

His Ile Thr Asp Gln Ile Gly Met Phe Ser Phe Thr Gly Leu Asn Pro
            355                 360                 365

Lys Gln Val Glu Tyr Leu Val Asn Glu Lys His Ile Tyr Leu Leu Pro
370                 375                 380

Ser Gly Arg Ile Asn Val Ser Gly Leu Thr Thr Lys Asn Leu Asp Tyr
385                 390                 395                 400

Val Ala Thr Ser Ile His Glu Ala Val Thr Lys Ile Gln
                405                 410

<210> SEQ ID NO 11
<211> LENGTH: 1461
<212> TYPE: DNA
<213> ORGANISM: Homo sapien

<400> SEQUENCE: 11
ccttcgcgcc ctttggcaag ctcggactca tcttctgggg attgccgcag tgacccagta     60
atgggaaggg attgatttcc accttgcggg gtatggggcg ctcttaggag gactctggag    120
aagtagttgt cctgggagag gagcgatctt aatcctgctg catgacggga ggacaaaatg    180
```

```
cgacgctgca gctattttcc aaaggacgtt acggtgtttg ataaggacga taagtctgaa    240
ccaatcagag tccttgtgac tggagcagct ggtcaaattg catattcact gctgtacagt    300
attggaaatg gatctgtctt tggtaaagat cagcctataa ttcttgtgct gttggatatc    360 accccccatga tgggtgtcct ggacggtgtc taatggaac tgcaagactg tgcccttccc    420
ctcctgaaag atgtcatcgc aacagataaa gaagacgttg ccttcaaaga cctggatgtg    480
gccattcttg tgggctccat gccaagaagg aaggcatgg agagaaaaga tttactgaaa    540
gcaaatgtga aaatcttcaa atcccagggt gcagccttag ataaatacgc caagaagtca    600
gttaaggtta ttgttgtggg taatccagcc aataccaact gcctgactgc ttccaagtca    660
gctccatcca tccccaagga gaacttcagt tgcttgactc gtttggatca aaccgagct    720 aaagctcaaa ttgctcttaa acttggtgtg actgctaatg atgtaaagaa tgtcattatc    780
tggggaaacc attcctcgac tcagtatcca gatgtcaacc atgccaaggt gaaattgcaa    840
ggaaaggaag ttggtgttta tgaagctctg aaagatgaca gctggctcaa gggagaattt    900
gtcacgactg tgcagcagcg tggcgctgct gtcatcaagg ctcgaaaact atccagtgcc    960
atgtctgctg caaaagccat ctgtgaccac gtcagggaca tctggtttgg aaccccagag   1020
ggagagtttg tgtccatggg tgttatctct gatggcaact cctatggtgt tcctgatgat   1080
ctgctctact cattccctgt tgtaatcaag aataagacct ggaagtttgt tgaaggtctc   1140
cctattaatg atttctcacg tgagaagatg gatcttactg caaggaact gacagaagaa   1200 aaagaaagtg cttttgaatt tctttcctct gcctgactag acaatgatgt tactaaatgc   1260
ttcaaagctg aagaatctaa atgtcgtctt tgactcaagt accaaataat aataatgcta   1320
tacttaaatt acttgtgaaa acaacacat tttaaagatt acgtgcttct tggtacaggt   1380
ttgtgaatga cagtttatcg tcatgctgtt agtgtgcatt ctaaataaat atatattcaa   1440
atgaaaaaaa aaaaaaaaaa a                                             1461
```

<210> SEQ ID NO 12
<211> LENGTH: 352
<212> TYPE: PRT
<213> ORGANISM: Homo sapien

<400> SEQUENCE: 12

```
Met Arg Arg Cys Ser Tyr Phe Pro Lys Asp Val Thr Val Phe Asp Lys
1               5                   10                  15

Asp Asp Lys Ser Glu Pro Ile Arg Val Leu Val Thr Gly Ala Ala Gly
            20                  25                  30

Gln Ile Ala Tyr Ser Leu Leu Tyr Ser Ile Gly Asn Gly Ser Val Phe
        35                  40                  45

Gly Lys Asp Gln Pro Ile Ile Leu Val Leu Leu Asp Ile Thr Pro Met
    50                  55                  60

Met Gly Val Leu Asp Gly Val Leu Met Glu Leu Gln Asp Cys Ala Leu
65                  70                  75                  80

Pro Leu Leu Lys Asp Val Ile Ala Thr Asp Lys Glu Asp Val Ala Phe
                85                  90                  95

Lys Asp Leu Asp Val Ala Ile Leu Val Gly Ser Met Pro Arg Arg Glu
            100                 105                 110

Gly Met Glu Arg Lys Asp Leu Leu Lys Ala Asn Val Lys Ile Phe Lys
        115                 120                 125

Ser Gln Gly Ala Ala Leu Asp Lys Tyr Ala Lys Lys Ser Val Lys Val
    130                 135                 140
```

```
Ile Val Val Gly Asn Pro Ala Asn Thr Asn Cys Leu Thr Ala Ser Lys
145                 150                 155                 160

Ser Ala Pro Ser Ile Pro Lys Glu Asn Phe Ser Cys Leu Thr Arg Leu
            165                 170                 175

Asp His Asn Arg Ala Lys Ala Gln Ile Ala Leu Lys Leu Gly Val Thr
        180                 185                 190

Ala Asn Asp Val Lys Asn Val Ile Ile Trp Gly Asn His Ser Ser Thr
    195                 200                 205

Gln Tyr Pro Asp Val Asn His Ala Lys Val Lys Leu Gln Gly Lys Glu
        210                 215                 220

Val Gly Val Tyr Glu Ala Leu Lys Asp Asp Ser Trp Leu Lys Gly Glu
225                 230                 235                 240

Phe Val Thr Thr Val Gln Gln Arg Gly Ala Ala Val Ile Lys Ala Arg
                245                 250                 255

Lys Leu Ser Ser Ala Met Ser Ala Ala Lys Ala Ile Cys Asp His Val
            260                 265                 270

Arg Asp Ile Trp Phe Gly Thr Pro Glu Gly Glu Phe Val Ser Met Gly
        275                 280                 285

Val Ile Ser Asp Gly Asn Ser Tyr Gly Val Pro Asp Asp Leu Leu Tyr
    290                 295                 300

Ser Phe Pro Val Val Ile Lys Asn Lys Thr Trp Lys Phe Val Glu Gly
305                 310                 315                 320

Leu Pro Ile Asn Asp Phe Ser Arg Glu Lys Met Asp Leu Thr Ala Lys
                325                 330                 335

Glu Leu Thr Glu Glu Lys Glu Ser Ala Phe Glu Phe Leu Ser Ser Ala
            340                 345                 350

<210> SEQ ID NO 13
<211> LENGTH: 1665
<212> TYPE: DNA
<213> ORGANISM: Homo sapien

<400> SEQUENCE: 13
gcgcgtgggg gtgatgtcgc taaggggtga ttctcccctc cctagagtta cacacgctat       60
ctctcccgcc aattgccggg ctccatcagg caggtccttt cctcctgagc ccaaaccatc      120
cgtttgttgt cgtcctccaa tcacaggggc tcatcctcag ggactacttt gcaatcggcg      180
cagagcgcag tgagaagagc ttgaaaaaaa cctctggtat cgggaagtgt agttcaacac      240
ttgaaggaaa tgctttggag attgcgccac aaccagggca gcgtaaacta cagttcccag      300
agagcgccgc gtcgggagcg gagcctttc tcgctaacac cgctcgccct ctccgagtca      360
gttccgcggt agaggtgacc tgactctctg aggctcattt gcagttgtt gaaattgtcc      420 ccgcagtttt caatcatgtc tgaaccaatc agagtccttg tgactggagc agctggtcaa      480
attgcatatt cactgctgta cagtattgga aatggatctg tctttggtaa agatcagcct      540
ataattcttg tgctgttgga tatcaccccc atgatgggtg tcctggacgg tgtcctaatg      600
gaactgcaag actgtgccct tcccctcctg aaagatgtca tcgcaacaga taagaagac      660 gttgccttca agacctgga tgtggccatt cttgtgggct ccatgccaag aagggaaggc      720
atggagagaa aagatttact gaaagcaaat gtgaaaatct tcaaatccca gggtgcagcc      780
ttagataaat acgccaagaa gtcagttaag gttattgttg tgggtaatcc agccaatacc      840
aactgcctga ctgcttccaa gtcagctcca tccatcccca aggagaactt cagttgcttg      900
actcgtttgg atcacaaccg agctaaagct caaattgctc ttaaacttgg tgtgactgct      960
```

```
aatgatgtaa agaatgtcat tatctgggga aaccattcct cgactcagta tccagatgtc    1020
aaccatgcca aggtgaaatt gcaaggaaag gaagttggtg tttatgaagc tctgaaagat    1080
gacagctggc tcaagggaga atttgtcacg actgtgcagc agcgtggcgc tgctgtcatc    1140
aaggctcgaa aactatccag tgccatgtct gctgcaaaag ccatctgtga ccacgtcagg    1200
gacatctggt ttggaacccc agagggagag tttgtgtcca tgggtgttat ctctgatggc    1260
aactcctatg gtgttcctga tgatctgctc tactcattcc ctgttgtaat caagaataag    1320
acctggaagt tgttgaagg tctccctatt aatgatttct cacgtgagaa gatggatctt    1380
actgcaaagg aactgacaga agaaaaagaa agtgcttttg aatttctttc ctctgcctga    1440
ctagacaatg atgttactaa atgcttcaaa gctgaagaat ctaaatgtcg tctttgactc    1500
aagtaccaaa taataataat gctatactta aattacttgt gaaaaacaac acattttaaa    1560
gattacgtgc ttcttggtac aggtttgtga atgacagttt atcgtcatgc tgttagtgtg    1620
cattctaaat aaatatatat tcaaatgaaa aaaaaaaaaa aaaaa                    1665
```

<210> SEQ ID NO 14
<211> LENGTH: 334
<212> TYPE: PRT
<213> ORGANISM: Homo sapien

<400> SEQUENCE: 14

Met Ser Glu Pro Ile Arg Val Leu Val Thr Gly Ala Ala Gly Gln Ile
1               5                   10                  15

Ala Tyr Ser Leu Leu Tyr Ser Ile Gly Asn Gly Ser Val Phe Gly Lys
            20                  25                  30

Asp Gln Pro Ile Ile Leu Val Leu Leu Asp Ile Thr Pro Met Met Gly
        35                  40                  45

Val Leu Asp Gly Val Leu Met Glu Leu Gln Asp Cys Ala Leu Pro Leu
    50                  55                  60

Leu Lys Asp Val Ile Ala Thr Asp Lys Glu Asp Val Ala Phe Lys Asp
65                  70                  75                  80

Leu Asp Val Ala Ile Leu Val Gly Ser Met Pro Arg Arg Glu Gly Met
                85                  90                  95

Glu Arg Lys Asp Leu Leu Lys Ala Asn Val Lys Ile Phe Lys Ser Gln
            100                 105                 110

Gly Ala Ala Leu Asp Lys Tyr Ala Lys Lys Ser Val Lys Val Ile Val
        115                 120                 125

Val Gly Asn Pro Ala Asn Thr Asn Cys Leu Thr Ala Ser Lys Ser Ala
    130                 135                 140

Pro Ser Ile Pro Lys Glu Asn Phe Ser Cys Leu Thr Arg Leu Asp His
145                 150                 155                 160

Asn Arg Ala Lys Ala Gln Ile Ala Leu Lys Leu Gly Val Thr Ala Asn
                165                 170                 175

Asp Val Lys Asn Val Ile Ile Trp Gly Asn His Ser Ser Thr Gln Tyr
            180                 185                 190

Pro Asp Val Asn His Ala Lys Val Lys Leu Gln Gly Lys Glu Val Gly
        195                 200                 205

Val Tyr Glu Ala Leu Lys Asp Asp Ser Trp Leu Lys Gly Glu Phe Val
    210                 215                 220

Thr Thr Val Gln Gln Arg Gly Ala Ala Val Ile Lys Ala Arg Lys Leu
225                 230                 235                 240

Ser Ser Ala Met Ser Ala Ala Lys Ala Ile Cys Asp His Val Arg Asp
                245                 250                 255

Ile Trp Phe Gly Thr Pro Glu Gly Phe Val Ser Met Gly Val Ile
    260                 265                 270

Ser Asp Gly Asn Ser Tyr Gly Val Pro Asp Asp Leu Leu Tyr Ser Phe
            275                 280                 285

Pro Val Val Ile Lys Asn Lys Thr Trp Lys Phe Val Glu Gly Leu Pro
290                 295                 300

Ile Asn Asp Phe Ser Arg Glu Lys Met Asp Leu Thr Ala Lys Glu Leu
305                 310                 315                 320

Thr Glu Glu Lys Glu Ser Ala Phe Glu Phe Leu Ser Ser Ala
                325                 330

<210> SEQ ID NO 15
<211> LENGTH: 1364
<212> TYPE: DNA
<213> ORGANISM: Homo sapien

<400> SEQUENCE: 15
ccttcgcgcc ctttggcaag ctcggactca tcttctgggg attgccgcag tgacccagta     60
atgggaaggg attgatttcc accttgcggg gtatggggcg ctcttaggag gactctggag    120
aagtagttgt cctgggagag gagcgatctt aatcctgctg catgacggga ggacaaaatg    180
cgacgctgca gctattttcc aaaggacgtt acggtgtttg ataaggacga taagtctgaa    240
ccaatcagag tccttgtgac tggagcagct ggtcaaattg catattcact gctgtacagt    300
attggaaatg gatctgtctt tggtaaagat cagatgtcat cgcaacagat aagaagacg     360
ttgccttcaa agacctggat gtggccattc ttgtgggctc catgccaaga agggaaggca    420
tggagagaaa agatttactg aaagcaaatg tgaaaatctt caaatcccag ggtgcagcct    480
tagataaata cgccaagaag tcagttaagg ttattgttgt gggtaatcca gccaatacca    540
actgcctgac tgcttccaag tcagctccat ccatccccaa ggagaacttc agttgcttga    600
ctcgttttgga tcacaaccga gctaaagctc aaattgctct taaacttggt gtgactgcta    660
atgatgtaaa gaatgtcatt atctggggaa accattcctc gactcagtat ccagatgtca    720
accatgccaa ggtgaaattg caaggaaagg aagttggtgt ttatgaagct ctgaaagatg    780
acagctggct caagggagaa tttgtcacga ctgtgcagca gcgtggcgct gctgtcatca    840
aggctcgaaa actatccagt gccatgtctg ctgcaaaagc catctgtgac cacgtcaggg    900
acatctggtt tggaaccccca gagggagagt ttgtgtccat gggtgttatc tctgatggca    960
actcctatgg tgttcctgat gatctgctct actcattccc tgttgtaatc aagaataaga   1020
cctggaagtt tgttgaaggt ctccctatta tgatttctc acgtgagaag atggatctta   1080
ctgcaaagga actgacagaa gaaaagaaa gtgcttttga atttctttcc tctgcctgac   1140
tagacaatga tgttactaaa tgcttcaaag ctgaagaatc taaatgtcgt ctttgactca   1200
agtaccaaat aataataatg ctatacttaa attacttgtg aaaacaaca cattttaaag   1260
attacgtgct tcttggtaca ggtttgtgaa tgacagttta tcgtcatgct gttagtgtgc   1320
attctaaata aatatatatt caaatgaaaa aaaaaaaaaa aaaa             1364

<210> SEQ ID NO 16
<211> LENGTH: 245
<212> TYPE: PRT
<213> ORGANISM: Homo sapien

<400> SEQUENCE: 16

| | | | | | | | | | | | | | | |
|---|---|---|---|---|---|---|---|---|---|---|---|---|---|---|
|Met|Pro|Arg|Arg|Glu|Gly|Met|Glu|Arg|Lys|Asp|Leu|Leu|Lys|Ala|Asn|
|1| | | |5| | | | |10| | | | |15|

| | | | | | | | | | | | | | | |
|---|---|---|---|---|---|---|---|---|---|---|---|---|---|---|
|Val|Lys|Ile|Phe|Lys|Ser|Gln|Gly|Ala|Ala|Leu|Asp|Lys|Tyr|Ala|Lys|
| | | | |20| | | | |25| | | | |30|

| | | | | | | | | | | | | | | |
|---|---|---|---|---|---|---|---|---|---|---|---|---|---|---|
|Lys|Ser|Val|Lys|Val|Ile|Val|Gly|Asn|Pro|Ala|Asn|Thr|Asn|Cys|
| | | |35| | | | |40| | | | |45| |

Leu Thr Ala Ser Lys Ser Ala Pro Ser Ile Pro Lys Glu Asn Phe Ser
 50                  55                  60

Cys Leu Thr Arg Leu Asp His Asn Arg Ala Lys Ala Gln Ile Ala Leu
65                   70                  75                  80

Lys Leu Gly Val Thr Ala Asn Asp Val Lys Asn Val Ile Ile Trp Gly
                     85                  90                  95

Asn His Ser Ser Thr Gln Tyr Pro Asp Val Asn His Ala Lys Val Lys
                100                 105                 110

Leu Gln Gly Lys Glu Val Gly Val Tyr Glu Ala Leu Lys Asp Asp Ser
            115                 120                 125

Trp Leu Lys Gly Glu Phe Val Thr Thr Val Gln Gln Arg Gly Ala Ala
130                 135                 140

Val Ile Lys Ala Arg Lys Leu Ser Ser Ala Met Ser Ala Ala Lys Ala
145                 150                 155                 160

Ile Cys Asp His Val Arg Asp Ile Trp Phe Gly Thr Pro Glu Gly Glu
                165                 170                 175

Phe Val Ser Met Gly Val Ile Ser Asp Gly Asn Ser Tyr Gly Val Pro
            180                 185                 190

Asp Asp Leu Leu Tyr Ser Phe Pro Val Val Ile Lys Asn Lys Thr Trp
        195                 200                 205

Lys Phe Val Glu Gly Leu Pro Ile Asn Asp Phe Ser Arg Glu Lys Met
    210                 215                 220

Asp Leu Thr Ala Lys Glu Leu Thr Glu Glu Lys Glu Ser Ala Phe Glu
225                 230                 235                 240

Phe Leu Ser Ser Ala
                245

<210> SEQ ID NO 17
<211> LENGTH: 3519
<212> TYPE: DNA
<213> ORGANISM: Homo sapien

<400> SEQUENCE: 17

```
ctcacacgcc ggctcggatg atctcctgcc atgactcagc gcttctcgca ggctgccctg      60
ctggggacac cggcttcgct cgggcccctc ccgacgcgtc caccccctct cgccacccac     120
gcccgccccc agccgctggg cctttcccag tgcggccgcc gccgccacag ctgcagtcag     180
caccgtcacc ccagcagcat ccgccgcctg caccgcgcgt gcggcccgcc ccggcctgac     240
cccgccgccg aacccggcgc cagccatgga gcccgaagcc cccgtcgcc gccacaccca     300 tcagcgcggc tacctgctga cacggaaccc tcacctcaac aaggacttgg cctttaccct     360
ggaagagaga cagcaattga acattcatgg attgttgcca ccttccttca acagtcagga     420
gatccaggtt cttagagtag taaaaaattt cgagcatctg aactctgact ttgacaggta     480
tcttctctta atggatctcc aagatagaaa tgaaaaactc ttttatagag tgctgacatc     540
tgacattgag aaattcatgc ctattgttta ctccccact gtgggtctgg cttgccaaca     600
atatagtttg gtgtttcgga agccaagagg tctctttatt actatccacg atcgagggca     660
```

```
tattgcttca gttctcaatg catggccaga agatgtcatc aaggccattg tggtgactga      720
tggagagcgt attcttggct tgggagacct tggctgtaat ggaatgggca tccctgtggg      780
taaattggct ctatatacag cttgcggagg gatgaatcct caagaatgtc tgcctgtcat      840
tctggatgtg ggaaccgaaa atgaggagtt acttaaagat ccactctaca ttggactacg      900
gcagagaaga gtaagaggtt ctgaatatga tgattttttg gacgaattca tggaggcagt      960
ttcttccaag tatggcatga attgcctat tcagtttgaa gattttgcca atgtgaatgc     1020
atttcgtctc ctgaacaagt atcgaaacca gtattgcaca ttcaatgatg atattcaagg     1080
aacagcatct gttgcagttg caggtctcct tgcagctctt cgaataacca agaacaaact     1140
gtctgatcaa acaatactat tccaaggagc tggagaggct gccctaggga ttgcacacct     1200
gattgtgatg gccttggaaa aagaaggttt accaaaagag aaagccatca aaagatatg     1260 gctggttgat tcaaaaggat aatagttaa gggacgtgct tccttaacac aagagaaaga     1320
gaagtttgcc catgaacatg aagaaatgaa gaacctagaa gccattgttc aagaaataaa     1380
accaactgcc ctcataggag ttgctgcaat tggtggtgca ttctcagaac aaattctcaa     1440
agatatggct gccttcaatg aacggcctat tattttttgct ttgagtaatc caactagcaa     1500
agcagaatgt tctgcagagc agtgctacaa aataaccaag ggacgtgcaa tttttgccag     1560
tggcagtcct tttgatccag tcactcttcc aaatggacag accctatatc ctggccaagg     1620
caacaattcc tatgtgttcc ctggagttgc tcttggtgtt gtggcgtgtg gattgaggca     1680
gatcacagat aatatttttcc tcactactgc tgaggttata gctcagcaag tgtcagataa     1740
acacttggaa gagggtcggc tttatcctcc tttgaatacc attagagatg tttctctgaa     1800
aattgcagaa aagattgtga aagatgcata ccaagaaaag acagccacag tttatcctga     1860
accgcaaaac aaagaagcat ttgtccgctc ccagatgtat agtactgatt atgaccagat     1920
tctacctgat tgttattctt ggcctgaaga ggtgcagaaa atacagacca agttgacca     1980 gtaggataat agcaaacatt tctaactcta ttaatgaggt ctttaaacct ttcataattt     2040
ttaaaggttg gaatctttta taatgattca taagacactt agattaagat tttactttaa     2100
cagtctaaaa attgatagaa gaatatcgat ataaattggg ataaacatca catgagacaa     2160
ttttgcttca cttttgcctt ctggttattta tggtttctgt ctgaattatt ctgcctacgt     2220
tctctttaaa agctgttgta cgtactacgg agaaactcat cattttttata caggacacta     2280 atgggaagac caaaattact aataaattga cataaccaac attaaaactc ataattattt     2340
tgttgaccat tttgttaaaa tctacttttc aaaaaaaaaa agctagaaat gaatctaggc     2400
gtaggtgaac ttttgctaag cagaaataac actactttgt tgcctagaga aagataactt     2460
ctcaagtatt tttattccag tcctagatca tatatgttct tttgtgcaac ggaattctaa     2520
cagttctaag agaaagatca ctgctgttta cagcgccttg tgcagcctta gattttaata     2580
ttcttttgtc attgttacat ctcatagagt aaagctctta ttaccttgat cctgagtcag     2640
aaatcccacc tgaaatcacc ttttttcccc cttgatcaaa catcccatcc ttcagctacc     2700
atactgttgc tacagggatt ttgtggactg tggcccctgt cctgaggttg gcaccttcag     2760
ttcagcacag cctgagcagt gagaaggtct gaaggagag tatatagtta agatccttga     2820
gaaagggctg cctgaggaac tgacctctta aagatctcag gatctttaag acaacaagtt     2880
aggttcctac tggagttacc tgccagaatg gcctcttaat taactcaggt aatgaagagc     2940
taactgtgtt ataatcatct tgcttttgcc tgaattttgga gaaagtatta taattaagtt     3000
cccagtatca gaaatgtcct tacataagat taaaatatct tgatgactaa taccattcta     3060
```

-continued

```
tgagaaagag tagttatatg cccagactgt attaatttac tttagaaact aatgtttgaa    3120
gtaatggaaa aaattttaaa ttataaagct aaggtgcaat aacatttgct acttatttat    3180
agaattattt gaagaatttt gttttgaag taatgcttta aggagtataa gatattcaag     3240
ataaattata ctataaaatg attttattga aagttgaagg ttacacaaat tgttttaggt    3300
atgagcagaa gaggttaagg tatttctaaa ggtaacatat agtcaagagt ttcctcaaaa    3360
tagttatttg gagaagaatc agaatgtctg tgtatttctt gtctgtttct atgttgtctt    3420
atagctctga ctaaatgtgt ttacctatgc aaaagattta ttaaagcata gaaaaggtga    3480
atgaataaaa atataaaata attgtccttt ttcttaaaa                           3519
```

<210> SEQ ID NO 18
<211> LENGTH: 572
<212> TYPE: PRT
<213> ORGANISM: Homo sapien

<400> SEQUENCE: 18

```
Met Glu Pro Glu Ala Pro Arg Arg Arg His Thr His Gln Arg Gly Tyr
1               5                   10                  15

Leu Leu Thr Arg Asn Pro His Leu Asn Lys Asp Leu Ala Phe Thr Leu
            20                  25                  30

Glu Glu Arg Gln Gln Leu Asn Ile His Gly Leu Leu Pro Pro Ser Phe
        35                  40                  45

Asn Ser Gln Glu Ile Gln Val Leu Arg Val Val Lys Asn Phe Glu His
    50                  55                  60

Leu Asn Ser Asp Phe Asp Arg Tyr Leu Leu Leu Met Asp Leu Gln Asp
65                  70                  75                  80

Arg Asn Glu Lys Leu Phe Tyr Arg Val Leu Thr Ser Asp Ile Glu Lys
                85                  90                  95

Phe Met Pro Ile Val Tyr Thr Pro Thr Val Gly Leu Ala Cys Gln Gln
            100                 105                 110

Tyr Ser Leu Val Phe Arg Lys Pro Arg Gly Leu Phe Ile Thr Ile His
        115                 120                 125

Asp Arg Gly His Ile Ala Ser Val Leu Asn Ala Trp Pro Glu Asp Val
    130                 135                 140

Ile Lys Ala Ile Val Val Thr Asp Gly Glu Arg Ile Leu Gly Leu Gly
145                 150                 155                 160

Asp Leu Gly Cys Asn Gly Met Gly Ile Pro Val Gly Lys Leu Ala Leu
                165                 170                 175

Tyr Thr Ala Cys Gly Gly Met Asn Pro Gln Glu Cys Leu Pro Val Ile
            180                 185                 190

Leu Asp Val Gly Thr Glu Asn Glu Leu Leu Lys Asp Pro Leu Tyr
        195                 200                 205

Ile Gly Leu Arg Gln Arg Arg Val Arg Gly Ser Glu Tyr Asp Asp Phe
    210                 215                 220

Leu Asp Glu Phe Met Glu Ala Val Ser Ser Lys Tyr Gly Met Asn Cys
225                 230                 235                 240

Leu Ile Gln Phe Glu Asp Phe Ala Asn Val Asn Ala Phe Arg Leu Leu
                245                 250                 255

Asn Lys Tyr Arg Asn Gln Tyr Cys Thr Phe Asn Asp Asp Ile Gln Gly
            260                 265                 270

Thr Ala Ser Val Ala Val Ala Gly Leu Leu Ala Ala Leu Arg Ile Thr
        275                 280                 285
```

-continued

```
Lys Asn Lys Leu Ser Asp Gln Thr Ile Leu Phe Gln Gly Ala Gly Glu
290                 295                 300

Ala Ala Leu Gly Ile Ala His Leu Ile Val Met Ala Leu Glu Lys Glu
305                 310                 315                 320

Gly Leu Pro Lys Glu Lys Ala Ile Lys Lys Ile Trp Leu Val Asp Ser
                325                 330                 335

Lys Gly Leu Ile Val Lys Gly Arg Ala Ser Leu Thr Gln Glu Lys Glu
                340                 345                 350

Lys Phe Ala His Glu His Glu Met Lys Asn Leu Glu Ala Ile Val
                355                 360                 365

Gln Glu Ile Lys Pro Thr Ala Leu Ile Gly Val Ala Ala Ile Gly Gly
370                 375                 380

Ala Phe Ser Glu Gln Ile Leu Lys Asp Met Ala Ala Phe Asn Glu Arg
385                 390                 395                 400

Pro Ile Ile Phe Ala Leu Ser Asn Pro Thr Ser Lys Ala Glu Cys Ser
                405                 410                 415

Ala Glu Gln Cys Tyr Lys Ile Thr Lys Gly Arg Ala Ile Phe Ala Ser
                420                 425                 430

Gly Ser Pro Phe Asp Pro Val Thr Leu Pro Asn Gly Gln Thr Leu Tyr
                435                 440                 445

Pro Gly Gln Gly Asn Asn Ser Tyr Val Phe Pro Gly Val Ala Leu Gly
                450                 455                 460

Val Val Ala Cys Gly Leu Arg Gln Ile Thr Asp Asn Ile Phe Leu Thr
465                 470                 475                 480

Thr Ala Glu Val Ile Ala Gln Gln Val Ser Asp Lys His Leu Glu Glu
                485                 490                 495

Gly Arg Leu Tyr Pro Pro Leu Asn Thr Ile Arg Asp Val Ser Leu Lys
                500                 505                 510

Ile Ala Glu Lys Ile Val Lys Asp Ala Tyr Gln Glu Lys Thr Ala Thr
                515                 520                 525

Val Tyr Pro Glu Pro Gln Asn Lys Glu Ala Phe Val Arg Ser Gln Met
530                 535                 540

Tyr Ser Thr Asp Tyr Asp Gln Ile Leu Pro Asp Cys Tyr Ser Trp Pro
545                 550                 555                 560

Glu Glu Val Gln Lys Ile Gln Thr Lys Val Asp Gln
                565                 570
```

<210> SEQ ID NO 19
<211> LENGTH: 58
<212> TYPE: DNA
<213> ORGANISM: Artificial
<220> FEATURE:
<223> OTHER INFORMATION: Primer

<400> SEQUENCE: 19
ccggccacat gagaagacgt ttcttctcga gaagaaacgt cttctcatgt ggttttg     58

<210> SEQ ID NO 20
<211> LENGTH: 58
<212> TYPE: DNA
<213> ORGANISM: Artificial
<220> FEATURE:
<223> OTHER INFORMATION: Primer

<400> SEQUENCE: 20
aattcaaaaa ccacatgaga agacgtttct tctcgagaag aaacgtcttc tcatgtgg     58

<210> SEQ ID NO 21
<211> LENGTH: 21
<212> TYPE: DNA
<213> ORGANISM: Artificial
<220> FEATURE:
<223> OTHER INFORMATION: Primer

<400> SEQUENCE: 21
gcacagacat ggttggtata t                                    21

<210> SEQ ID NO 22
<211> LENGTH: 21
<212> TYPE: DNA
<213> ORGANISM: Artificial
<220> FEATURE:
<223> OTHER INFORMATION: Primer

<400> SEQUENCE: 22
gccctgaagc agttcgaaat a                                    21

<210> SEQ ID NO 23
<211> LENGTH: 21
<212> TYPE: DNA
<213> ORGANISM: Artificial
<220> FEATURE:
<223> OTHER INFORMATION: Primer

<400> SEQUENCE: 23
ccctgttgta atcaagaata a                                    21

<210> SEQ ID NO 24
<211> LENGTH: 21
<212> TYPE: DNA
<213> ORGANISM: Artificial
<220> FEATURE:
<223> OTHER INFORMATION: Primer

<400> SEQUENCE: 24
gcaacagata aagaagacgt t                                    21

<210> SEQ ID NO 25
<211> LENGTH: 21
<212> TYPE: DNA
<213> ORGANISM: Artificial
<220> FEATURE:
<223> OTHER INFORMATION: Primer

<400> SEQUENCE: 25
gccttcaatg aacggcctat t                                    21

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
ccaacaatat agtttggtgt t                                    21

<210> SEQ ID NO 27
<211> LENGTH: 21
<212> TYPE: DNA
<213> ORGANISM: Artificial
<220> FEATURE:
<223> OTHER INFORMATION: Primer

<400> SEQUENCE: 27
cccaagaact atactgataa t					21

<210> SEQ ID NO 28
<211> LENGTH: 21
<212> TYPE: DNA
<213> ORGANISM: Artificial
<220> FEATURE:
<223> OTHER INFORMATION: Primer

<400> SEQUENCE: 28
gcagagttcc aagacaggat a					21

<210> SEQ ID NO 29
<211> LENGTH: 21
<212> TYPE: DNA
<213> ORGANISM: Artificial
<220> FEATURE:
<223> OTHER INFORMATION: Primer

<400> SEQUENCE: 29
gcgttggtac aatggaacaa a					21

<210> SEQ ID NO 30
<211> LENGTH: 21
<212> TYPE: DNA
<213> ORGANISM: Artificial
<220> FEATURE:
<223> OTHER INFORMATION: Primer

<400> SEQUENCE: 30
gctaatgaca atagcctaaa t					21

<210> SEQ ID NO 31
<211> LENGTH: 21
<212> TYPE: DNA
<213> ORGANISM: Artificial
<220> FEATURE:
<223> OTHER INFORMATION: Primer

<400> SEQUENCE: 31
gctaatgaca atagcctaaa t					21

<210> SEQ ID NO 32
<211> LENGTH: 21
<212> TYPE: DNA
<213> ORGANISM: Artificial
<220> FEATURE:
<223> OTHER INFORMATION: Primer

<400> SEQUENCE: 32
ccatcaaatg gctccagaca t					21

<210> SEQ ID NO 33
<211> LENGTH: 21
<212> TYPE: DNA
<213> ORGANISM: Artificial
<220> FEATURE:
<223> OTHER INFORMATION: Primer

<400> SEQUENCE: 33
gccaagaagt ttgggactat a					21

```
<210> SEQ ID NO 34
<211> LENGTH: 21
<212> TYPE: DNA
<213> ORGANISM: Artificial
<220> FEATURE:
<223> OTHER INFORMATION: Primer

<400> SEQUENCE: 34
ccagacaact ataaggtgat t                                              21

<210> SEQ ID NO 35
<211> LENGTH: 21
<212> TYPE: DNA
<213> ORGANISM: Artificial
<220> FEATURE:
<223> OTHER INFORMATION: Primer

<400> SEQUENCE: 35
cctcgtttct acacagagaa a                                              21

<210> SEQ ID NO 36
<211> LENGTH: 21
<212> TYPE: DNA
<213> ORGANISM: Artificial
<220> FEATURE:
<223> OTHER INFORMATION: Primer

<400> SEQUENCE: 36
gagggctttc tttgtgtatt t                                              21
```